(12) United States Patent
Divita et al.

(10) Patent No.: US 6,841,535 B2
(45) Date of Patent: Jan. 11, 2005

(54) PEPTIDE-MEDIATED TRANSFECTION AGENTS AND METHODS OF USE

(75) Inventors: Gilles Divita, Paris (FR); May C. Morris, Paris (FR); Jean Mery, Paris (FR); Frederic Heitz, Paris (FR); Joseph Fernandez, Carlsbad, CA (US); John Archdeacon, Carlsbad, CA (US); Kyle Horndorp, Carlsbad, CA (US)

(73) Assignees: Active Motif, Carlsbad, CA (US); Centre National de la Recherche Scientifique, Paris Cedex (FR)

( * ) Notice: Subject to any disclaimer, the term of this patent is extended or adjusted under 35 U.S.C. 154(b) by 254 days.

(21) Appl. No.: 09/915,914

(22) Filed: Jul. 26, 2001

(65) Prior Publication Data

US 2003/0119725 A1 Jun. 26, 2003

Related U.S. Application Data

(60) Provisional application No. 60/221,932, filed on Jul. 31, 2000.

(51) Int. Cl.$^7$ .............................................. A61K 38/10
(52) U.S. Cl. .......................... 514/13; 514/12; 530/324; 530/326
(58) Field of Search ................................ 530/324, 326; 514/12, 13

(56) References Cited

U.S. PATENT DOCUMENTS

| 5,270,163 A | 12/1993 | Gold et al. ..................... 435/6 |
| 5,747,253 A | 5/1998 | Ecker et al. ..................... 435/6 |

FOREIGN PATENT DOCUMENTS

| WO | WO 00/18778 | 4/2000 |

OTHER PUBLICATIONS

Arar et al. (1995), "Synthesis and Antiviral Activity of Peptide-Oligonucleotide Conjugates Prepared by Using N-(Bromoacetyl) Peptides," Bioconjug. Chem., 6, 573–5772.
Beven et al. (1997), "Effects on Mollicutes (Wall–less Bacteria) of Synthetic Peptides Comprising a Signal Peptide or a Membrane Fusion Peptide, and a Nuclear Localization Sequence (NLS)—A Comparison with Melittin," Biochim. Biophys. Acta, 1329, 357–369.
Bongartz et al. (1994), "Improved Biological Activity of Antisense Oligonucleotides Conjugated to a Fusogenic Peptide," Nucleic Acids Res., 22, 4681–4688.
Briggs and Gierasch (1986), "Molecular Mechanisms of Protein Secretion: The Role of the Signal Sequence," Adv. Prot. Chem. 38, 109–180.
Brugidou et al. (1995), "The Retro–Inverso Form of a Homeobox–Derived Short Peptide is Rapidly Internalised by Cultured Neurones: A New Basis for an Efficient Intracellular Delivery System," Biochem. Biophys. Res. Commun., 214, 685–693.
Chaloin et al. (1998), "Design of Carrier Peptide–Oligonucleotide Conjugates with Rapid Membrane Translocation and Nuclear Localization Properties," Biochem. Biophys. Res. Commun., 243, 601–608.
Chaloin et al. (1997), "Synthetic Peptides as Carriers for Cellular Import of Drugs," Lett. Pept. Sci., 4, 231–234.
Chaloin et al. (1997), "Conformations of Primary Amphipathic Carrier Peptides in Membrane Mimicking Environments," Biochemistry, 36, 11179–11187.
Chaloin et al. (1998), "Ionic Channels Formed by a Primary Amphipathic Peptide Containing a Signal Peptide and a Nuclear Localization Sequence," Biochim Biophys. Acta, 1375, 52–60.
Chen et al. (1999), "Selective Killing of Transformed Cells by Cyclin/Cyclin–Dependent Kinase 2 Antagonists," Proc. Natl. Acad. Sci. USA, 96:4325–4329.
Degols et al. (1989), "Antiviral Activity and Possible Mechanisms of Action of Oligonucleotides–poly (L–lysine) Conjugates Targeted to Vesicular Stomatitis Virus mRNA and Genomic RNA," Nucleic Acids Res., 17: 9341–9350.
Derossi et al., (1996), "Cell Internalization of the Third Helix of the Antennapedia Homeodomain is Receptor–Independent," J. Biol. Chem., 271, 18188–18193.
Dingwall, C. and Laskey, R. (1992), "The Nuclear Membrane," Science, 258, 942–947.
Felgner et al., (1987), "Lipofection: A Highly Efficient, Lipid–Mediated DNA–Transfection Procedure," Proc. Natl. Acad. Sci. USA, 84, 7413–7417.
Freed et al. (1990), "Characterization of the Fusion Domain of the Human Immunodeficiency Virus Type 1 Envelope Glycoprotein gp41," Proc. Natl. Acad. Sci. USA, 87, 4650–4654.

(List continued on next page.)

Primary Examiner—Robert A. Wax
(74) Attorney, Agent, or Firm—BioTechnology Law Group; Daniel M. Chambers; Edward O. Kreusser

(57) ABSTRACT

Peptides that are useful as transfection agents are described. The peptides can facilitate the efficient cellular internalization of a broad range and size of compounds that when non-covalently complexed therewith are efficiently internalized into a cell. Advantages include but are not limited to excellent transfection efficiency, relatively low toxicity, internalization by a broad host cell spectrum, and the simplicity and cost-effectiveness that arise from not having to covalently complex the peptide with a specific molecule to be delivered. Applications include but are not limited to the delivery of diagnostics and therapeutics, as well as drug discovery, gene discovery, and the analysis and/or manipulation of other cellular and molecular biological functions. Claims are made for transfection agents, compositions of matter, including pharmaceutical compositions, reagent kits, methods of delivery, and methods of identification of additional peptides for performing and/or including in the same.

119 Claims, 26 Drawing Sheets

OTHER PUBLICATIONS

Gallaher, W.R. (1987), "Detection of a Fusion Peptide Sequence in the Transmembrane Protein of Human Immunodeficiency Virus," Cell, 50, 327–328.

Goldfarb et al., (1986), "Synthetic Peptides as Nuclear Localization Signals," Nature (London), 322, 641–644.

Gottschalk et al. (1996), "A Novel DNA–peptide Complex for Efficient Gene Transfer and Expression in Mammalian Cells," Gene Ther., 3, 448–457.

Haensler and Szoka (1993), "Polyamidoamine Cascade Polymers Mediate Efficient Transfection of Cells in Culture," Bioconjugate Chem., 4, 372–379.

Harris, J.D. and Lemoine, N.R. (1996), "Strategies for Targeted Gene Therapy," Trends Genet., 12, 400–405.

Kalderon et al., (1984), "Sequence Requirements for Nuclear Location of Simian Virus 40 Large–T Antigen," Nature (London), 311, 33–38.

Lewis et al. (1996), "A Serum–Resistant Cytofectin for Cellular Delivery of Antisense Oligodeoxynucleotides and Plasmid DNA," Proc. Natl Acad. Sci. USA, 93, 3176–3181.

Méry et al. (1993), "Disulfide Linkage to Polyacrylic Resin for Automated Fmoc Peptide Synthesis," Int. J. Peptide Prot. Res., 42, 44–52.

Morris et al. (1997), "A New Peptide Vector for Efficient Delivery of Oligonucleotides into Mammalian Cells," Nucleic Acids Res., 25, 2730–2736.

Morris et al. (1999), "A Novel Potent Strategy for Gene Delivery Using a Single Peptide Vector as a Carrier," Nucleic Acids Res., 27, 3510–3517.

Morris et al. (1999), "A New Potent HIV–1 Reverse Transcriptase Inhibitor," J. Biol. Chem., 274, 24941–24946.

Morris et al. (2000), "Translocating Peptides and Proteins and Their Use for Gene Delivery," Curr. Opinion in Biotech., 11, 461–466.

Morris et al. (2000), "An Essential Phosphorylation–site Domain of Human cdc25C Interacts with Both 14–3–3 and Cyclins," J. Biol. Chem., 275:28849–28857.

Morris et al. (2001), "A Peptide Carrier for the Delivery of Biologically Active Proteins Into Mammalian Cells," Nature Biotech. 19, 1173–1176.

Niidome et al. (1997), "Binding of Cationic a–Helical Peptides to Plasmid DNA and Their Gene Transfer Abilities Into Cells," J. Biol. Cham., 272, 15307–15312.

Pasqualini and Ruoshlahtl (1996), "Organ Targeting In Vivo Using Phage Display Peptide Libraries," Nature 380:364–366 (1999).

Phelan et al. (1998), "Intercellular Delivery of Functional p53 by the Herpesvirus Protein VP22," Nat. Biotechnol., 16:440–443.

Prabhakaran, "The Distribution of Physical, Chemical, and Conformational Properties in Signal and Nascent Peptides," Biochem. J. (1990) 269:691–696.

Pichon et al. (1997), "Intracellular Routing and Inhibitory Activity of Oligonucleopeptides Containing a KDEL Motif," Mol. Pharmacol., 51, 431–438.

Plank et al. (1994), "The Influence of Endosome–Disruptive Peptides on Gene Transfer Using Synthetic Virus–like Gene Transfer Systems," J. Biol. Chem., 269, 12918–12924.

Sheldon et al. (1995), "Loligomers: Design of de novo Peptide–based Intracellular Vehicles," Proc. Natl. Acad. Sci. USA, 92, 2056–2060.

Van Mau et al. (1999), "Lipid–Induced Organization of a Primary Amphipathic Peptide: A Coupled AFM–Monolayer Study," J. Membrane Biol., 167, 241–249.

Vidal et al. (1997), "Efficient RNA Delivery into Non–transformed Mammalian Cells by Using a Peptide Vector," Comptes Rendus Acad. Sci. Paris, 320, 279–287.

Vidal et al. (1997), "Conformations of a Synthetic Peptide Which Facilitates the Cellular Delivery of Nucleic Acids," Lett. Peptide Sci., 4, 227–230.

Vidal et al. (1998), "Interactions of Primary Amphipathic Vector Peptides with Membranes—Conformational Consequences and Influence on Cellular Localization," J. Membrane Biol., 162, 259–264.

Vives et al. (1997), "A Truncated HIV–1 Tat Protein Basic Domain Rapidly Translocates through the Plasma Membrane and Accumulates in the Cell Nucleus," J. Biol. Chem., 272, 16010–16017.

Wagner et al. (1992), "Influenza Virus Hemagglutinin HA–2 N–Terminal Fusogenic Peptides Augment Gene Transfer by Transferrin–polylysine–DNA Complexes: Toward a Synthetic Virus–like Gene–Transfer Vehicle," Proc. Natl. Acad. Sci. USA, 89, 7934–7938.

Wyman et al. (1997), "Design, Synthesis, and Characterization of a Cationic Peptide that Binds to Nucleic Acids and Permeabilizes Bilayers," Biochemistry, 36, 3008–3017.

SEQUENCE LISTING

<160> NUMBER OF SEQ ID NOS: 43

<210> SEQ ID NO 1
<211> LENGTH: 21

<212> TYPE: PRT
<213> ORGANISM: Artificial Sequence
<220> FEATURE:
<223> OTHER INFORMATION: Synthetic sequence

<400> SEQUENCE: 1

Tyr Gly Phe Lys Lys Arg Arg Trp Ser Gln Pro Lys Glu Thr Trp Glu
1               5                   10                  15

Thr Trp Trp Thr Glu
            20

<210> SEQ ID NO 2
<211> LENGTH: 18
<212> TYPE: PRT
<213> ORGANISM: Artificial Sequence
<220> FEATURE:
<223> OTHER INFORMATION: Synthetic sequence

<400> SEQUENCE: 2

Tyr Gly Phe Lys Lys Arg Arg Gln Pro Thr Trp Trp Glu Thr Trp Trp
1               5                   10                  15

Thr Glu

<210> SEQ ID NO 3
<211> LENGTH: 17
<212> TYPE: PRT
<213> ORGANISM: Artificial Sequence
<220> FEATURE:
<223> OTHER INFORMATION: Synthetic sequence

<400> SEQUENCE: 3

Tyr Gly Phe Lys Lys Arg Arg Gln Thr Trp Trp Glu Thr Trp Trp Thr
1               5                   10                  15

Glu

<210> SEQ ID NO 4
<211> LENGTH: 19
<212> TYPE: PRT
<213> ORGANISM: Artificial Sequence
<220> FEATURE:
<223> OTHER INFORMATION: Synthetic sequence

<400> SEQUENCE: 4

Tyr Gly Phe Lys Lys Phe Arg Lys Pro Trp Thr Trp Glu Thr
1               5                   10                  15

Trp Thr Glu

<210> SEQ ID NO 5
<211> LENGTH: 19
<212> TYPE: PRT
<213> ORGANISM: Artificial Sequence
<220> FEATURE:
<223> OTHER INFORMATION: Synthetic sequence

<400> SEQUENCE: 5

Tyr Gly Phe Lys Lys Phe Arg Lys Pro Trp Thr Trp Glu Thr Trp
1               5                   10                  15

Trp Thr Glu

<210> SEQ ID NO 6
<211> LENGTH: 19
<212> TYPE: PRT
<213> ORGANISM: Artificial Sequence
<220> FEATURE:

<223> OTHER INFORMATION: Synthetic sequence

<400> SEQUENCE: 6

Lys Lys Lys Arg Lys Val Lys Pro Glu Thr Trp Trp Glu Thr Trp Trp
1               5                   10                  15

Glu Thr Val

<210> SEQ ID NO 7
<211> LENGTH: 21
<212> TYPE: PRT
<213> ORGANISM: Artificial Sequence
<220> FEATURE:
<223> OTHER INFORMATION: Synthetic sequence

<400> SEQUENCE: 7

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic sequence

<400> SEQUENCE: 8

Lys Glu Thr Trp Trp Glu Thr Trp Trp Thr Glu Trp Ser Gln Pro Lys
1               5                   10                  15

Lys Arg Lys Val
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic sequence

<400> SEQUENCE: 9

Lys Glu Thr Trp Trp Glu Thr Trp Trp Thr Glu Ala Ser Gln Pro Lys
1               5                   10                  15

Lys Arg Lys Val
            20

<210> SEQ ID NO 10
<211> LENGTH: 21
<212> TYPE: PRT
<213> ORGANISM: Artificial Sequence
<220> FEATURE:
<223> OTHER INFORMATION: Synthetic sequence

<400> SEQUENCE: 10

Lys Glu Thr Trp Trp Glu Thr Trp Trp Glu Thr Trp Ser Gln Pro Lys
1               5                   10                  15

Lys Lys Arg Lys Val
            20

<210> SEQ ID NO 11
<211> LENGTH: 19
<212> TYPE: PRT
<213> ORGANISM: Artificial Sequence
<220> FEATURE:

<223> OTHER INFORMATION: Synthetic sequence

<400> SEQUENCE: 11

Lys Glu Thr Trp Trp Glu Thr Trp Thr Trp Ser Gln Pro Lys Lys
1               5                   10                  15

Arg Lys Val

<210> SEQ ID NO 12
<211> LENGTH: 19
<212> TYPE: PRT
<213> ORGANISM: Artificial Sequence
<220> FEATURE:
<223> OTHER INFORMATION: Synthetic sequence

<400> SEQUENCE: 12

Lys Trp Trp Glu Thr Trp Trp Glu Thr Trp Ser Gln Pro Lys Lys
1               5                   10                  15

Arg Lys Val

<210> SEQ ID NO 13
<211> LENGTH: 23
<212> TYPE: PRT
<213> ORGANISM: Artificial Sequence
<220> FEATURE:
<223> OTHER INFORMATION: Synthetic sequence
<221> NAME/KEY: MISC_FEATURE
<222> LOCATION: (1)..(1)
<223> OTHER INFORMATION: X can be any amino acid or no amino acid
<221> NAME/KEY: MISC_FEATURE
<222> LOCATION: (2)..(2)
<223> OTHER INFORMATION: X can be any amino acid or no amino acid
<221> NAME/KEY: MISC_FEATURE
<222> LOCATION: (3)..(3)
<223> OTHER INFORMATION: X can be any amino acid or no amino acid
<221> NAME/KEY: MISC_FEATURE
<222> LOCATION: (8)..(8)
<223> OTHER INFORMATION: X can be any amino acid or no amino acid
<221> NAME/KEY: MISC_FEATURE
<222> LOCATION: (9)..(9)
<223> OTHER INFORMATION: X can be any amino acid or no amino acid
<221> NAME/KEY: MISC_FEATURE
<222> LOCATION: (10)..(10)
<223> OTHER INFORMATION: X can be any amino acid or no amino acid
<221> NAME/KEY: MISC_FEATURE
<222> LOCATION: (11)..(11)
<223> OTHER INFORMATION: X can be any amino acid or no amino acid
<221> NAME/KEY: MISC_FEATURE
<222> LOCATION: (12)..(12)
<223> OTHER INFORMATION: X can be any amino acid or no amino acid
<221> NAME/KEY: MISC_FEATURE
<222> LOCATION: (13)..(13)
<223> OTHER INFORMATION: X can be any amino acid or no amino acid
<221> NAME/KEY: MISC_FEATURE
<222> LOCATION: (16)..(16)
<223> OTHER INFORMATION: X can be any amino acid or no amino acid
<221> NAME/KEY: MISC_FEATURE
<222> LOCATION: (21)..(21)
<223> OTHER INFORMATION: X can be any amino acid or no amino acid
<221> NAME/KEY: MISC_FEATURE
<222> LOCATION: (22)..(22)
<223> OTHER INFORMATION: X can be any amino acid or no amino acid
<221> NAME/KEY: MISC_FEATURE
<222> LOCATION: (23)..(23)
<223> OTHER INFORMATION: X can be any amino acid or no amino acid

<400> SEQUENCE: 13

Xaa Xaa Xaa Lys Lys Arg Arg Xaa Xaa Xaa Xaa Xaa Xaa Thr Trp Xaa
1               5                   10                  15

Glu Thr Trp Trp Xaa Xaa Xaa
            20

```
<210> SEQ ID NO 14
<211> LENGTH: 22
<212> TYPE: PRT
<213> ORGANISM: Artificial Sequence
<220> FEATURE:
<223> OTHER INFORMATION: Synthetic sequence
<221> NAME/KEY: MISC_FEATURE
<222> LOCATION: (8)..(8)
<223> OTHER INFORMATION: X can be any amino acid or no amino acid
<221> NAME/KEY: MISC_FEATURE
<222> LOCATION: (9)..(9)
<223> OTHER INFORMATION: X can be any amino acid or no amino acid
<221> NAME/KEY: MISC_FEATURE
<222> LOCATION: (11)..(11)
<223> OTHER INFORMATION: X can be any amino acid or no amino acid
<221> NAME/KEY: MISC_FEATURE
<222> LOCATION: (12)..(12)
<223> OTHER INFORMATION: X can be any amino acid or no amino acid
<221> NAME/KEY: MISC_FEATURE
<222> LOCATION: (13)..(13)
<223> OTHER INFORMATION: X can be any amino acid or no amino acid
<221> NAME/KEY: MISC_FEATURE
<222> LOCATION: (16)..(16)
<223> OTHER INFORMATION: X can be any amino acid or no amino acid

<400> SEQUENCE: 14

Tyr Gly Phe Lys Lys Arg Arg Xaa Xaa Gln Xaa Xaa Xaa Thr Trp Xaa
1               5                   10                  15

Glu Thr Trp Trp Thr Glu
            20

<210> SEQ ID NO 15
<211> LENGTH: 21
<212> TYPE: PRT
<213> ORGANISM: Artificial Sequence
<220> FEATURE:
<223> OTHER INFORMATION: Synthetic sequence
<221> NAME/KEY: MISC_FEATURE
<222> LOCATION: (2)..(2)
<223> OTHER INFORMATION: X can be any amino acid or no amino acid
<221> NAME/KEY: MISC_FEATURE
<222> LOCATION: (3)..(3)
<223> OTHER INFORMATION: X can be any amino acid or no amino acid
<221> NAME/KEY: MISC_FEATURE
<222> LOCATION: (10)..(10)
<223> OTHER INFORMATION: X can be any amino acid or no amino acid
<221> NAME/KEY: MISC_FEATURE
<222> LOCATION: (11)..(11)
<223> OTHER INFORMATION: X can be any amino acid or no amino acid
<221> NAME/KEY: MISC_FEATURE
<222> LOCATION: (12)..(12)
<223> OTHER INFORMATION: X can be any amino acid or no amino acid
<221> NAME/KEY: MISC_FEATURE
<222> LOCATION: (18)..(18)
<223> OTHER INFORMATION: X can be any amino acid or no amino acid
<221> NAME/KEY: MISC_FEATURE
<222> LOCATION: (21)..(21)
<223> OTHER INFORMATION: X can be any amino acid or no amino acid

<400> SEQUENCE: 15

Lys Xaa Xaa Trp Trp Glu Thr Trp Trp Xaa Xaa Xaa Ser Gln Pro Lys
1               5                   10                  15

Lys Xaa Arg Lys Xaa
            20

<210> SEQ ID NO 16
<211> LENGTH: 21
<212> TYPE: PRT
<213> ORGANISM: Artificial Sequence
<220> FEATURE:
<223> OTHER INFORMATION: Synthetic sequence
<221> NAME/KEY: MISC_FEATURE
```

-continued

```
<222> LOCATION: (10)..(10)
<223> OTHER INFORMATION: X can be any amino acid or no amino acid
<221> NAME/KEY: MISC_FEATURE
<222> LOCATION: (11)..(11)
<223> OTHER INFORMATION: X can be any amino acid or no amino acid

<400> SEQUENCE: 16

Lys Glu Thr Trp Trp Glu Thr Trp Trp Xaa Xaa Trp Ser Gln Pro Lys
1               5                   10                  15

Lys Lys Arg Lys Val
            20

<210> SEQ ID NO 17
<211> LENGTH: 20
<212> TYPE: PRT
<213> ORGANISM: Artificial Sequence
<220> FEATURE:
<223> OTHER INFORMATION: Synthetic sequence
<221> NAME/KEY: MISC_FEATURE
<222> LOCATION: (6)..(6)
<223> OTHER INFORMATION: X can be any amino acid or no amino acid
<221> NAME/KEY: MISC_FEATURE
<222> LOCATION: (20)..(20)
<223> OTHER INFORMATION: X can be any amino acid or no amino acid

<400> SEQUENCE: 17

Tyr Gly Phe Lys Lys Xaa Arg Arg Pro Trp Thr Trp Trp Glu Thr Trp
1               5                   10                  15

Trp Thr Glu Xaa
            20

<210> SEQ ID NO 18
<211> LENGTH: 5
<212> TYPE: PRT
<213> ORGANISM: Artificial Sequence
<220> FEATURE:
<223> OTHER INFORMATION: Synthetic sequence
<221> NAME/KEY: MISC_FEATURE
<222> LOCATION: (3)..(3)
<223> OTHER INFORMATION: X can be any amino acid or no amino acid
<221> NAME/KEY: MISC_FEATURE
<222> LOCATION: (4)..(4)
<223> OTHER INFORMATION: X can be any amino acid or no amino acid

<400> SEQUENCE: 18

Trp Trp Xaa Xaa Trp
1               5

<210> SEQ ID NO 19
<211> LENGTH: 27
<212> TYPE: PRT
<213> ORGANISM: Artificial Sequence
<220> FEATURE:
<223> OTHER INFORMATION: Synthetic sequence

<400> SEQUENCE: 19

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 20
<211> LENGTH: 34
<212> TYPE: DNA
<213> ORGANISM: Artificial Sequence
<220> FEATURE:
<223> OTHER INFORMATION: Synthetic sequence
```

```
<400> SEQUENCE: 20
cgggatcccg atgtctacgg aactcttctc atcc                                    34

<210> SEQ ID NO 21
<211> LENGTH: 34
<212> TYPE: DNA
<213> ORGANISM: Artificial Sequence
<220> FEATURE:
<223> OTHER INFORMATION: Synthetic sequence

<400> SEQUENCE: 21
ccccatgggg tcatgggctc atgtccttca ccag                                    34

<210> SEQ ID NO 22
<211> LENGTH: 17
<212> TYPE: PRT
<213> ORGANISM: Artificial Sequence
<220> FEATURE:
<223> OTHER INFORMATION: Synthetic sequence

<400> SEQUENCE: 22

Met Gly Leu Gly Leu His Leu Leu Val Leu Ala Ala Ala Leu Gln Gly
1               5                   10                  15

Ala

<210> SEQ ID NO 23
<211> LENGTH: 7
<212> TYPE: PRT
<213> ORGANISM: Artificial Sequence
<220> FEATURE:
<223> OTHER INFORMATION: Synthetic sequence

<400> SEQUENCE: 23

Pro Lys Lys Lys Arg Lys Val
1               5

<210> SEQ ID NO 24
<211> LENGTH: 4
<212> TYPE: PRT
<213> ORGANISM: Artificial Sequence
<220> FEATURE:
<223> OTHER INFORMATION: Synthetic sequence

<400> SEQUENCE: 24

Trp Ser Gln Pro
1

<210> SEQ ID NO 25
<211> LENGTH: 27
<212> TYPE: PRT
<213> ORGANISM: Artificial Sequence
<220> FEATURE:
<223> OTHER INFORMATION: Synthetic sequence

<400> SEQUENCE: 25

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 26
<211> LENGTH: 23
<212> TYPE: PRT
<213> ORGANISM: Artificial Sequence
<220> FEATURE:
```

-continued

<223> OTHER INFORMATION: Synthetic sequence

<400> SEQUENCE: 26

Met Gly Leu Gly Leu His Leu Leu Val Leu Ala Ala Ala Leu Gln Gly
1               5                   10                  15

Ala Lys Lys Lys Arg Lys Val
            20

<210> SEQ ID NO 27
<211> LENGTH: 27
<212> TYPE: PRT
<213> ORGANISM: Artificial Sequence
<220> FEATURE:
<223> OTHER INFORMATION: Synthetic sequence

<400> SEQUENCE: 27

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 28
<211> LENGTH: 24
<212> TYPE: PRT
<213> ORGANISM: Artificial Sequence
<220> FEATURE:
<223> OTHER INFORMATION: Synthetic sequence

<400> SEQUENCE: 28

Gly Ala Leu Phe Leu Gly Trp Leu Gly Ala Ala Gly Ser Thr Met Gly
1               5                   10                  15

Ala Arg Lys Lys Lys Arg Lys Val
            20

<210> SEQ ID NO 29
<211> LENGTH: 27
<212> TYPE: PRT
<213> ORGANISM: Artificial Sequence
<220> FEATURE:
<223> OTHER INFORMATION: Synthetic sequence

<400> SEQUENCE: 29

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 30
<211> LENGTH: 19
<212> TYPE: DNA
<213> ORGANISM: Artificial Sequence
<220> FEATURE:
<223> OTHER INFORMATION: Synthetic sequence
<221> NAME/KEY: Antisense
<222> LOCATION: (1)..(19)
<223> OTHER INFORMATION: Antisense to HIV TAT

<400> SEQUENCE: 30
ggtcttactc tccgtctct                                          19

<210> SEQ ID NO 31
<211> LENGTH: 26
<212> TYPE: DNA
<213> ORGANISM: Artificial Sequence
<220> FEATURE:

<223> OTHER INFORMATION: Synthetic sequence

<400> SEQUENCE: 31
accagccttc cgatccacca gtcatt                                                26

<210> SEQ ID NO 32
<211> LENGTH: 12
<212> TYPE: PRT
<213> ORGANISM: Artificial Sequence
<220> FEATURE:
<223> OTHER INFORMATION: Synthetic sequence

<400> SEQUENCE: 32

Lys Glu Thr Trp Trp Glu Thr Trp Trp Thr Glu Trp
1               5                   10

<210> SEQ ID NO 33
<211> LENGTH: 6
<212> TYPE: PRT
<213> ORGANISM: Artificial Sequence
<220> FEATURE:
<223> OTHER INFORMATION: Synthetic sequence

<400> SEQUENCE: 33

Lys Lys Lys Arg Lys Val
1               5

<210> SEQ ID NO 34
<211> LENGTH: 10
<212> TYPE: PRT
<213> ORGANISM: Artificial Sequence
<220> FEATURE:
<223> OTHER INFORMATION: Synthetic sequence

<400> SEQUENCE: 34

Tyr Gly Phe Lys Lys Arg Arg Gln Pro Thr
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Synthetic sequence

<400> SEQUENCE: 35

Thr Trp Trp Glu Thr Trp Trp Thr Glu
1               5

<210> SEQ ID NO 36
<211> LENGTH: 21
<212> TYPE: PRT
<213> ORGANISM: Artificial Sequence
<220> FEATURE:
<223> OTHER INFORMATION: Synthetic sequence

<400> SEQUENCE: 36

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 37
<211> LENGTH: 20
<212> TYPE: PRT
<213> ORGANISM: Artificial Sequence

```
<220> FEATURE:
<223> OTHER INFORMATION: Synthetic sequence

<400> SEQUENCE: 37

Lys Glu Thr Trp Trp Glu Thr Trp Trp Glu Thr Trp Ser Gln Lys Lys
1               5                   10                  15

Lys Arg Lys Val
            20

<210> SEQ ID NO 38
<211> LENGTH: 11
<212> TYPE: PRT
<213> ORGANISM: Artificial Sequence
<220> FEATURE:
<223> OTHER INFORMATION: Synthetic sequence

<400> SEQUENCE: 38

Lys Glu Thr Trp Trp Glu Thr Trp Trp Thr Glu
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic sequence

<400> SEQUENCE: 39

Trp Ser Gln Pro Lys Lys Lys Arg Lys Val
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Synthetic sequence

<400> SEQUENCE: 40

Pro Lys Lys Lys Arg Lys Val
1               5

<210> SEQ ID NO 41
<211> LENGTH: 19
<212> TYPE: PRT
<213> ORGANISM: Artificial Sequence
<220> FEATURE:
<223> OTHER INFORMATION: Synthetic sequence

<400> SEQUENCE: 41

Tyr Gly Phe Lys Lys Phe Arg Lys Pro Trp Thr Trp Trp Glu Thr Trp
1               5                   10                  15

Trp Thr Glu

<210> SEQ ID NO 42
<211> LENGTH: 19
<212> TYPE: PRT
<213> ORGANISM: Artificial Sequence
<220> FEATURE:
<223> OTHER INFORMATION: Synthetic sequence

<400> SEQUENCE: 42

Lys Thr Trp Trp Glu Thr Trp Trp Glu Thr Ala Ser Gln Pro Lys Lys
1               5                   10                  15

Arg Lys Val
```

```
<210> SEQ ID NO 43
<211> LENGTH: 19
<212> TYPE: PRT
<213> ORGANISM: Artificial Sequence
<220> FEATURE:
<223> OTHER INFORMATION: Synthetic sequence

<400> SEQUENCE: 43

Lys Thr Trp Trp Glu Thr Trp Trp Glu Thr Trp Ser Gln Pro Lys Lys
1               5                   10                  15

Arg Lys Val
```

PEPTIDE-MEDIATED TRANSFECTION AGENTS AND METHODS OF USE

This application claims priority to U.S. provisional application No. 60/221,932 filed Jul. 31, 2000, which is incorporated herein by reference in its entirety. This application also incorporates by reference PCT application number (to be determined) filed on Jul. 26, 2001, entitled "Peptide-Mediated Delivery of Molecules into Cells" naming Divita et al. as inventors.

TECHNICAL FIELD

The field of the invention is the transfection of cells and the delivery of compounds into cells, including the field of drug delivery.

BACKGROUND OF THE INVENTION

The following description includes information that may be useful in understanding the present invention. It is not an admission that any of the information provided herein is prior art, or relevant, to the presently claimed inventions, or that any publication specifically or implicitly referenced is prior art. This application relates to peptide-based transfection vectors and research, diagnostic, medical, therapeutic, and cosmetic uses thereof.

A significant limitation for cellular research, and particularly medicine in the development of many therapeutic drugs, is the poor permeability of the cell membrane to outside agents. Efficient cellular uptake of many chemical agents is still a challenge. Several approaches have been tried, but all have limitations. One approach has made use of synthetic vectors derived from lipids such as liposomes (see, e.g., Leserman et al. (1980) Nature (London) 288, 602; Machy and Leserman, (1983), Biochim. Biophys. Acta, 730, 313), cationic lipids (see, e.g., Felgner et al., (1987) Proc. Natl. Acad. Sci. USA, 84, 7413; Behr et al. (1989) Proc. Natl. Acad. Sci. USA, 86, 6982; Demeneix et al. (1991) Int. J. Dev. Biol., 35, 481; Labat-Moleur et al. (1996), Gene Ther., 3, 1010; Zhou et al. (1994), Biochim. Biophys. Acta, 1189, 195; Radler et al (1997), Science, 275, 810) and polyethyleleimine (see, e.g., Boussif et al. (1996), Gene Ther., 3, 1074; Boletta et al., (1997), Hum. Gene Ther., 8, 1243). These, while demonstrated to be somewhat effective for the delivery of nucleic acids, have largely not proven successful delivering other types and sizes of compounds. Moreover, they represent foreign entities that will likely cause side effects and cellular toxicity.

Another approach has been the use of viral vectors. Although a powerful technology unto itself, this type of vector can only directly introduce nucleic acids, not proteins. Furthermore, these types of vector present difficulties, or at least apprehension, and hence reluctance, based on concerns of residual pathogenicity that might arise. So far, these safety concerns have yet to be adequately resolved.

Still another approach has been the use of microinjection, but this mechanical procedure is time consuming and not practical from the standpoint of delivery to whole populations of cells, and cells that may already be differentiated, or else in situ deep inside a patient.

More recently, vectors have been described that are based on peptides. However, these approaches are limited since the vectorization process has largely required covalent binding between the vector and the drug, diagnostic, and/or research compound sought to delivered. This applies to virtually all existing peptide strategies, including those employing polylysine (see, e.g., Leonetti et al. (1988), Gene, 72, 323; Degols et al. (1989) Nucleic Acids Res., 19, 945; Lemaitre et al. (1987), Proc. Natl. Acad. Sci. USA, 84, 648; and Degols et al. (1994), Bioconjug. Chem., 5, 8), fusion peptides (see, e.g., Pichon et al. (1997), Mol. Pharmacol., 51, 431; and Bongartz et al. (1994), Nucleic Acids Res., 22, 4681), peptides issued from the homeodomain of *antennapedia* (see, e.g., Derossi et al., (1996), J. Biol. Chem., 271, 18188; and Brugidou et al. (1995), Biochem. Biophys. Res. Commun., 214, 685) and short peptides such as KDEL (see Arar et al. (1995), Bioconjug. Chem., 6, 573), sequences related to the tat gene of HIV (Vives et al. (1997), J. Biol. Chem., 272, 16010), and more sophisticated "loligomer" peptides that contain a nuclear localization sequence associated with an oligolysine sequence (see Sheldon et al. (1995), Proc. Natl., Acad. Sci. USA, 92, 2056. Another vector has further made use of basic peptides (see, e.g., Niidome et al., H., 1997, J. Biol. Cham., 272, 15307; Haensler et al. (1993), Bioconjugate Chem., 4, 372; and Gottschalk et al. (1996), Gene Therapy, 3, 448). Finally, a short peptide has previously been shown to effectively deliver small oligonucleotides of 18–36 nucleotides in length when non-covalently associated therewith (Morris et al. (1997) Nucleic Acids Res., 25, 2730). Most, if not all, of these existing techniques are further limited by a lack of delivery efficiency, especially for large macromolecules, and further yet from compromised biological activity due to serum or medium sensitivity and cytotoxicity.

Thus alternative delivery schemes would be welcome, especially those that overcome one or more of the above noted deficiencies in the art. An ideal agent would have a good delivery efficiency for a broad spectrum of compounds and cell types, and would further have a low toxicity, be easy to handle, and easy to formulate in conjunction with the many different compound types that it can deliver.

SUMMARY OF THE INVENTION

The present invention makes use of the ability of certain small peptides to non-covalently associate with virtually any compound of interest and very efficiently deliver that compound to the inside of a cell. The successful delivery of small compounds, oligonucleotides, larger nucleic acids (including full-length genes), other peptides, and both small and large proteins alike are described herein. Efficiencies are high and toxicity low. Moreover, because the association of the peptide transfection agent and the compound of interest can be non-covalent, the agent may simply be mixed with the desired compound and rapidly delivered, without cumbersome other steps attendant to many other types of vectors. Furthermore, the peptides of the invention are serum-insensitive, which means that they bode particularly well for systemic and/or localized use in patients. Very broad applications, indeed, are thus envisioned and likely for the invention.

Thus, in a first aspect the invention features a peptide transfection agent for assisting in the transport of another compound across a cell membrane, and preferably into a live cell. The peptide is most preferably between about 16 and 30 amino acid residues in length, and contains at least one domain that comprises at least two loci of hydrophobic, preferably aromatic, amino acids.

Besides the domain comprising hydrophobic amino acids, the peptide agent of the invention preferably also contains a hydrophilic domain, preferably one that is cation-rich. Between this hydrophilic domain and the domain comprising aromatic residues may be found a spacer sequence or segment.

In a second aspect, the invention features a composition of matter comprising a peptide or mixture of peptides consisting essentially of one or more members selected from the group comprising SEQ ID NOS. 1, 2, 3, 5, and 6, or variants thereof, e.g., as created or isolated using the formula: Xaa Xaa Xaa Lys Lys Arg Arg Xaa Xaa Xaa Xaa Xaa Xaa Thr Trp Trp Glu Thr Trp Trp Thr Glu Xaa (SEQ ID 13) or any of the subformulas therein, and to the extent such is novel, at least for the claimed uses above.

In a third aspect, the invention features a composition of matter comprising a peptide or mixture of peptides consisting essentially of one or more members selected from the group comprising SEQ ID NOS 7–12, or variants thereof, e.g., as created or isolated using the formula: Lys Xaa Xaa Trp Trp Glu Thr Trp Trp Xaa Xaa Xaa Ser Gln Pro Lys Lys Lys Arg Lys Xaa (SEQ ID NO: 15) or any of the subformulas therein, and to the extent such is novel, at least for the claimed uses above.

In a fourth aspect, the invention features a composition of matter comprising a peptide or mixture of peptides consisting essentially of one or more members selected from the group comprising SEQ ID NO: 4, or variants thereof, e.g., as created or isolated using the formula: Tyr Gly Phe Lys Lys Xaa Arg Arg Pro Trp Thr Trp Trp Glu Thr Trp Trp Thr Glu Xaa (SEQ ID NO: 17).

In another aspect, the invention features a commercial transfection kit comprising at least one transfection agent according to any of the preceding aspect embodiments. The kit may further include one or more components selected from buffer, positive controls, cells to be transfected, phospholipids, and instructions for use. The peptide transfection agent is preferably supplied lyophilized, but may also be supplied in aqueous form.

In still further aspects, the invention features pharmaceutical compositions that are based on the peptide agents of the first aspect and its embodiments. The serum independence, stabilizing influence on complexed compounds, high transfection efficiency, low toxicity, and ease of manufacture make this an ideal "universal" reagent for use in convenient pharmaceutical formulations. Diagnostic compounds and therapeutic compounds alike may be delivered. Administration can be made in vivo, ex vivo, or in situ within a given site of interest in a patient. Preferably, the peptides of the invention are used in conjunction with a therapeutic compound that is effective to treat one or more afflictions, e.g., cancer, inflammation-related conditions, and/or viral-mediated diseases. The compound to be enveloped and/or conjugated with the peptide transfection agent may have virtually any composition or desired effect.

In some preferred embodiments, the pharmaceutical composition functions through stimulation, enhancement, inhibition or disruption of the activity of an enzyme, e.g., modulated by a compound transported using a peptide vector of the invention.

In some other preferred embodiments, the pharmaceutical composition contains, in addition to the peptide vector of the invention, an antisense molecule. This is a nucleic acid that directly or indirectly inhibits translation and/or transcription by binding to a template used therefor. Another example given below demonstrates this specific embodiment and utility.

In a preferred aspect, the invention can be used to deliver at least one compound or substance of interest to target sites via topical application. The invention complexed to one or more compounds or substances can be incorporated in a delivery system such as, but not limited to, a cream, ointment, lotion, spray, tonic or gel. In another preferred aspect, the invention can be used to deliver at least one compound or substance of interest to target sites via injection, infusion, perfusion, or implantation, insertion, or application of a support, gel, time-release capsule or other formulation.

In yet another aspect, the invention features dermatological or cosmetic compositions that are based on the peptide agents of the first aspect and its embodiments. In a further aspect, the invention features a method of delivering a compound to a target cell for the treatment, alleviation, or improvement of dermatological conditions or for cosmetic purposes, using the aspects and embodiments described above.

In a preferred aspect, the invention can be used to deliver a substance or substances of interest to target sites via topical application. The invention complexed to the substance can be incorporated in a delivery system such as, but not limited to, a cream, ointment, lotion, spray, tonic or gel. The substance complexed to the invention can be for therapeutic affects and/or cosmetic enhancement.

In yet a further aspect, the invention features a method of identifying a peptide potentially useful as a transfection agent for the non-covalent association with, and delivery of a compound to a target cell. The method consists of providing as a standard one or more of a peptide and a cationic lipid, each of which is known to be useful as a transfection agent for the non-covalent association with, and delivery of, a compound to a target cell, and comparing the effect of the standard against that of a test peptide, e.g., one per any of the preceding aspect embodiments.

In other aspects, the invention features methods of discovering genes, gene function, and/or drugs using peptides of the invention. Preferably a drug, gene, or function to be screened for has a phenotype associated therewith, e.g., preferably one that can be visualized with or without the assistance of a discriminating or amplifying piece of hardware. In this way, one or more compounds, peptides, proteins, or nucleic acids that exerts a desired effect can be identified and characterized from, e.g., a heterologous library of such compounds and molecules and the particular library member exhibiting the phenotype or effect of interest can be isolated.

Other advantages, aspects, and embodiments will be apparent from the figures, the detailed description, and the claims to follow.

Figure 1:
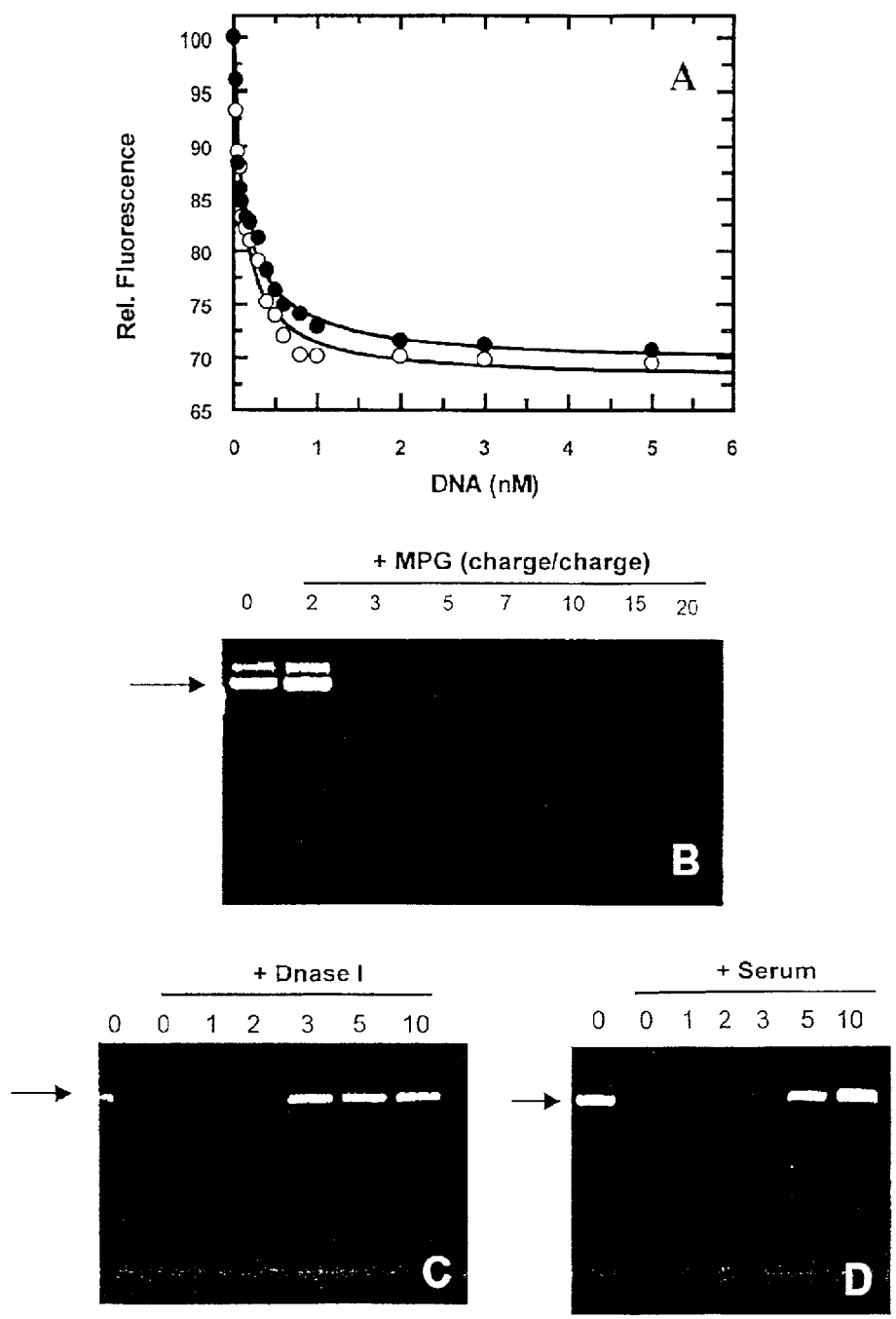
FIG. 1 shows the formation and effect of MPG/DNA complexes via (A) intrinsic fluorescence quenching, (B) a gel-shift assay over varios charge ratios of vector:complexed molecule, (C) DNase I protection assays using the same, and (D) stability against serum.

(A) control cells and (B) p27-treated cells were subjected to cell cycle analysis over a twenty-four hour period.

DETAILED DESCRIPTION OF THE INVENTION

The invention is directed to the use of specialized peptides as transfection agents. These peptides can facilitate the efficient cellular internalization and addressing of a broad range and size of compounds. In most preferred embodiments, the peptides function through a non-covalent complexation with a compound to be delivered. A molar excess of peptide agent relative to the compound to be delivered is typically employed to accomplish this. However, the specific peptides described herein may also find other uses that do not require this, for example, where they are covalently conjugated with the compound to be delivered.

The major barriers to the development of new vectors, especially those that employ peptides or proteins, are poor permeability and selectivity of the cell membrane, coupled with low stability in the cells. Most of the methods proposed so far for gene delivery involve transport of genes of interest into cells and whatever the method used for transfection, is limited by stability, low expression and/or poor efficiency of delivery. In order to overcome these problems, we designed a series of peptide vectors capable of delivering protein into cells rapidly, thus offering the potential to study protein function directly in vivo, and to target specific protein/protein interactions in vivo. These new peptides can also direct nucleic acid transfection. The following discussion focuses on principles that can be used to achieve success with any compound. In fact, peptides of intermediate affinity that can accommodate both proteins and nucleic acids, and/or other types of molecules is also practicable building on principles described herein and previously. See, e.g., Morris et al. (1999) Nucleic Acids Res., 27, 3510–3517.

One of skill will understand that embodiments of the various aspects can cross-apply for the aspects such that combinations not explicitly claimed or mentioned are also permissible and desirable within the scope and spirit of the invention. The scope and spirit is directed to the many advantages of the invention, include the ability to efficiently, conveniently, and safely provide for cellular internalization and intracellular addressing of a broad range and size of compounds. Particular great advantage is afforded in not obligatorily having to covalently affix peptides of the invention with the molecules they serve to deliver to a target cell. Because preferred aspects and embodiments of the instant invention employ non-covalent associations of peptide and a compound to be delivered, transfection is simplified greatly. Equally, if not more important, transfection is improved. Specific advantages include, but are not limited to, excellent transfection efficiencies, relatively low toxicity, and internalization by a broad host cell spectrum. Furthermore, the invention allows for the efficient delivery of large molecules (e.g., antibodies and antibody-dye conjugates exceeding 150 kD) which have been traditionally difficult to administer into a cell using anything other than mechanical means, e.g., microinjection.

I. Peptide Transfection Agents

Peptide or polypeptide transfection agents for assisting the transport of another compound across a cell membrane, and preferably into a live cell, are preferably between about 10 and about 100 amino acid residues in length, more preferably between about 12 and about 60 amino acid residues in length, and most preferably between about 16 and about 30 amino acid residues in length. Embodiments disclosed herein that are most preferred comprise about 19–27 residues, and contain at least a domain that comprises at least two loci of hydrophobic, preferably aromatic, amino acids, hereinafter referred to as the "hydrophobic domain". Preferably, a peptide transfection agent of the present invention comprises a hydrophobic domain, a hydrophilic domain, and a spacer region, such that the spacer region is between the hydrophobic domain and the hydrophilic domain.

The peptide transfection agent may be synthetic in whole or part. Alternatively, or conjunctively, the peptide may constitute a natural sequence or portions thereof. Different segments may be ligated together or else the entire sequence may be synthesized using, e.g. solid phase, liquid phase, or combinational synthesis techniques thereof as known in the art. Alternatively, the entire sequence, whatever the origin, may be introduced in nucleic acid coding and expression form into a bioreactor cell system, e.g., a cell culture or organism, e.g., a plant or yeast, which culture or organism may be grown to produce large scale quantities of the polypeptide. Numerous procedures exist in the art, including classical biochemical techniques, to then isolate or purify the polypeptides for use in the invention. For example, convenient affinity purification tags can be engineered alongside the polypeptide, which tags are then later released if desired by virtue of a proteolytic sequence also engineered nearby. Many commercial sources and kits exist to accomplish this.

Hydrophobic Domain

As used herein, "hydrophobic domain" does not necessarily mean that the domain is hydrophobic overall, or has a particular hydrophobicity index (such as those generated by hydrophobicity scales such as the Kyte-Doolittle scale, (Kyte and Doolittle (1982) J. Mol. Biol. 157: 105–132), but rather a "hydrophobic domain" of a peptide transfection agent of the present invention is a domain that comprises at least two loci of one or more hydrophobic amino acids. The hydrophobic domain is characterized preferably by a plurality of aromatic hydrophobic amino acids, or derivatives or analogs thereof, positioned in at least two loci of the domain. Preferably, the hydrophobic domain of the peptide has at least two aromatic hydrophobic amino acids, more preferably three aromatic amino acids, and most preferably four, five, or more aromatic hydrophobic amino acids. The two or more loci of hydrophobic amino acids are preferably no greater than three amino acid residues apart, and preferably at least two of the hydrophobic amino acids occur side-by-side in a "pair" at a particular locus. Those occurring in pairs and spaced three amino acid residues apart (i.e., having two non-hydrophobic amino acids spaced between the loci of hydrophobic amino acids, or, in other words, separated by two non-hydrophobic amino acids) are predicted to reside on the same side of an alpha helix and may stabilize an alpha helix.

The entire hydrophobic domain of a peptide transfection agent of the present invention can be from four to 40 amino acids in length, but preferably is between about seven and twenty amino acids in length, more preferably between about ten and about sixteen amino acids in length. Preferably the entire hydrophobic domain has at least 3–5 hydrophobic, preferably aromatic, residues, and preferably at least one of the hydrophobic amino acids is tryptophan. Preferably multiple tryptophans are present in the hydrophobic domain and are arranged in at least one pair. Multiple loci, including loci that comprise pairs of hydrophobic amino acids, are preferably separated by hydrophilic amino acids.

In some aspects of the present invention, the hydrophobic amino acids of the hydrophobic domain are preferably arranged such that an alpha-helical structure can be formed under one or more environmental conditions, but this is not a requirement of the present invention. Where the hydrophobic domain of a peptide transfection agent is predicted to form an alpha helix, the hydrophilic amino acids that separate the hydrophobic amino acid loci are predicted to occur on the opposite side of the helix from the hydrophobic amino acids. Most preferably these intervening hydrophilic amino acids between the hydrophobic loci are selected from glutamate (Glu) and threonine (Thr). It is also possible to have conservative substitutions of these residues, such as aspartate (Asp) for glutamate (Glu). It can also be possible to substitute any of several hydrophilic amino acids for Glu and Thr, including charged and uncharged polar amino acids, with the main requirement being that the loci of hydrophobic amino acids are separated by two non-hydrophobic amino acids. Such substitutions can be made and the resulting peptides can be tested for transfection efficiency using the methods described herein (see for example, Examples 3 and 5).

Alpha-helical structures, such as those that can form a hydrophobic domain of a peptide transfection agent of the present invention, have been noted in the literature to be characteristic of a variety of signal peptides. See Prabhakaran, Biochem. J. (1990) 269:691–696 (noting 126 natural sequences). These natural sequences may optionally be selected for use in the invention or new sequences may be created that are optionally modeled thereafter, e,g, that contain various modifications thereover, e.g., amino acid substitutions, insertions, deletions, derivatizations, etc. However, the present invention is in no way limited to peptides having hydrophobic domains modeled after signal peptides or alpha helical structures.

The hydrophobic domain can optionally comprise hydrophilic amino acids in addition to those that occur between loci of hydrophobic amino acids. For example, where the hydrophobic domain occurs at the amino terminus of a peptide transfection agent of the present invention, the hydrophobic domain can comprise N-terminal hydrophilic amino acids. An example of a sequence of hydrophilic amino acids that can occur at the N-terminal portion of an hydrophobic domain that occurs at the N-terminal portion of a peptide transfection agent of the present invention is Lys-Glu-Thr. Such hydrophilic sequences can be of any length, but preferably are from about one to about six amino acids in length, and can promote the solubility of a peptide transfection agent of the present invention. Such a sequence can comprise charged, uncharged polar, and even hydrophobic (aliphatic or aromatic) amino acids, as long as the overall sequence is hydrophilic. Preferably, the N-terminal amino acid of a peptide transfection agent of the present invention is acylated, but this is not a requirement of the present invention.

The hydrophobic domain can optionally comprise additional hydrophobic or hydrophilic amino acids at its C-terminus, particularly where its C terminus is also the C-terminus of the peptide transfection agent. For example, valine (Val) can be added to the C-terminus of a hydrophobic domain. Such additional amino acids can optionally be chosen such that they comprise one or more active or activatable groups or easily derivatized groups for the conjugation of other moieties. Sulfhydryl groups can be useful in promoting the transfection efficiency of peptide transfection agents of the present invention, and can also be added to a peptide transfection agent by adding a chemical group, such as, but not limited to, cysteamine group. An alternative to cysteamide can be the amino acid cysteine (Cys), which can be a C-terminal amino acid, such that its sulfhydryl (—SH) group can optionally be utilized for conjugation to other moieties. Preferably, a linker or derivitizing group such as, but not limited to, a sulfhydryl-containing group or moiety, is positioned at the C-terminus of a peptide transfection agent of the present invention, but that is not a requirement of the present invention.

For example, a linker or derivitizing group such as, but not limited to, a sulfhydryl-containing group or moiety can be positioned at the N-terminus of a peptide transfection agent of the present invention. Similarly, the amino acid cysteine can be positioned at the N-terminus of a peptide transfection agent of the present invention.

Hydrophilic Domain

Besides the hydrophobic domain, the peptide agent of the invention preferably also contains a hydrophilic domain, preferably one that is cation-rich. In preferred embodiments, this hydrophilic domain contains a plurality of basic amino acids, preferably three or more, confined within a segment or span of twelve amino acid residues or less (a "basic cluster"), preferably confined within ten amino acid residues, more preferably within seven amino acids or less.

The hydrophilic domain can be selected from or modeled after a natural nuclear localization signal ("NLS") as known in the art, but this is not a requirement of the present invention. Many such sequences exist and can be used, as one of skill is aware. The hydrophilic domain preferably contains one or more basic, positively charged residues selected from, e.g., lysine, arginine, and histidine. The ability to substitute arginine (Arg) for lysine (Lys) is illustrated in Example 4. Preferably, however, at least one of the positively charged residues is lysine.

The hydrophilic domain can additionally optionally comprise hydrophilic or hydrophobic amino acids in addition to those that occur in the basic cluster. For example, where the hydrophilic domain occurs at the amino terminus of a peptide transfection agent of the present invention, the hydrophobic domain can comprise N-terminal hydrophilic or hydrophobic amino acids. An example of a sequence of amino acids that can occur at the N-terminal portion of a hydrophobic domain that occurs at the N-terminal portion of a peptide transfection agent of the present invention is Tyr-Gly-Phe. A sequence of such additional amino acid sequences can be of any length, but preferably is from about one to about six amino acids in length. Such a sequence can comprise charged, uncharged polar, or hydrophobic (aliphatic or aromatic) amino acids. Preferably, the N-terminal amino acid of a peptide transfection agent of the present invention is acylated, but this is not a requirement of the present invention.

The hydrophobic domain can optionally comprise additional hydrophobic or hydrophilic amino acids at its C-terminus, particularly where its C terminus is also the C-terminus of the peptide transfection agent. For example, valine (Val) can be added to the C-terminus of a hydrophobic domain. Such additional amino acids can optionally be chosen such that they comprise one or more active groups or easily derivatized groups for the conjugation of other moieties. For example, cysteine (Cys) can be a C-terminal amino acid, such that its sulfhydryl (—SH) group can optionally be utilized for conjugation to other moieties. Sulfhydryl groups can be useful in promoting the transfection efficiency of peptide transfection agents of the present invention (see Example 4), and can also be added to a peptide transfection agent by adding a chemical group, such as, but not limited to, cysteamine group that can be conjugated to another moiety to be transfected, or that can be unconjugated.

Spacer Region

Between this hydrophilic domain and the hyrophobic domain may be found a spacer sequence or segment. This spacer is preferably between one and ten amino acid residues in length, and more preferably two to eight residues in length.

This spacer preferably contains one or more amino acid residues known to disrupt or make alpha helices formation difficult, e.g., proline (Pro), glutamine (Gln), glycine (Gly), tyrosine (Tyr), and serine (Ser). Most preferably, the spacer contains at least one glutamine or at least one proline residue. This glutamine or proline residue is most preferably located on the C-terminal end of the spacer sequence. A preferred sequence of amino acids for this domain is the sequence Ser-Gln-Pro, wherein the amino acid immediately preceding the serine (Ser) is a non-charged amino acid.

Preferred Sequences

The following sequences have so far proven most effective in transfecting proteins and chemical compounds:

```
Pep-1:
Tyr Gly Phe Lys Lys Arg Arg Trp Ser Gln Pro Lys Glu Thr Trp Glu Thr Trp Thr Glu    (SEQ ID NO:1)

Pep-1.1:
Tyr Gly Phe Lys Lys Arg Arg Gln Pro Thr Trp Trp Glu Thr Trp Trp Thr Glu            (SEQ ID NO:2)

Pep-1.2:
Tyr Gly Phe Lys Lys Arg Arg Gln Thr Trp Trp Glu Thr Trp Trp Thr Glu                (SEQ ID NO:3)

Pep-3:
Tyr Gly Phe Lys Lys Phe Arg Lys Pro Trp Thr Trp Trp Glu Thr Trp Trp Thr Glu        (SEQ ID NO:4)

Pep-2.6:
```

-continued

```
Lys Lys Lys Arg Lys Val Lys Glu Thr Trp Trp Glu Thr Trp Trp Glu Thr Val          (SEQ ID NO:5)

Pep-2.7:
Lys Lys Lys Arg Lys Val Lys Pro Glu Thr Trp Trp Glu Thr Trp Trp Glu Thr Val      (SEQ ID NO:6)

Pep-2:
Lys Glu Thr Trp Trp Glu Thr Trp Trp Thr Glu Trp Ser Gln Pro Lys Lys Lys Arg Lys Val  (SEQ ID NO:7)

Pep-2.1:
Lys Glu Thr Trp Trp Glu Thr Trp Trp Thr Glu Trp Ser Gln Pro Lys Lys Arg Lys Val  (SEQ ID NO:8)

Pep-2.2:
Lys Glu Thr Trp Trp Glu Thr Trp Trp Thr Glu Ala Ser Gln Pro Lys Lys Arg Lys Val  (SEQ ID NO:9)

Pep-2.3:
Lys Glu Thr Trp Trp Glu Thr Trp Trp Glu Thr Trp Ser Gln Pro Lys Lys Lys Arg Lys Val  (SEQ ID NO:10)

Pep-2.4:
Lys Glu Thr Trp Trp Glu Thr Trp Thr Trp Ser Gln Pro Lys Lys Lys Arg Lys Val      (SEQ ID NO:11)

Pep-2.5:
Lys Trp Trp Glu Thr Trp Trp Glu Thr Trp Ser Gln Pro Lys Lys Lys Arg Lys Val      (SEQ ID NO:12)
```

Based on the success achieved in transfecting cells with small compounds, peptides, and proteins using these peptides, the following generic amino acid sequences are preferred:

Xaa Xaa Xaa Lys Lys Arg Arg Xaa Xaa Xaa Xaa Xaa Xaa Thr Trp Xaa Glu Thr Trp Trp Xaa Xaa Xaa (SEQ ID NO:13), or variants or subformulas therein, particularly variants and subformulas described herein, are preferred, where Xaa can be any amino acid, or can be omitted. Preferably, however, at least one of positions eight through thirteen is a proline (Pro), glutamine (Gln), glycine (Gly), tyrosine (Tyr), or serine (Ser) residue. In addition, preferably Xaa at position sixteen is an aromatic hydrophobic amino acid, most preferably tryptophan (Trp). Also preferably, the Xaa residues at positions 21 and 22 are not omitted, and are preferably hydrophilic amino acids, and most preferably one of the amino acids is glutamate and the other amino acid is threonine, either in the order Glu-Thr or in the order Thr-Glu.

More particularly, the amino acid sequence: Tyr Gly Phe Lys Lys Arg Arg Xaa Xaa Gln Xaa Xaa Xaa Thr Trp Xaa Glu Thr Trp Trp Thr Glu (SEQ ID NO:14) is preferred, or variants or subformulas therein, particularly variants and subformulas described herein, where Xaa can be any amino acid, or can be omitted. Preferably, however, where Xaa of position sixteen is not omitted, it is preferably an aromatic hydrophobic amino acid, most preferably tryptophan (Trp).

Another generic amino acid sequence of the present invention: Lys Xaa Xaa Trp Trp Glu Thr Trp Trp Xaa Xaa Xaa Ser Gln Pro Lys Lys Xaa Arg Lys Xaa (SEQ ID NO:15), or variants or subformulas therein, particularly variants and subformulas described herein, where Xaa can be any amino acid, or can be omitted. It is preferred, however, that in aspects where amino acids in positions two and three are not omitted, they are preferably hydrophilic amino acids. It is also preferably that Xaa residues at positons ten and eleven are not omitted, and are preferably hydrophilic amino acids, and more preferably one of the Xaa's at position ten and eleven is a threonine (Thr) residue and the other of the Xaa's at position ten and eleven is a glutamine (Gln) residue, either in the order Glu-Thr or in the order Thr-Glu. In addition, where the amino acid at position twelve is not omitted, preferably it is a hydrophobic residue, more preferably tryptophan (Trp). Also preferably, the amino acid in position eighteen is omitted or is a basic amino acid, more preferably Xaa at position eighteen is lysine (Lys) or arginine (Arg).

Xaa at position twenty-one is preferably not omitted, and can be any amino acid, but preferably is a valine (Val) residue.

More particularly, the amino acid sequence: Lys Glu Thr Trp Trp Glu Thr Trp Trp Xaa Xaa Trp Ser Gln Pro Lys Lys Lys Arg Lys Val (SEQ ID NO:16), or variants or subformulas therein, particularly variants and subformulas described herein is preferred, where Xaa can be any hydrophilic amino acid. More preferably, one of the Xaa's at position ten and eleven is a threonine (Thr) residue and the other of the Xaa's at position ten and eleven is a glutamine (Gln) residue, either in the order Glu-Thr or in the order Thr-Glu.

Another generic amino acid sequence of the present invention: Tyr Gly Phe Lys Lys Xaa Arg Arg Pro Trp Thr Trp Trp Glu Thr Trp Trp Thr Glu Xaa (SEQ ID NO:17), or variants or subformulas therein, particularly variants and subformulas described herein, where Xaa can be any amino acid, or can be omitted. It is preferred however, that Xaa in position six is a hydrophobic amino acid, more preferably an aromatic hydrophobic amino acid, and that Xaa in position twenty is preferably omitted.

SEQ ID NO:13 is based on Peps-1, -1.1, -1.2, -2.6, and -2.7, peptides efficacious in transfecting peptides and proteins; and SEQ ID NO:14 is based on the subset of Peps-1, -1.1, and -1.2, peptides particularly efficacious in transfecting peptides and proteins. SEQ ID NO:15 is based on Peps-2, -2.1, -2.2, -2.3, -2.4, and -2.5, peptides efficacious in transfecting peptides or proteins and SEQ ID NO:16 is based on the subset of Peps-2, -2.1, and -2.3, peptides particularly efficacious in transfecting peptides and proteins. SEQ ID NO:17 is based on Pep-3, a peptide efficacious in transfecting small compounds.

For all sequences used herein, "Xaa" can be any amino acid or can be omitted, with some constraints that are dependent upon the position of the amino acid in the polypeptide, as described herein. In preferred sequences of the present invention, residues denoted by "Xaa" that occur between or adjacent to hydrophobic loci in the hydrophobic domain are preferably hydrophilic amino acids, preferably uncharged or negatively charged amino acids, e.g., Thr or Glu. In addition, where an amino acid denoted by "Xaa" in the hydrophobic domain is three amino acids away from a hydrophobic locus of the domain, such as just before the spacer region as in SEQ ID NO:13, preferably the amino acid denoted by "Xaa" is a hydrophobic amino acid.

Substitutions, Deletions, and Additional Elements

It will be understood by one of skill that various modifications to the polypeptide transfection agents of the invention may be advantageously implemented, e.g., to increase stability, efficacy, potency of the peptide, or other utility (hence the claim terms "derivative" "analog", and "variant"), (and that the same may apply as well to the molecule types to be delivered). For example, substitutions, insertions, deletions, or derivatizations to the amino acid side groups or the N or C terminus of the overall peptide can be made. For substitutions, amino acids have chiral centers, and the opposite stereoisomer is usually available and may advantageously be substituted. Alternatively, or conjunctively, conservative substitutions may be conveniently introduced provided there is no appreciable compromising effect on the function of one or more of the individual domains or spacer sequences of the peptide, or the overall peptide itself. Various modifications to the individual amino acids can be effected, e.g., either before polypeptide synthesis or after polypeptide synthesis. The efficacy of peptides with sequences that comprise substitutions, insertions, deletions, or derivatizations to the amino acid side groups or the N or C terminus of the overall peptide, or with conservative substitution to any of the amino acids given by the preferred sequences (including the generic sequences) can be tested using methods disclosed herein, including the examples. Conservative substitutions may be defined as exchanges within one of the following five groups:

I. Small, aliphatic, nonpolar or slightly polar residues: Ala, Ser, Thr, Pro, Gly II. Polar, negatively charged residues and their amides: Asp, Asn, Glu, Gln III. Polar, positively charged residues: His, Arg, Lys IV. Large, aliphatic nonpolar residues: Met, Leu, Ile, Val, Cys V. Large aromatic residues: Phe, Try, Trp Within the foregoing groups, the following substitution are considered to be "highly conservative": Asp/Glu, His/Arg/Lys, Phe/Tyr/Trp, and Met/Leu/Ile/Val. Semi-conservative substitutions are defined to be exchanges between two of groups (I)-(IV) above which are limited to supergroup (A), comprising (I), (II), and (III) above, or to supergroup (B), comprising (IV) and (V) above. In addition, where hydrophobic amino acids are specified in the application, they refer to the amino acids Ala, Gly, Pro, Met, Leu, Ile, Val, Cys, Phe, and Trp, whereas hydrophilic amino acids refer to Ser, Thr, Asp, Asn, Glu, Gln, His, Arg, Lys, and Tyr.

At least three hydrophobic, preferably aromatic, amino acids are preferred for the hydrophobic domain and the organization is preferably Trp-Trp-Xaa-Xaa-Trp (SEQ ID NO:18). A preferred alternative is to substitute Phe for Trp. Another substitution that is expected to work is substituting tyrosine (Tyr) for threonine (Thr) in the hydrophobic domain.

Substitutions are not limited to the genetically encoded or even the naturally occurring amino acids. Alternatively, an amino acid, genetically encoded or synthetic, may be modified by reacting it with an organic derivatizing agent that is capable of reacting with selected side chains or terminal residues.

For example, cysteinyl residues most commonly are reacted with alpha-haloacetates (and corresponding amines), such as chloroacetic acid or chloroacetamide, to give carboxylmethyl or carboxyamidomethyl derivatives. Cysteinyl residues also are derivatized by reaction with bromotrifluoroacetone, alpha-bromo-beta-(5-imidazoyl) propionic acid, chloroacetyl phosphate, N-alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino acid-containing residues include imidoesters such as methyl picolinimidate; pyridoxal phosphate; pyridoxal; chloroborohydride; trinitrobenzenesulfonic acid; O-methyliosurea; 2,4-pentanedione; and transaminase-catalyzed reaction with glyoxylate.

Arginyl residues are modified by reaction with one or several conventional reagents, among them phenylglyoxal; 2,3-butanedione; and ninhydrin. Derivatization of arginine residues requires that the reaction be performed in alkaline conditions because of the high pKa of the guanidine functional group. Furthermore, these reagents may react with he groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and e-nitro derivatives, respectively.

Carboxyl side groups (aspartyl or glutamyl) are selectively modified by reaction with carbodiimides (R'N—C—N—R') such as 1-cyclohexyl-3-[2-morpholinyl-(4-ethyl)] carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

If longer sequences are to be fashioned, the preferred addition site is at the N terminus end and just before the linker. However, additional amino acids can also be positioned in the hydrophobic region providing they do not disrupt the spacing between at least two of the hydrophobic loci. For example, additional amino acids can be added at the N-terminal or C-terminal end of the hydrophobic domain. Additional amino acids can also be added to the hydrophilic domain. In some aspects, particularly those in which the peptide transfection agent is designed for drug delivery, additional amino acids can be hydrophobic, and can interrupt the basic cluster (see, for example, SEQ ID NO:4). Where a peptide transfection agent is designed for protein or peptide delivery, however, additional amino acids should not intervene among the basic amino acids of the basic cluster. Additional basic amino acids, such as, but not limited to, Lys and Arg, can be advantageous when included in the basic cluster of the hydrophilic domain. Hydrophilic or hydrophobic amino acids can be added N-terminal or C-terminal to the basic cluster, although preferably negatively charged amino acids are not positioned adjacent to the basic cluster of the hydrophilic domain.

Deletion of amino acid residues of the consensus sequences is also within the scope of the present invention. Particular deletions that can be made in a peptide transfection agent of the present invention include, but are not limited to, deletion of residues (such as Xaa-Xaa-Xaa, or Tyr-Gly-Phe) from the N-terminus, or the deletion of one of the amino acids of the basic cluster (such as Lys), deletion of some amino acids of the spacer region, proving that at least one Pro or at least one Gln is present, and deletion of a hydrophobic residue (such as, but not limited to, Trp) of a hydrophobic locus (see, for example, SEQ ID NO:1). Each of the amino acids denoted by Xaa in SEQ ID NO:13 can, at least in some contexts, be deleted. The efficacy of peptide transfection agents comprising one or more of such deletions is illustrated in Example 4.

The peptide may further contain one or more covalently attached functional groups, preferably attached to either or both of the N and C termini of the polypeptide. These covalently attached groups can include stabilizers, couplers, ligands, enzymatic substrates and/or combinations thereof. Preferred groups include acyl groups on the N terminus and cysteamine (cya) coupling groups on the C terminal end. To the latter may be conveniently attached other chemical moieties, e.g., dyes, ligands, proteins, enzymes, enzymatic substrates, etc. Alternatives to cya are also known to those of skill in the art. For stablizing and/or blocking, e.g., cya may be replaced with an alky group such as methyl or ethyl, which are known to be conveniently positioned onto a —COOH group. Preferably, a linker or derivitizing group such as, but not limited to, a sulfhydryl-containing group or moiety is positioned at the C-terminus of a peptide transfection agent of the present invention, even when it is not coupled to another chemical moiety, but that is not a requirement of the present invention.

Peptides can be synthesized using the framework disclosed herein as a guide, and tested for the ability to transfect cells with nucleic acids, organic and inorganic molecules, peptides, or proteins using methods disclosed in the present application, with particular reference to the examples. (Here and throughout the application, the term "nucleic acids" includes naturally occurring and synthetic nucleic acids, including nucleic acids with non-naturally occurring bases and non-naturally occurring backbones, such as nucleic acids comprising altered sugars, amino acids and amino acid derivatives, or other molecules that can have attached nucleobases and can be linked in a linear fashion, e.g., peptide nucleic acids and related molecules.) For example, in determining the association of peptides with compounds of interest, Examples 1, 2 and 3 disclose gel shift assays, quasielectric light scattering (QSL), tryptophan quenching, and nuclease protection experiments.

Transfection of peptides using transfection agents of the present invention can be determined by using labeled peptides of proteins and detecting them within the cells, or by detecting transfected peptides of proteins with specific binding members such as, but not limited to, antibodies. Detection of the peptides or proteins of interest can also be accomplished through assaying cells treated with the transfection agent and the peptide or protein of interest for an activity that is characteristic of the peptide or protein of interest. The assayed activity can be a direct or indirect effect of the peptide of protein. Such methods are known in the art and are disclosed in Example 3 and Example 5.

Transfection of nucleic acids can be determined by using labeled DNA whose presence can be detected after transfection (for example, DNA labeled with a chromogenic or fluorescent label), or by detection of the nucleic acid with a specific binding member (such as, but not limited to, a nucleic acid probe) after transfection. Transfection of nucleic acids can also be assessed by measuring the activity of a protein the nucleic acid encodes in cells transfected with the nucleic acid using a peptide transfecting agent of the present invention. Such assays can be based on the particular protein the nucleic acid encodes, and many such assays are known in the art. For antisense nucleic acids, altered RNA levels corresponding to the gene the antisense nucleic acid was designed for can be measured, or changes in the activity or amount of proteins encoded by the gene the antisense nucleic acid was designed for can be assayed. Methods of transfecting cells with nucleic acids using a peptide transfection agent and of assaying for the presence of a nucleic acid or its encoded protein in transfected cells are disclosed in Example 1.

The transfection of other compounds of interest in cells treated with peptide transfecting agents of the present invention provided with the compound or compounds of interest can be detected using similar methods, that is, by direct detection of labeled compounds, by indirect detection of labeled compounds, such as by binding of specific binding members or other detection assays, or by activity assays based on known activities of the compound, including its indirect effects on processes that can be assayed. Thus, such assays can be direct or indirect, and examples of such assays are given in Examples 2, 3, and 5.

II. Methods of Using a Peptide Transfection Agent

In especially preferred embodiments, the peptide transfection agent is used to transfect a heterologous compound into a living cell. This compound may be an oligonucleic acid, a nucleic acid, a peptide, a protein, an antibody, an inorganic molecule, another organic molecule, or any derivative or useful combination of these. Peptide nucleic acids (PNAs), including variants of peptide nucleic acids that comprise bonds other than amide bonds, are also contemplated, as are conjugated species. This utility derives from the Applicants' demonstration herein (see examples, below) that molecules as great as 150 kD or larger, e.g., dye-conjugated antibodies, can be efficiently transfected using the peptides and procedure of the invention. There does not appear to be a lower limit to the size of compound that can be transfected, and the upper limit has not yet been determined but is likely to exceed 200 kD, as molecules approximately this large have been demonstrated successful.

The compound to be delivered, as stated, may consist of, at least in part, a dye (i.e., e.g., a cyanine), an antibody, a reporter molecule, e.g., GFP or β-galactosidase, or a molecule that enhances, inhibits, and/or supplements the (in) activity of a cellular or viral polypeptide within a cell. The compound may further be an antisense molecule and have antisense function. Functional assays can be used to monitor effects of compounds delivered into cells by transfection agents of the present invention.

In using the invention, it is not necessary, although often convenient, to derivatize the peptide and/or target compound prior to delivery, e.g., where visualizing agents such as dyes are needed. In addition, the compound of interest may be packaged and intracellularly addressed to a specific site depending on the nature of the specific peptide used and/or the nature of the compound enveloped by the peptide. Of particular merit is the ability of the peptides of the invention to transport whole antibodies, including other chemically conjugated moieties. There further does not appear to be an upper limit to the size or type of macromolecule that can be delivered, which is surprising and unobvious over the prior. Importantly, and again, these entities can also be derivatized, e.g., to other molecular species such as dyes, and without appreciable compromise of delivery.

It should further be noted that in using the above peptides, buffers and water of pH 5.2–7.2 are preferred for greatest solubility effect. Further, to avoid aggregation stock solutions should preferably be stored at 1 mM or lower concentrations.

Most preferably, the peptide transfection agent is used to form a non-covalent complex with a compound or mixture of interest. Preferably the complexation takes place prior to transfection, preferably from 30 seconds to 30 minutes or more in advance. In such noncovalent complexation embodiments, molar ratios of agent:compound are preferably between about 2:1 and 100:1, more preferably between about 5:1 and 30:1, and most preferably about 20:1. Further, working concentrations of about 0.1 uM and 100 uM of peptide are preferred, and more preferably between about 1 uM and 20 uM.

The peptides of the invention have been successfully tested on many different cell types: e.g., bacterial and mammalian, and it is anticipated that any cell type, e.g., plant or yeast are, or can be made, so amenable without undue experimentation and using routine procedures known to those of ordinary skill in the art. For example, those of skill are familiar with plant protoplast techniques that facilitate other transfection methods. The same may be borrowed from for purposes of the instant invention.

The method can utilize any one of a number of assays including but not limited to gel retardation assays, affinity binding assays, quasielectric light scattering, circular dichroism, NMR, fluorescence quenching, FTIR spectroscopy, transfection efficiency into a target cell (whether or not complexed with a compound of interest), addressing ability (e.g. effectiveness of a nuclear localization signal) within a cell, toxicity to a target cell, ability to transport compounds of different size and charge, and ability to adopt a structured conformational state.

The introduction of compounds such as nucleic acid molecules, drugs, peptides, and proteins into cells can be for research, therapeutic, diagnostic, or cosmetic purposes. The introduction of labeled compounds, proteins, and peptides, including, but not limited to, antibodies and antibody fragments, can permit investigation of many cellular processes, of normal and disease-state cells alike, without the introduction of artifacts due to permeabilization of cells and lengthy staining procedures. The compounds introduced can be drugs, peptides, or proteins that can alter one or more cellular or viral functions. The introduction of such compounds can be experimental, for example to elucidate cellular processes or to investigate the properties or activities of the compound that is introduced into the cells. Therapeutic and diagnostic applications are also contemplated, where the introduction of structural proteins, enzymes, transcription factors, co-factors, inhibitors, activators, and the like, into target cells can be efficiently achieved. For example, the methods of the present invention can have therapeutic value for conditions such as, but not limited to, metabolic disorders, genetic diseases or disorders, cancer, inflammation, auto-immune disorders, degenerative disorders (including neurodegenrative disorders), behavioural or psychiatric disorders, and infectious and parasitic diseases, including bacterial and viral infections. Peptide transfection agents of the present invention can deliver drugs, peptides, and proteins to cells that, by virtue of their sequence composition or other features (such as, but not limited to, glycosylation pattern, or affinity for a receptor, transporter, or moiety on an organelle or structure within a cell), can be localized to specific sites within a cell. This can have benefits for experimental studies as well as therapeutic and diagnostic applications.

III. Methods of Discovering Genes, Peptides, or Drugs Using Peptide Transfecting Agents In other aspects, the invention features methods of discovering genes, gene function, peptides, proteins, peptide function, protein function, and/or drugs using polypeptides of the invention. Preferably a drug, peptide, protein, gene, or function to be screened for has a phenotype associated therewith, e.g., preferably one that can be visualized with or without the assistance of a discriminating or amplifying piece of hardware, but this is not a requirement of the present invention. In this vein, mixtures of compounds, e.g., from libraries of heterologous compounds, peptides, proteins, or nucleic acids may be transfected according to the invention and convenient functional assays employed to identify a compound, peptide, protein, or nucleic acid having a feature or effect of interest.

The cellular assays used to determine the activity of a chemical compound, nucleic acid or peptide can any cellular or biochemical assays. For example, cellular and biochemical assays are known that measure secretion, including secretion of particular molecules, such as cytokines, proteases, regulators, etc.; that measure endocytosis or phagocytosis; that measure cell division, apoptosis, cell migration, motility, activation of intracellular signaling pathways, transcriptional activity (for example, using reporter genes such as GFP), translational activity (this also can effectively make use of reporter genes), ion channel activity, metabolic activity, respiratory activity, photosynthetic activity, response to hormones or cytokines, etc. Such assays are well known in the arts of cell biology, biochemistry, and the particular subfields to which they apply. Anti-bacterial, anti-viral, and anti-fungal assays are also well known, and can find use in the methods of the present invention.

A very wide range of potential effects of administered compounds, nucleic acids, or peptides, can be monitored by selecting from cell types or cell lines, optionally transfected with reporter genes or genes that express, for example co-factors, regulators, or co-regulators, or optionally treated with various cytokines, hormones, chemical agents, or optionally provided with various substrata materials, nutrients, co-factors, enzymes, and substrates (including chromogenic or otherwise optically or spectrophotometrically detectable substrates) in the media, any of which can optimize detection of a peptide, drug, or nucleic acid having a feature or activity of interest.

It is also possible to use the methods of the present invention to transfect tissues or whole organisms with libraries of compounds, peptides, or nucleic acids to screen for activities of interest. Such activities can be complex and morphological or physiological, and can include, for example, vasculariztion (or lack thereof), wound healing, reduction of fever, alteration of behavior, reduced tumor size, etc.

For assays using cells, tissues, or organisms, appropriate controls, such as the application of a peptide transfection vector in the absence of a test compound or substance, are performed. Cells, tissues, or organisms that, when assayed, reveal an activity of interest can be used to identify the compound having the activity of interest.

Nucleic Acid Molecules

The present invention includes nucleic acid molecules that comprise sequences that encode peptide transfection agents of the present invention. Such nucleic acid sequences can be DNA or RNA, and can be single-stranded or double-stranded. Such nucleic acid molecules can also comprise additional sequences, including expression elements, origins of replication, restriction enzyme sites, sequences of interest, etc., and can optionally comprise detectable labels (such as, but not limited to, fluorescent or radioactive labels) or specific binding members (such as, but not limited to, biotin). Nucleic acid molecules that encode peptide transfection agents of the present invention can be useful for generating fusions between peptides or proteins of interest and a peptide transfection agent, and as such can be useful in many of the methods and applications.

Nucleic acid molecules that comprise sequences that encode peptide transfection agents of the present invention can be used as primers. In this aspect, the primers preferably comprises sequences that encode peptide transfection agents of the present invention adjacent to at least a portion of a sequence of interest. One or more such primers can be used to amplify a nucleic acid sequence of interest, such as with a polymerase, such as, but not limited to Taq, Pfu, or Tth polymerase, such that the amplification product comprises a nucleic acid sequence of interest fused to a sequence encoding a peptide transfection agent of the present invention. Optionally, at least one primer used in the amplification reactions can comprise a promoter, such as but not limited to, a lac, ara, T3, T7, or SP6 promoter, such that the amplification product can be used for transcription and, subsequently, translation of a sequence of interest fused to a peptide transfection agent of the present invention. In preferred embodiments, a 5' primer used in amplification reactions comprises a promoter, a nucleic acid sequence encoding a peptide transfection agent of the present invention, and a sequence homologous to a sequence of interest, and a 3' primer comprises asequence homologous to a sequence of interest. However, other embodiments are also contemplated, for example, those in which the nucleic acid sequence encoding a peptide transfection agent of the present invention is incorporated into the 3' primer.

The present invention also includes expression constructs that comprise a nucleic acid sequence that encodes a peptide transfection agent of the present invention. Preferably, a construct that comprises a sequence encoding a peptide transfection agent of the present invention also includes at lease one site, such as but not limited to one or more recognition sites for restriction enzymes, one or more recombinase sites (e.g., lox sites or att sites), or other sequences that can allow insertion or addition of nucleic acid sequences of interest. Preferably, the construct is designed such that a reading frame of a sequence of interest can be joined to the reading frame of the peptide transfection agent, such that expression of the construct sequences results in an in-frame fusion between the peptide or protein encoded by the sequence of interest and a peptide transfection agent of the present invention. The construct preferably also includes expression sequences, such as, but not limited to, promoters, enhancers, splice sites, translation initiation or enhancing sequences (such as, but not limited to, Shine-Delgarno sites, Kozak sequences, IRES sequences, and methionine codons), and transcriptional termination sites. Preferably, the construct is a DNA construct that can be transcribed, and the resulting RNA translated, to produce a peptide or protein of interest fused to a peptide transfection agent of the present invention. The construct can be designed for in vivo or in vitro expression, and can be optimized for prokaryotic or eukaryotic expression systems. Expression products that comprise produce a peptide or protein of interest fused to a peptide transfection agent of the present invention can be used in any of the applications provided herein, including research and therapeutic applications.

Libraries

Libraries used in the methods of the present invention can be libraries of chemical compounds. They can be collections of two or more compounds that are known or unknown, such as purified chemicals or crude preparations or extracts or products of a fractionation. Chemical compound libraries can include compounds from more than one source. Chemical compound libraries can also comprise synthetic compounds, optionally be made by combinatorial chemistry methods. Such combinatorial libraries can optionally by ordered based on synthesis steps. Chemical compound libraries from any source can be used to test for drugs. (A "drug", as used herein, is any compound, organic or inorganic, that has biological activity.)

Libraries used in the methods of the present invention can also be nucleic acid libraries, and can be generated by chemical synthesis, by cloning methods as they or known in the art, or by any combination thereof. Synthesis of nucleic acid libraries and their use in screening is well known in the art. Nucleic acid libraries can be antisense libraries, and can be used to test for the activity of antisense nucleic acids designed against one or more regions of one or more genes. In some aspects of the present invention, nucleic acid libraries and in particular antisense libraries, can be used for target validation, that is, as a step toward confirming that disruption of the function of a gene leads to a pathological phenotype, or to the alleviation of a pathological phenotype.

Libraries used in the methods of the present invention can be peptide libraries, using chemically synthesized peptides or peptides synthesized peptides synthesized by in vivo or in vitro translation. In some embodiments of the present invention, it is preferred to generate peptide libraries by, optionally, transcription, and translation or nucleic acid libraries. In this way, after screening the activity of members of the peptide library by transfection into cells, it is possible to identify the peptides of interest (for example, those with desirable activities) by analyzing the nucleic acid library members from which the peptides of interest were derived. Sequencing of the nucleic acids, for example, can be used to derive the amino acid sequences of the peptides of interest. It is also possible to generate peptide libraries by protease digestion of a preparation of one or more proteins that can be known or unknown.

Nucleic acid and peptide libraries can comprise totally random, semi-random, or partially random sequences. Fully random refers to 1) sequences that have been made without statistical weight to the probability of inserting any one of the set of naturally-occurring bases or amino acids at a given position of the random sequence, or 2) sequences that have been made by fragmentation of at least one nucleic acid molecule. Semi-random refers to sequences that have been made with statistical weight as bases/amino acids and/or their sequence and can be made using synthetic methods known in the art or by digesting polypeptides or nucleic acid molecules (see, U.S. Pat. No. 5,270,163 to Gold et al., issued Dec. 14, 1993; and U.S. Pat. No. 5,747,253 to Ecker et al., issued May 5, 1998). Semi-random sequences can be nucleic acid or amino acid sequences that have been synthesized such that particular sequence combinations are preferred over other sequence combinations. For example, a semi-random nucleic acid sequence can be biased to preferentially include only a subset of the nucleic acid codons that encode particular amino acids, or can be biased such that the frequency of stop codons in the sequence is reduced. Similarly, a semi-random nucleic acid or amino acid sequence can be synthesized such that, for example, codons for hydrophobic amino acids, or hydrophobic amino acids themselves, are less abundant in the sequence than would occur if the sequence were totally random. Semi-random sequences can be made by directed chemical synthesis, and can, for example, be based on the synthesis of preferred codons that can be built into a multi-codon sequence as disclosed in PCT application US99/22436 (WO 00/18778) to Lohse et al., published Apr. 6, 2000, which is herein incorporated by reference. Partially random sequences are sequences that are in part known or identified sequences and are in part fully random or partially random sequences, and can also be made by modifying or adding to identified or fixed sequences (Pasqualini and Ruoslahti, Nature 380:364–366 (1999); and U.S. Pat. No. 5,270,163 to Gold et al., issued Dec. 14, 1993).

The use of protein libraries, including antibody libraries, is also contemplated, and can comprise any combination of known or unknown proteins, including proteins generated from mutation (directed or random) of genes that encode them, and proteins having partially known and partially unknown, or randomized, sequences. Protein libraries can be generated by, optionally, transcription, and translation of nucleic acids (that themselves can be from a cellular source, synthetic, generated by recombination, cloning, mutation, or addition to known or unknown nucleic acids that may or may not be from a cellular source, or any combination thereof). In other aspects, protein libraries can be from materials, organisms, cells, or tissues, and can be substantially purified or crude extracts or fractions.

In many instances it can be desirable to construct libraries that are divided into aliquots (pools or "sublibraries"), such that a given pool that reveals activity in a cellular assay can be subdivided and re-tested in cellular assays, until one or more library members can be identified as having the desirable activity.

Complex Mixtures

The methods of the present invention can also be used to test for activities in complex mixtures. As used herein, a complex mixture is a mixture having one or more types of compound, where nucleic acids, peptides, proteins, lipids, carbohydrates, and various types of small organic molecules and inorganic molecules are different types of compounds. The transfection agents of the the present invention are ideally suited to testing for one or more activities in a complex mixture, since they are able to transfect cells with a wide variety of compounds. Such complex mixtures can comprise plant extracts, serum, soil extracts, etc. The complex mixtures can be subjected to a variety of procedures for partial purification and concentration of the components, including centrifugation, dialysis, phase separation, precipitation, chromatography, electrophoresis, etc. In some preferred embodiments, extracts can be tested for cellular activity and then duplicate samples can be subfractionated and retested, etc., until the active compound is identified.

III. Pharmaceutical Compositions/Manufacture of Medicaments

A peptide transfection agent of the present invention, preferably conjugated to or in combination with one or more drugs or therapeutic agents, can be administered to a human patient per se, or in pharmacological compositions where it is mixed with suitable carriers or excipient(s). Techniques for formulation and administration of drugs may be found in "Remington's Pharmaceutical Sciences," Mack Publishing Co., Easton, Pa., latest edition.

A wide range of molecules that can have pharmaceutical or therapeutic effects can be delivered into cells using compositions and methods of the present invention. The molecules can be organic or inorganic. Organic molecules can be peptides, proteins, carbohydrates, lipids, sterols, nucleic acids (including peptide nucleic acids), or any combination thereof. A formulation for delivery into cells can comprise more than one type of molecule, for example, two different DNA sequences, or a protein and a steroid, etc. While recognizing that the peptides of the present invention can deliver a wide range of compounds into cells, it is particulary noteworthy that peptides and proteins, including large proteins, can be delivered.

In many instances, local delivery of a peptide of the present invention complexed with one or more compounds of interest is preferred, as it improves the efficiency of delivery to the target cells, while minimizing side effects that are mediated by nontarget tissues. The compositions of the present invention, being taken up rapidly by cells, have the potential to allow high dosages of therapeutics to be delivered to the site of pathology, with minimal systemic effects.

Such compounds of interest can include, but are not limited to, growth factors, cytokines, enzymes, enzyme inhibitors, or anti-inflammatory peptides such as those that inhibit the affect of, for example, rheumatoid arthritis or other aspects and embodiments described above.

In some preferred aspects, respiratory pathologies, such as asthma, can be treated using compositions of the present invention. Both manual and mechanized inhalation devices are known in respiratory therapy, and can be used to deliver aerosols comprising therapeutic compounds complexed with peptides of the present invention. Candidate molecules that can be delivered for the treatment of asthma include, but are not limited to inhibitors of phosphodiesterase, tyrosine kinases, and NF-kappaB.

Routes of Administration

In other preferred therapeutic embodiments, the molecule to be delivered by the peptide agent is p53, a portion or derivative thereof, a nucleic acid encoding the same, or else another compound that is effective to kill or attenuate the growth of cancer cells. For p53, this tumor suppressor induces apoptosis in cells undergoing DNA damage (Levine (1997) Cell, 88:323–331). Covalent attachment of p53 to other transporting peptides has previously been demonstrated to enter and induce apoptosis in cells (Phelan et al. (1998) Nat. Biotechnol., 16:440–443). There is no reason that a non-covalent technique as described herein will not be at least, if not more, effective. That a native p53, unadulterated by another covalently attached molecule, can be delivered, may have advantage, e.g., fewer side effects. This illustrates another meritorious feature of the invention.

Another example of a therapeutic agent that can be delivered as a chemotherapeutic agent according to the invention is a cyclin-dependent docking site mimic or ligand such as described by Chen et al. (1999) Proc. Natl. Acad. Sci. USA, 96:4325–4329. Cyclin-cDK activity has been implicated in certain cancers. Modulation thereof using the invention in conjunction with the ligand described by Chen et al. can arrest or attenuate such cancers, and even induce apoptosis in such cancer cells.

Suitable routes of administration may, for example, include oral, rectal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer a pharmaceutical composition of the present invention in a local rather than systemic manner, for example, via injection of the pharmaceutical composition directly into a solid tumor, often in a depot or sustained release formulation.

Local delivery can be effected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in losenges for oral, trachial, or esophogal application; can be supplied in liquid, tablet or capsule form for administration to the stomach or intestines, can be supplied in suppository form for rectal or vaginal application; or can even be delivered to the eye by use of creams, drops, or even injection. Formulations containing compositions of the present invention complexed with therapeutic molecules can even be surgically administered, for example in association with a polymer or other structure or substance that can allow the compositions to diffuse from the site of implantation to surrounding cells. Alternatively, they can be applied surgically without the use of polymers or supports.

Of particular interest is the ability to apply formulations comprising compositions of the present invention topically. Formulation that promote penetration of the epidermis are known in pharmacology. Compositions of the present invention can be used to advantage, for example for the delivery of peptides, proteins, and other molecules that curtail pain, iching, or inflammation or that have antiviral, antibacterial, or antifungal effects to the skin.

Composition/Formulation

Pharmacological compositions of the compounds and the physiologically acceptable salts and prodrugs thereof are preferred embodiments of this invention. Pharmacological compositions of the present invention may be manufactured by processes well known in the art; e.g., by means of conventional mixing, dissolving, granulating, dragee-making, levigating, emulsifying, encapsulating, entrapping or lyophilizing processes.

Pharmacological compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

Formulation that promote penetration of the epidermis are known in pharmacology, and can find use in the treatment of many skin conditions, such as, but not limited to, psoriasis and fungal infections. Formulations that promote penetration of the epidermis and underlying layers of skin are also known, and can be used to apply compositions of the present invention to, for example, underlying muscle or joints. In some preferred therapeutic embodiments, formulation comprising compositions of the present invention that deliver compounds for alleviating rheumatoid or osteo-arthritis can be administered by applying a cream, ointment or gel to the skin overlying the affected joint.

Although oral and parenteral administration are not preferred for the invention, such routes may find merit in future applications where the peptide and/or complex is made stable enough to weather the harsh proteolytic environment of the gut. If so, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmacological preparations for oral use can made with the use of a solid excipient, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragée cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmacological compositions which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may taken in the form of tablets or lozenges formulated in conventional manner. For the small peptides and complexes of the invention, this may prove useful.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichloro-tetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compositions may be formulated for parenteral administration by injection, e.g., by bolus injection or continuous infusion. In this way it is also possible to target a particular organ, tissue, tumor site, site of inflammation, etc. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmacological compositions for parenteral administration include aqueous solutions of the compositions in water soluble form. Additionally, suspensions of the compositions may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compositions to allow for the preparation of highly concentrated solutions.

Alternatively, one or more components of the compostion may be in powder form for constitution with a suitable vehicle, e.g., sterile pyrogen-free water, before use.

The compositions may also be formulated in rectal compositions such as suppositories or retention enemas, e.g., containing conventional suppository bases such as cocoa butter or other glycerides.

In addition to the formulations described previously, the compositions may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil), or as part of a solid or semi-solid implant that may or may not be auto-degrading in the body, or ion exchange resins, or one or more components of the composition can be formulated as sparingly soluble derivatives, for example, as a sparingly soluble salt.

The pharmacological compositions herein also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Dosage

Pharmacological compositions suitable for use in the present invention include compositions wherein the active ingredients are contained in an amount effective to achieve its intended purpose. More specifically, a therapeutically effective amount means an amount of compound effective to prevent, alleviate or ameliorate symptoms of disease or prolong the survival of the subject being treated.

Determination of a therapeutically effective amount is within the capability of those skilled in the art, especially in light of the detailed disclosure provided herein.

For any compound used in the methods of the invention, the therapeutically effective amount or dose can be estimated initially from cell culture assays. For example, a dose can be formulated in animal models to achieve a circulating concentration range that includes the $IC_{50}$ as determined in cell culture (where inhibitor molecules are concerned). Such information can be used to more accurately determine useful doses in humans.

Toxicity and therapeutic efficacy of a composition of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage may vary within this range depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

The amount of composition administered will, of course, be dependent on the subject being treated, on the subject's weight, the severity of the affliction, the manner of administration and the judgment of the prescribing physician.

Packaging

A pharmaceutical composition that comprises a peptide transfection agent of the present invention can be supplied such that the peptide transfection agent and one or more active compounds are in the same container, either in solution, in suspension, or in powder form. If provided together, the peptide transfection agent and one or more active compounds can be covalently conjugated, noncovalently complexed, or not conjugated or complexed to one another. The peptide transfection agent can also be provided separately from one or more active compounds, and can be mixed with one or more active compounds prior to administration. Various packaging options are possible, depending at least in part on whether the peptide transfection agent, one or more active compounds, and, optionally, one or more delivery, solubilizing, flavoring, or suspending agents are provided together or separately, and upon the route and mechanism of administration. For example, where the peptide transfection agent is supplied separately from one or more active compounds, the compositions may, if desired, be presented in a pack having more than one chamber, and in which a barrier can be ruptured, ripped, or melted to provide mixing of the peptide transfection agent with the active compound. Alternatively, two separately provided elements can be mixed in a separate container, optionally with the addition of one or more other carriers, solutions, etc. One or more unit dosage forms containing the active ingredient can be provided in a pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, retrovirus-mediate ailments, and the like. Furthermore, the invention is ideally suited to gene therapy, either to deliver (indirectly via gene insertion) a desired protein of interest, or else to supply an antisense molecule to control the expression of a gene of interest.

Dermatological and Cosmetic Compositions

A peptide transfection agent of the present invention, preferably conjugated to or in combination with one or more drugs or therapeutic agents, can be administered for cosmetic purposes. A peptide transfection agent can be mixed with suitable carriers or excipient(s). A wide range of molecules that can have be used for cosmetic purposes can be delivered into cells using compositions and methods of the present invention. The molecules can be organic or inorganic. Organic molecules can be peptides, proteins, carbohydrates, lipids, sterols, nucleic acids (including peptide nucleic acids), or any combination thereof. A formulation for delivery into cells can comprise more than one type of molecule, for example, two different DNA sequences, or a protein and a steroid, etc.

In most cases, dermatological or cosmetic formulations comprising compositions of the present invention can be applied topically. Formulation that promote penetration of the epidermis (the dead outer layer of the skin) are known in pharmacology. In some cases, penetration of the outer layer of the skin can be enhance by chemical or laser "stripping" or "peeling" or microabrasion, techiques that are currently used to remove the outer layer of skin and promote rejuvenation. It is also possible to inject a dermatalogical or cosmetic formlation of the present invention into, or just below, the skin. This can be appropriate when the formulation is to be targeted to a specific site, or effiecient penetration below the dermis is desirable.

Compositions of the present invention can be used to advantage, for example for the delivery of peptides, proteins, and other molecules to live skin cells to promote cosmetic effects. For example, healing of wounds, abrasions, or scars can be promoted by the introduction of cell division promoting agents (for example, cell cycle regulators, transcription factors, or small molecules such as retinoids) to cells at the site of the lesion.

In another aspect, the present invention can provide a safe and beneficial way to achieve "tanned" or pigmented skin. A tanned appearance is highly desirable to many people. Currently, however, tanning requires either exposure to UV light, which is correlated with both skin sarcoma and melanoma, or dying the skin with "self-tanning" lotions that often give the skin an unnatural color, and tend to dye the dead outer layer of skin, which is shed fairly rapidly. Peptide transfection vectors of the present invention can be used to introduce compounds into cells that promote the production of natural melanin by the skin cells. Such compounds could be, for example, transcription factors, or proteins or compounds that activate or induce transcription factors that regulate melanin production. The production of melanin by this means could provide natural coloration without the hazards of UV exposure, while at the same time, by inducing melanin production, providing the benefit of affording some protection against UV.

Other cosmetic aspects are also considered, such as the introduction into skin cells, or cells immediately underlying the skin, of compounds of interest that can reduce or increase oil secretion, or increase the production of collagen or other extracellular matrix molecules to reduce wrinkling or "sagging" of skin, etc.

Cosmetic formulations of the present invention can optionally include penetration agents, can include substances that allow the formulation to be applied evenly to the skin, such as oils, lipids, or polymers that allow for dispersal or "smoothing" of the formulation, can include pigments, can include botancial extracts, can include "moisturizers", sunscreen compounds, acids (such as, but not limited to, alpha-hydroxy or beta-hydroxy acids), chelators, etc.

A dermatological or cosmetic formulation of the present invention can be packaged in any appropriate manner. For example, it can be provided in a package that comprises more than one container, such that the peptide transfection agent can optionally be provided separately from the dermatological or cosmetic compound of interest, and can optionally be mixed with the compound of interest before application. The packaging can optionally facilitate mixing, for example, by allowing the formulations to mix by puncturing, tearing, or melting a barrier between the formulations, or removing a barrier between the formulations by unscrewing, pulling a tab, etc. In addition, additional formulations can be provided separately from the transfection agent and the cmpound of interest, including one or more other other liquids, powders, or lotions that can comprise, for example, sunscreens, penetration agents, salves, or other cosmetics that are to be applied before, after, or at appoximately the same time as the peptide transfection agent and compound of interest. Instructions for administration can be included in the package, or with one or more of the containers.

EXAMPLES

Example 1

Peptide Vector Design and Characterization for Gene Delivery

We previously demonstrated that MPG, derived from the hydrophobic fusion peptide of HIV-1 gp41 and the hydrophilic nuclear localization sequence of the SV40 large T antigen can be used as a powerful tool for the delivery of small oligonucleotides into cultured cells. Morris et al. (1997) Nucleic Acids Res., 25, 2730–2736. Now we surprisingly extend the potential of MPG to the delivery of large nucleic acids in cultured cells. In vitro, MPG interacts strongly with nucleic acids, most likely forming a peptide cage around them, and further stabilizing and protecting them from degradation in cell culture media. MPG is non-cytotoxic, insensitive to serum and efficiently delivers plasmids into several different cell lines in only 1 h. Moreover, MPG enables complete expression of the gene products encoded by the plasmids it delivers into cultured cells. Finally, we have investigated the potential of MPG as an efficient delivery agent for gene therapy by attempting to deliver antisense nucleic acids targeting an essential cell cycle gene. Here we demonstrate this feasibility. MPG efficiently delivered a plasmid expressing the full-length antisense cDNA of human cdc25C, which consequently successfully reduced cdc25C expression levels and promoted a block of cell cycle progression. Based on these results, we conclude that MPG is a potent delivery agent for the generalized delivery of nucleic acids, large (e.g., >36 mers) and small alike, into cultured cells and believe that its contribution to the development of new gene therapy strategies is evident and of prime interest.

Most existing methods of gene delivery involve transport of the gene of interest into cells via the endosomal pathway, which unfortunately leads to its extensive degradation in the acidic lysosomal compartments. In search of novel carriers, research in this field has focused on compounds that are able to perturb or to disrupt the lysosomal membrane and that reduce the degradation of the gene of interest in the lysosome. Several groups have already shown that lysine-rich peptides and cationic peptides, derived from viral proteins which mimic the endosomal disruptive properties of viral particles, penetrate cells and facilitate the delivery of nucleic acids (Wagner et al.(1992) Proc. Natl Acad. Sci. USA, 89, 7934–7938; Gottschalk et al. (1996) Gene Ther., 3, 448–457; Plank et al. (1994) J. Biol. Chem., 269, 12918–12924; Wyman et al. (1997) Biochemistry, 36, 3008–3017; Niidome et al.(1997) J. Biol. Chem., 272, 15307–15312). In addition, cationic peptide synthetics which adopt a structure that potentially allows crossing the liposomal bilayer membranes and then promotes the release of nucleic acids have been proposed (Plank et al. (1994) J. Biol. Chem., 269, 12918–12924; Wyman et al. (1997) Biochemistry, 36, 3008–3017; Niidome et al.(1997) J. Biol. Chem., 272, 15307–15312).

A. Peptide Vector Design and Characterization

The peptide vector MPG: Gly-Ala-Leu-Phe-Leu-Gly-Phe-Leu-Gly-Ala-Ala-Gly-Ser-Thr-Met Gly-Ala-Trp-Ser-Gln-Pro-Lys-Ser-Lys-Arg-Lys-Val (SEQ ID NO:19) was designed so as to satisfy the major requirements for efficient gene delivery, including the ability to cross the cell membrane, the high affinity and specificity for nucleic acids, and a particular selectivity for the nuclear versus cytoplasmic compartment (Vidal et al. (1997) Comptes Rendus Acad. Sci. Paris, 320, 279–287; Morris et al. (1997) Nucleic Acids Res., 25, 2730–2736). As such, the 27-residue MPG peptide was derived from two independent domains: a hydrophobic domain (residues 1–16) issued from the fusion sequence of HIV-1 gp41 (Gallaher, W. R. (1987) Cell, 50, 327–328; Freed et al. (1990) Proc. Natl Acad. Sci. USA, 87, 4650–4654) thought to be required for efficient crossing of the cell membrane, and a hydrophilic domain (residues 20–27) derived from the NLS of SV40 large T antigen, (Dingwall, C. and Laskey, R. (1992) Science, 258, 942–94.), thought to be required for the nuclear addressing of the peptide. MPG is stable and highly soluble in physiological conditions and presents a very versatile structure, an unusual feature which is most likely key for its cellular uptake (Chaloin et al. (1997) Biochemistry, 36, 11179–11187; Vidal et al. (1997) Lett. Peptide Sci., 4, 227–230.). In standard cell culture conditions, MPG localizes rapidly to the nucleus of human HS68, murine NIH 3T3 fibroblasts, and simian kidney SV40 transformed cos-7 (Vidal et al. (1997) Comptes Rendus Acad. Sci. Paris, 320, 279–287).

B. Formation of MPG/DNA Complexes

We investigated to what extent MPG could interact with nucleic acids using the pRL-SV40 plasmid (3.2 kb), which expresses *R.reniformis* luciferase under control of the SV40 enhancer/promoter region (Sherf et al. (1996) Promega Notes, 57, 2–9.), and the pJ3O-antisense-Hucdc25C plasmid (4.9 kb), which encodes the antisense full-length cDNA sequence of human cdc25C under control of an SV40 promoter (Morris, M. C. (1997) Ph.D. Thesis, Montpellier University, Montpellier, France). Three different approaches were used to monitor peptide/DNA interactions: (i) quenching of intrinsic tryptophan fluorescence; (ii) agarose gel-shift assay; (iii) DNase I or serum nuclease protection assays.

MPG contains a single Trp-residue at position 18, located between the NLS and the fusion peptide domains, which constitutes a sensitive probe for monitoring interactions between MPG and nucleic acids (Lewis et al. (1996) Proc. Natl Acad. Sci. USA, 93, 3176–3181; Behr et al. (1989) Proc. Nat Acad. Sci. USA, 86, 6982–6986.). As shown in FIG. 1A, the binding of nucleic acids to MPG induced a marked quenching of the intrinsic fluorescence of MPG with a saturating value of 23%, without modifying the fluorescence maximum emission wavelength (340 nm), which indicates that the Trp residue interacts directly with either the phosphate or the nucleoside moieties of the nucleic acid. It should be noted that in the absence of nucleic acids, the intrinsic fluorescence of MPG varied linearly with its concentration, suggesting that MPG molecules do not self-associate in such conditions. Fitting of the titration binding curves revealed that MPG presented high affinity for both pRL-SV40 and pJ3O-antisense-Hucdc25C, with respective dissociation constant ($K_d$) values of $0.5 \times 10^{-8}$ $M_{-1}$ and $1.8 \times 10^{-8}$ $M_{-1}$, affinity thus correlating inversely with the size of the plasmid. In both cases, saturation occurred at a concentration of DNA 1000-fold lower that of MPG ($1.0 \times 10^{-5}$ M), i.e. at a ratio of peptide per nucleic acid at least 10–20-fold higher than that predicted for achieving charge neutralisation between the NLS moiety of MPG (three Lys and one Arg) and the phosphate groups in nucleic acids.

Similarly to the nature of interactions proposed to occur upon association of lysine-rich peptides with DNA (Harris, J. D. and Lemoine, N. R. (1996) Trends Genet., 12, 400–405), association of MPG with DNA most likely mainly involves electrostatic interactions dependent on the cationic residues in the NLS of MPG. However, as a larger number of MPG peptides than that theoretically required for charge neutralization of bound DNA molecules was actually involved in the formation of the MPG/DNA complex, we hypothesized that additional interactions might take place between peptides, which, as such, most likely formed a 'cage' around the molecule of DNA.

In an attempt to confirm this hypothesis, we investigated the formation of peptide/DNA complexes by monitoring their electrophoretic mobility as a function of the positive (MPG)/negative (DNA) charge ratios (between 0:1 and 15:1) on an agarose gel (1% w/v) stained with ethidium bromide. As shown in FIG. 1B, the electrophoretic mobility of DNA was completely abolished for a charge ratio 3-fold higher than the neutralisation charge ratio (lane 3). The lack of migration suggested the formation of a large complex between MPG and the DNA, in agreement with the results obtained in the fluorescence titration experiments.

We further hypothesized that the formation of a peptide 'cage' around the DNA might prevent its degradation by nucleases. As such, we evaluated the nuclease-protective effect of MPG by incubating complexes of MPG/DNA varying in their charge ratio with DNase I, and analysing the subsequent integrity of DNA on an agarose gel. As shown in FIG. 1C (lane 5), in MPG/DNA complexes with a charge ratio up to 2:1, DNA was subject to complete degradation by DNase I, whereas at higher ratios the concentration of MPG was sufficient to fully protect DNA, in which case the DNA migration band was perfectly detectable. Similar experiments performed with 10% FCS instead of DNase I revealed that DNA was fully degraded in the presence of serum (lane 2) up to a charge ratio of 5:1 (MPG/DNA), required for full protection of the DNA (FIG. 1D, lane 6), instead of 3:1 in the presence of DNase I. The difference observed with nuclease versus serum suggests that in the serum not only nucleases, but also proteases, take part in the degradation process; this difference may, however, also reflect the differential protection of the plasmid to purified DNase I versus to serum nucleases.

Finally, we sought to provide further evidence for the model of the peptide 'cage' of MPG surrounding nucleic acids, using quasielastic light scattering (QELS). The results of our preliminary experiments are in agreement with this model, as they reveal the existence of particles of MPG/DNA with an average diameter of 200–300 nm, detected for a charge ratio of 3:1 (data not shown).

C. MPG Promotes Efficient Delivery and Expression of Nucleic Acids in Different Cell Lines.

We next evaluated the ability of MPG to deliver DNA into different cell lines including HS-68 and NIH 3T3 fibroblasts, C2C12 myoblasts and cos-7 cells using the pRL-SV40 reporter system encoding *R.reniformis* luciferase, and compared the efficiency of transfection with that of the commonly used Lipo-fectamine®-based technique (Flegner et al. (1987) Proc. Natl Acad. Sci. USA, 84, 7413–7417; Felgner et al. (1994) J. Biol. Chem., 269, 2550–2561). pRL-SV40 (0.5 µg) was first incubated with different concentrations of MPG, corresponding to positive (MPG)/negative (DNA) charge ratios from 1:1 to 20:1. Cultured cells ($0.5-1 \times 10^6$) were then overlaid with the preformed MPG/DNA complexes in 500 µl DMEM for 1 h in the presence or absence of FCS. Following this transfection step, fresh DMEM supplemented with serum was added and the expression of luciferase was monitored 24 h later in a luminometric assay. The efficiency of transfection in the absence of serum for different concentrations of MPG, as judged by the expression of luciferase, is reported in FIG. 2. Maximal transfection and expression of luciferase were obtained for a peptide/DNA charge ratio >5:1, corresponding to a concentration of MPG of 0.4 µM, with a specific luciferase activity between 1.9 and 2.42 U/mg of protein for COS-7, NIH 3T3 and HS-68 cell lines. Once again, these results are consistent with the model of a peptide 'cage' surrounding the DNA molecule being required for its efficient transfection. In the case of C2C12 cells, maximal transfection was obtained for a charge ratio of 15:1, which corresponds to a peptide concentration of 1.2 µM, with a specific luciferase activity of 1.6 U/mg of protein.

The degree of transfection using MPG was at least twice and seven times higher than that obtained with Lipofectamine® for fibroblasts or COS-7 and C2C12 myoblasts, respectively. These transfection data with MPG reveal that the preformed MPG/DNA complex is efficiently driven into the cytoplasm of cells and that the presence of MPG molecules around the DNA does not modify the potential of its gene product to be expressed. As a control, we verified that in the absence of MPG no transfer of DNA occurred, confirming that free DNA cannot cross the cell membrane alone and that it is most likely rapidly degraded in the presence of serum, as already described in FIG. 1D.

Finally, we evaluated the impact of serum in the cell culture medium on the efficiency of transfection of MPG. Experiments with an MPG/DNA charge ratio of 10:1 were performed in the presence of 10% FCS, a concentration commonly used in cell culture. The efficiency of MPG remained insensitive to this percentage of serum in HS-68 and COS-7 cell lines and was reduced only by 10 and 16% in C2C12 and NIH 3T3 cells (data not shown). In contrast, when transfections were preformed with Lipofectamine™ in the presence of 10% FCS, the efficiency of gene delivery was dramatically reduced, by up to 60%.

Different cell lines were incubated in the presence of preformed MPG/DNA complexes (charge ratio of 10:1) in the presence or absence of 10% FCS, DNA being the reporter pRL-SV40 plasmid encoding R.reniformis luciferase for 1 h at 37° C., after which they were replaced in DMEM supplemented with 10% FCS. Twenty-four hours later, cell extracts were prepared and their luciferase activity was determined and reported as a function of total protein. The results correspond to the averages of four separate experiments.

The efficiency of MPG delivery of DNA into HS68 fibroblasts was determined with the pcDNA3.1NT-GFP expression plasmid encoding GFP. HS68 cells were transfected as described for luciferase, in the presence of 10% FCS. GFP expression was monitored by fluorescence microscopy 24 h after transfection. Approximately >90% of the cells expressed GFP, based on phase-contrast image reportings.

D. Cytotoxicity of MPG

In order to generalize the use of MPG as an efficient delivery agent, the degree of cytotoxicity of MPG and of the MPG/DNA complex (charge ratio 5:1) were evaluated in several cell lines, including HS-68 and NIH 3T3 fibroblasts, C212 myoblasts, COS-7 kidney cells and human CEM-SS lymphoblasts. As shown in FIG. 3A, addition of MPG to the culture medium up to a concentration of 10 µM, a concentration well above the $K_d$ of the interaction between MPG and nucleic acids, did not induce any cytotoxic effects over a period of 48 h at 37° C., as already observed for mollicutes (wall-less bacteria) (Beven et al. (1997) Biochim. Biophys. Acta, 1329, 357–369). At much higher concentrations of 0.1 and 1 mM MPG, however, cell viability decreased by ~25 and 60%, respectively. In contrast, when complexed with plasmid DNA (in this case pRL-SV40 at a 5:1 ratio), no cytotoxicity could be observed at a concentration of 0.1 mM MPG; cell viability decreased by only ~40% at a concentration of 1 mM (FIG. 3B). Hence, at the concentration of MPG required for large-scale efficient gene delivery (1–2 µM), no cytotoxicity occurs when MPG is complexed with a plasmid at a 5:1 ratio. These data therefore indicate not only that MPG alone is not cytotoxic at the concentrations required for efficient gene delivery, but moreover that binding of MPG to DNA actually reduces its cytotoxicity at higher concentrations.

E. MPG-Mediated Delivery of a Plasmid Carrying Full-Length Antisense Cdc25c into Mammalian Fibroblasts Promotes Cell Cycle Arrest at the $G_2$/M Transition Efforts in gene therapy focus essentially on the development of strategies to target and knockout specific cellular components responsible for genetic malformations, aberrant development, disorderly growth or malignant proliferation of cells. Both the fast penetration of MPG/nucleic acids into cells and the lack of its cytotoxicity favor its use as an efficient, non-toxic and non-hazardous delivery agent in cellular applications. In an attempt to validate the potential use of MPG in gene therapy, we assessed its ability to deliver pJ3O-antisense-Hucdc25C, a plasmid carrying the full-length antisense cDNA encoding human cdc25C, which has been shown to knock out the mitotic function of human cdc25C and consequently to arrest cells at the $G_2$/M transition when microinjected into mammalian fibroblasts (Morris Thesis, supra). The dual-specificity phosphatase cdc25C plays a key role in the control of cell cycle progression, as a renowned mitotic inducer required to promote entry into mitosis (Morris Thesis; Millar et al. (1991) Proc. Natl Acad. Sci. USA, 88, 10500–10504; Russel et al. (1986) Cell, 45, 145–153). Moreover, cdc25 proteins have been shown to possess an oncogenic potential and as such constitute excellent targets for gene therapy (Galaktionov et al. (1995) Science, 269, 1575–1577; Nagata et al. (1991) New Biologist, 3, 959–968). Synchronised human HS-68 fibroblasts were grown into late $G_1$ phase (12–14/24–25 h cycle in this cell line) and then either mock-transfected with MPG alone, or transfected with MPG pre-incubated with the pJ3O plasmid vector, with pJ3O-sense Hucdc25C, or with pJ3O-antisense Hucdc25C, as described above for the pRL-SV40 plasmid in the presence of serum. Following transfection, cells were incubated for another 14 h before fixation, i.e., at 23–24 h post-refeeding, at which time non-transfected cells normally entered mitosis, and the levels of cdc25C and of cdk2 were evaluated by western blotting. Loss of cdc25C function, and consequent cell cycle arrest was monitored by counting the number of cells exhibiting mitotic phenotypes, with respect to the number observed in non-transfected or mock-transfected cells. FIG. 4A represents the average percentage of mitotic phenotypes observed in each type of transfection experiment. Transfection of MPG or of the pJ3O vector clearly had no effect on the ability of cells to enter mitosis, as compared to non-transfected cells. Similarly, transfection of the pJ3O-sense Hucdc25C construct did not alter the number of mitotic counts 24 h post-refeeding. In contrast, transfection of pJ3O-antisense Hucdc25C with MPG for only 1 h resulted in the efficient inhibition (70%) of entry into mitosis. The levels of cdc25C and cdk2 expression are reported in FIG. 4B. Western blot analysis reveals that in control cells (lane 1) or in cells overlaid with 1 pg of pJ3O vector (lane 2), or pJ3O-sense Hu-cdc25C (lane 3) both cdc25C and cdk2 were normally expressed, confirming that MPG and control vectors do not affect cell progression. In contrast, when cells were transfected with pJ3O-antisense Hcdc25C [0.5 pg (lane 3) or 1 μg (lane 4)] levels of cdc25C protein were strongly reduced with 0.5 μg of DNA and completely abolished with 1 μg of antisense. We finally investigated the effect of MPG-mediated transfection of pJ3O-antisense Hcdc25C on the levels of Hu-cdc25C mRNA by comparison with those of cells mock-transfected with pJ3O vector, by northern blotting. As reported in FIG. 4C, the normal levels of Hu-cdc25C mRNA observed in mock-transfected cells are dramatically reduced in cells transfected with MPG/pJ3O-antisense Hcdc25C complex, whereas control mRNA of GAPDH is present at the same levels in both cases. These data indicate that antisense Hu-cdc25C RNA efficiently forms a hybrid with sense Cdc25C mRNA which is then rapidly degraded. The mechanism by which double-stranded hybrid antisense RNA/sense mRNA is degraded may involve a double-stranded RNA specific RNase. Taken together, these results confirm that the block to mitotic progression observed in the presence of pJ3O-antisense Hucdc25C is effectively due to an antisense effect, which leads to a decrease in the expression of cdc25C. Moreover, in none of the conditions described are the levels of cdk2 affected, which confirms the specificity of the antisense construct. Finally, as for the luciferase reporter system, the efficiency of antisense-Hucdc25C was dependent on the MPG/DNA charge ratio. When a population of cells was transfected with an MPG/antisense DNA charge ratio of 5:1, for instance, cell cycle progression was arrested in >80% of the cells.

F. Materials

Dulbecco's modified Eagle's medium (DMEM) and phosphate-buffered saline (PBS) were from BioWhittaker (Walkersville, Md., USA). L-Glutamine, penicillin, streptomycin and trypsin were from Imperial Laboratories (London, UK). Fetal calf serum (FCS) was from Gibco BRL (Rockville, Md., USA). Lipofectamine® was purchased from Life Technologies Inc. (Rockville, Md., USA). The pRL-SV40 plasmid encoding a *Renilla reniformis* luciferase gene under control of an SV40 promoter was from Promega (Madison, Wis., USA). The pJ3O expression plasmid was provided by Dr P. Jay (IGH, Montpellier, France), the pJ3O-sense and pJ3O-antisense Hucdc25C plasmids, carrying the full-length sense and antisense cDNA encoding human cdc25C, respectively, were constructed by Dr. M. C. Morris (Morris Ph.D Thesis (1997), Montpellier University, Montpellier, France). pcDNA3.1NT-GFP expression plasmid encoding GFP was from Invitrogen (Carlsbad, Calif., USA). Polyclonal rabbit antibody against human cdk2 (#sc-163) was purchased from Tebu, Santa Cruz. An affinity-purified polyclonal antibody against human cdc25C was kindly provided by Dr P. Russell (TSRI, La Jolla, Calif., USA). The Oligotex Direct mRNA kit was obtained from Qiagen (Hilden, Germany). The digoxigenin (DIG) labelling/detection kit was purchased from Boehringer Mannheim (Mannheim, Germany). cDNA encoding for glyceraldehyde-3-phosphate dehydrogenase (GAPDH) was a gift from Dr P. Jay.

G. Peptide Synthesis and Analysis

Peptides were synthesised by solid-phase peptide synthesis using an AEDI-expensin resin with a 9050 Pepsynthetiser (Millipore, Watford, UK) according to the Fmoc/tBuc method, as described previously (Vidal et al. (1996) J. Peptide Sci., 2, 125–133; Méry et al. (1993) Int. J. Peptide Prot. Res., 42, 44–52). Peptides were purified by semi-preparative HPLC and identified by electrospray mass spectrometry and amino acid analysis as also described by Méry et al. (1993) Int. J. Peptide Prot. Res., 42, 44–52. For cellular localization, peptide was coupled with lucifer yellow iodoacetamide dipotassium salt (Molecular Probes, Eugene, Oreg., USA) also as described by Méry et al.

H. Fluorescence Titrations

Fluorescence experiments were performed on a Spex II Jobin Yvon spectrofluorimeter. The intrinsic tryptophan fluorescence of MPG was routinely excited at 290 tun in order to minimize the substrate inner-filter effect and the emission, spectrum was recorded between 310 and 380 nm, with a spectral bandpass of 2 and 8 nm for excitation and emission, respectively. A fixed concentration of MPG ($1 \times 10^{-8}$ to $1 \times 10^{-6}$ M) was titrated by increasing the concentration of each plasmid (from 0 to 10 nM) at 25° C. in a buffer containing 17 mM $KH_2PO_4$, 5 mM $Na_2HPO_4$, 150 mM NaCl, pH 7.4. All measurements were corrected for the equipment and the dilution and curve fitting was performed with the Grafit program (Erithacus Software Ltd (Middlesex, UK) using a quadratic equation which allowed the determination of the MPG/plasmid ratio (Vidal et al. (1997), Comptes Rendus Acad. Sci. Paris, 320, 279–287; Morris et al. (1997) Nucleic Acids Res., 25, 2730–2736).

I. Stability and DNase I Protection Assays

An aliquot of 0.5 μg of the pRL-SV40 plasmid encoding the reporter *R.reniformis* luciferase was incubated for 20 min at 25° C. in PBS buffer, with an MPG concentration corresponding to a peptide/DNA charge ratio ranging from 0:1 to 15:1.

J. Gel Retardation Assays

MPG/plasmid preparations (corresponding to 100 ng of DNA) were analysed by electrophoresis on a 1% agarose gel in TBE buffer, followed by staining with ethidium bromide.

K. DNase I Protection Assays

Preformed MPG/plasmid complexes were treated with DNase I (0.5 μg/ml) in 50 μl of reaction buffer, containing 21 mM HEPES-NaOH, pH 7.5, 135 mM NaCl, 5.0 mM KCI, 0.76 mM $Na_2HPO_4$ 10 mM $MgCL_2$ and 10 mM $CaCl_2$. After 30 min at 37° C., reactions were stopped by addition of 4 M ammonium acetate and 20 mM EDTA and immediate chilling on ice.

L. Serum Protection Assays

Preformed MPG/plasmid complexes were incubated for 5 h in the presence of cell culture medium containing 10% FCS. For both DNase I and serum protection assays, plasmids were extracted with phenol-chloroform, precipitated with ethanol, and then analyzed by agarose gel electrophoresis (1% w/v).

M. Cell Culture, Cytotoxicity Assays, MPG-Mediated Transfection

Adherent fibroblastic HS-68 and NIH 3T3 cell lines, C2C12 myoblasts and COS-7 cells, as well as human CEM-SS lymphoblasts in suspension, were cultured in DMEM supplemented with 1% 200 mM glutamine, 1% antibiotics (streptomycin, 10 000 μg/ml; penicillin, 10 000 IU/ml) and 10% (w/v) FCS, at 37° C. in a humidified atmosphere containing 5% $CO_2$ as described previously (Ausubel et al. (1988) Current Protocols in Molecular Biology, John Wiley & Sons, New York, N.Y.; Gauthier-Rouviere et al. (1996) Mol. Biol. Cell, 7, 719–729. )

The cytotoxicity of both MPG and MPG/plasmid (pRL-SV40 plasmid encoding reporter *R.reniformis* luciferase) complexes were investigated in the cell lines mentioned above. Cells grown in 35 mm diameter dishes to 75% confluency ($0.5-1 \times 10^6$ cells per dish) were incubated with 0.1 μM to 1 mM MPG alone or complexed with DNA in a 5:1 ratio, in 1 ml DMEM for 3 h, after which 10% serum was added. Cell culture medium with MPG or MPG/plasmid was not changed, and cell proliferation was measured over 4 days. Cytotoxicity was evaluated by the MTT colorimetric assay, after removing cell culture medium and replacing it with PBS containing 5 mg/ml of MTT (Mosmann, T. (1983) J. Immunol. Methods, 65: 55–63). Results shown correspond to the averages of four separate experiments.

Lipofectamine™-mediated transfections were performed as described by the manufacturer (Gibco BRL, Cergy Pontoise, France), on cells grown to 75% confluency. For MPG-dependent transfections, cells were grown to 75% confluency and overlaid with preformed MPG/pRL-SV40 plasmid complexes in DMEM (500 µl of DMEM containing 0.5 µg of plasmid, and a variable peptide/DNA charge ratio from 0:1 to 20:1, per 35 mm diameter dish or $0.5–1 \times 10^6$ cells). After 1 h incubation with MPG/plasmid at 37° C., 2 ml of fresh DMEM supplemented with 10% FCS were added to the cells, without removing the overlay of DMEM/MPG/plasmid, and cells were incubated at 37° C. for another 24 h. For transfections in the presence of serum, MPG and DNA were preincubated for 15 min in DMEM, and 10% FCS was then added to this solution before overlaying onto cultured cells. Twenty-four hours after transfection, cells were scraped from their dishes and the luciferase activity of the cell extracts was determined by the luminometric method described in the commercial protocol (Sherf et al. (1996) Promega Notes, 57, 2–9). The protein concentration of cell extracts was routinely determined using the bicinchoninic acid protein assay.

For MPG-mediated delivery of pcDNA3. INT-GFP expression plasmid encoding GFP, HS68 fibroblasts were grown in 35 mm diameter dishes, at 37° C. in DMEM supplemented with 10% FCS until they reached 75% confluence ($0.6–1.2 \times 10^5$ cells per coverslip). Transfections were performed as described for the pRL-SV40 plasmid with preformed complexes of 1 µM MPG and 0.5 µg ADN in a 500 µl overlay of DMEM supplemented with 10% serum (corresponding to a charge ratio of 5:1 MPG/plasmid). After 24 h, GFP expression was monitored by fluorescence microscopy.

For MPG-mediated delivery of antisense nucleic acids directed against human cdc25C, HS68 fibroblasts were grown in 35 mm diameter dishes, at 37° C. in DMEM supplemented with 10% FCS until they reached 75% confluence ($0.6–1.2 \times 10^6$ cells), synchronised for 48 h by serum deprivation, then restimulated to enter the cycle and grown into mid-late $G_1$ for 12–14 h by addition of fresh DMEM supplemented with 10% FCS. Transfections were performed as described above, with preformed complexes of 1 µM MPG and 0.5 and 1 µg DNA in a 500 µl overlay of DMEM supplemented with 10% serum (corresponding respectively to a charge ratio of 5:1 and 10:1 MPG/plasmid). Fourteen hours after transfection, cells were scraped from their dishes and cdc25C and cdk2 protein levels were evaluated by western blotting. Protein samples were separated on 12.5% acrylamide electrophoresis gel, electrotransferred onto polyvinylidene difluoride membrane (Schleicher & Schuell, Northein, Germany) and probed with either polyclonal rabbit anti-human cdc25C or polyclonal rabbit anti-human cdk2, followed by horseradish peroxidase-conjugated goat anti-rabbit secondary antibody. Signals were revealed with the western blotting detection kit (Amersham, pharmacia Biotech, Upsalla, Sweden) and membranes were exposed to X-Omat AR film (Kodak, Eastman Kodak, Rochester, N.Y., USA).

N. Extraction of mRNAs and Northern Blotting mRNA samples were directly prepared using the Oligotex Direct mRNA kit, as described by the manufacturer, from $6 \times 10^6$ cells either mock transfected with MPG/pJ3O vector, or transfected with MPG/pJ3O-antisense Hucdc25C. mRNA samples were diluted 1:1 in sample buffer containing 50% formamide, 10% bromophenol blue, 20% formaldehyde, 5 mM sodium acetate, 1 mM EDTA in 20 mM MOPS, pH 7.0, heated for 5 min at 65° C., and chilled on ice before loading onto a 1.25% agarose gel in OPS/formaldehyde buffer (5 mM sodium acetate, 1 mM EDTA, 20 mM MOPS, pH 7.0, 3% formaldehyde, 1 µl ethidium bromide; 10 mg/ml per 100 ml gel). Samples were separated on the gel run at 5 V/cm in MOPS/formaldehyde buffer. Standard mRNA transfer from the gel onto an N+Hybond membrane was performed overnight in 20×SSC (3 M NaCl, 0.3 M sodium citrate) 2% formaldehyde. mRNAs were fixed onto the membrane by heating for 2 h at 80° C. DIG-labelled control GAPDH probe and Hu-cdc25C probe were prepared as described by the manufacturer from 50 ng GAPDH and 200 ng Hu-cdc25C PCR product amplified through 40 cycles of 1 min at 94° C., 2 min at 56° C. and 2 min at 72° C., with oligonucleotides:

```
                                      (SEQ ID NO:20)
5'-CGGGATCCCGATGTCTACGGAACTCTTCTCATCC-3'

(SEQ. ID NO:21)
5'-CCCCATGGGGTCATGGGCTCATGTCCTTCACCAG-3'
```

Pre-hybridization, hydridization, washes and detection were performed as described in the DIG labelling/detection protocol.

O. Fluorescence Techniques, Photography and Image Processing

Cells expressing GFP were directly observed on a LEICA DM IRB using a 40×1.4 NA lens. Fluorescent images were shot using a Hamamatsu CCD camera directly connected to a PC, and acquired in Adobe Photoshop version 4.0. Images were transferred to a Silicon graphics O2 workstation and converted to SGI raster format using 'convertfile'. Figures were assembled completely and prepared for printing under SGI Showcase 3.2.

P. Conclusion

Our results suggest that peptides as described not only have high affinity for nucleic acids, but also protect them against nucleases. From the results presented above, we suggest that the rapid self-assembly between MPG and DNA first involves electrostatic interactions, as has previously been proposed for cationic peptides, and then promotes further peptide-peptide interactions, leading to the formation of a protective 'cage' around the DNA molecule. Based on these results, we propose that MPG is an excellent tool for the generalized delivery of more than simply oligonucleotides, but larger species of nucleic acids as well, in cultured cells. Finally, given that MPG provides an efficient means to target essential cell cycle proteins with oncogenic potential, such as cdc25C, it will be useful for targeting cellular components involved in genetic malformations, and other diseases. We therefore believe that MPG technology is of prime interest for the development of new gene therapy strategies.

Q. Specifics for FIGS. 1-4

FIG. 1 shows the formation of MPG/DNA complexes. (A) Binding of MPG to DNA monitored by intrinsic fluorescence quenching. The intrinsic fluorescence of MPG was routinely excited at 290 nm and the fluorescence emission was recorded at 340 nm. A fixed concentration of MPG (10 µM) was titrated by increasing the concentration of pJ30-antisense-Hucdc25C plasmid (filled circles) and pRL-SV40 (open circles) (from 0 to 10 nM) at 25° C. in PBS. The curves were fitted according to a quadratic equation, in order to determine the MPG/DNA ratio. The best fit yielded $K_d$ values of $1.8 \times 10^{-4}$ and $0.5 \times 10^{-8}$ M for the pJ30-antisense-Hucdc25C plasmid and pRL-SV40 plasmid respectively, with a maximal quenching of fluorescence of 28 and 32% respectively, obtained at saturating concentrations. (B) Agarose gel-shift assay. The pRL-SV40 plasmid encoding the reporter protein *R.reniformis* luciferase was incubated for 20 min at 25° C. in PBS buffer with different concentrations of MPG corresponding to a charge ratio ranging between 1 and 15, as indicated above each lane. The preformed complexes were analyzed by electrophoresis on agarose gel (1% w/v) stained with ethidium bromide. Lane 1, plasmid DNA control in the absence of MPG; lanes 2–7, charge ratios of 2, 3, 5, 7, 10 and 15 respectively. (C) DNase I and nuclease protection assays. The pRL-SV40 plasmid was incubated at 25° C. in PBS in the presence of increasing concentrations of MPG corresponding to charge ratios shown in (A), as indicated above each lane. The preformed MPG/DNA complexes were treated with DNase I (0.5 µg/ml) and the residual plasmitis were extracted with phenol-chlorofom and analyzed by agarose electrophoresis (1% w/v). Lanes 1 and 2, purified DNA, untreated and treated with DNase I respectively. A total DNA protection was obtained for an MPG/DNA charge ratio of 3 (lane 5). (D) Stability against serum. The preformed MPG/DNA complexes were incubated for 5 h in the presence of cell culture medium supplemented with 10% serum Lane 1, control plasmid; lane 2, plasmid incubated in the presence of serum. Full DNA protection was obtained for a charge ratio of 5.

Figure 2:
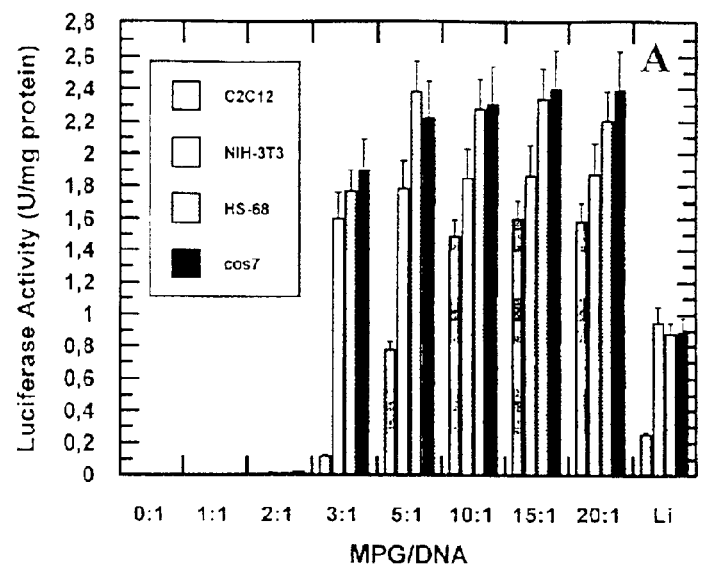
FIG. 2 shows (A) MPG-mediated pRL-SV40 plasmid delivery of different cell lines and over different peptide vector: DNA ratios.
Figure 2:
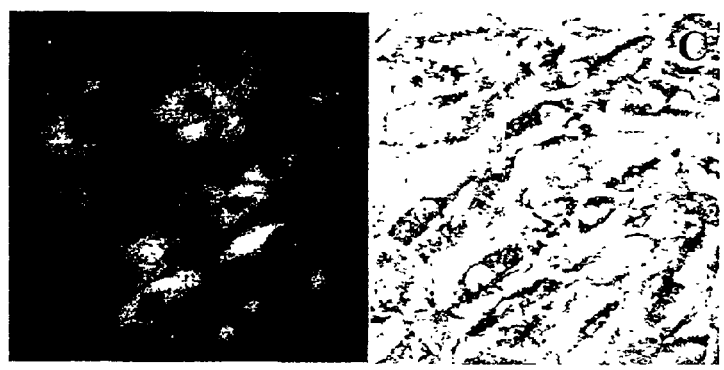

FIG. 2 shows the MPG-medicated pRL-SV40 and pcDNA3.1NT-GFP plasmid delivery. (A) Different cell lines were incubated in the presence of preformed MPG/DNA complexes (varying in the MPG/DNA charge ratio up to 20:1, corresponding to an MPG concentration of 1.6 µM; DNA being the reporter pRL-SV40 plasmid encoding *R.reniformis* luciferase) for 1 h at 38° C., after which they were replaced in DMEM supplemented with 10% FCS. Twenty-four hours later, cell extracts were prepared and their luciferase activity was determined and reported as a function of total protein. Similar transaction experiments were performed as controls using Lipofectamine® and for 4 h transfection, as described in the commercial transfection protocol. Maximal transfection efficiency using MPG was obtained for a charge ratio of 10:1, yielding luciferase activities of 2.4, 2.45 and 1.9 U/mg of protein for HS-68, COS-7 and NIH 3T3 cells, respectively. For C2C12 cell lines, maximal transfection was obtained for a charge ratio of 15:1 yielding a luciferase activity of 1.6 U/mg of protein. Using Lipofectamine® this value was at least twice and seven times lower, corresponding to a luciferase activity of –0.9 and 0.3 U/mg of protein. Each result corresponds to the average of four separate experiments. HS68 fibroblasts cultured on glass coverslips in DMEM supplemented with 10% FCS were transfected with MPG/pcDNA3. INT-GFP complexes (ratio 5:1). After 24 transfection, the cells were analyzed by fluorescence and phase-contrast microscopies. (B) GFP expression; (C) corresponding phase-contrast image.

Figure 3:
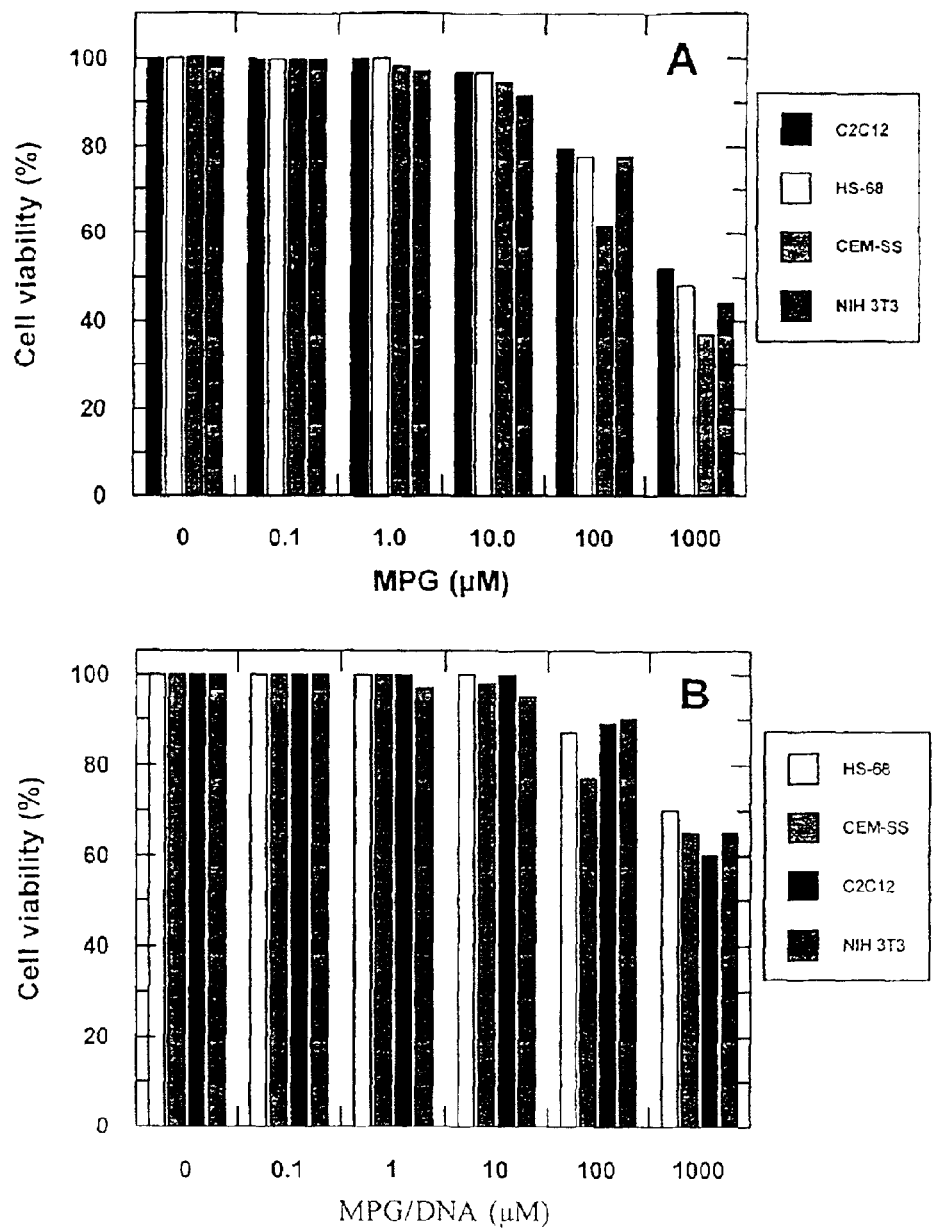
FIG. 3 shows the cytotoxicity of MPG in cells HS-68, NIH 3T3, C2C12, COS-7 and CEM-SS cell lines over various concentrations for (A) the vector alone and for (B) the vector complexed with DNA.

FIG. 3 shows the Cytotoxicity of MPG. HS-68, NIH 3T3, C2C12, cos-7 and CEM-SS cell lines were incubated with 0.1 µM to 1 mM MPG alone (A) and with MPG complexed with DNA (pRL-SV40 plasmid encoding *R.reniformis* luciferase) in a peptide/DNA ratio of 5:1 (B), at 37° C. in DMEM supplemented with 10% FCS. The cytotoxicity of MPG alone and of MPG/DNA complexes was evaluated in MTT colorimetric assays and the results were expressed as percentages of dye reduction in cell lines incubated without MPG. The results correspond to averages of four separate experiments.

Figure 4:
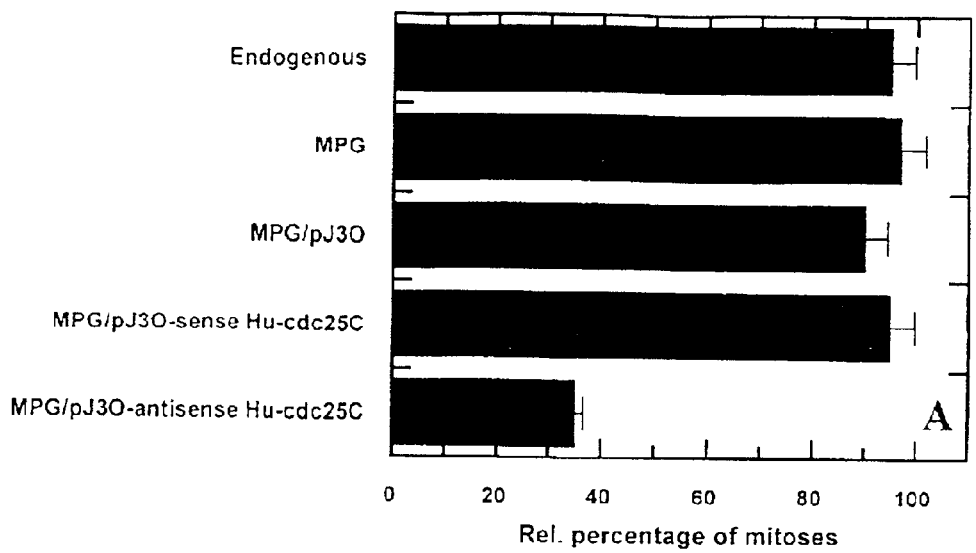
FIG. 4 shows the results of MPG-mediated delivery of antisense human cdc25C into mammalian fibroblasts by: (A) mitotic index, (B) Western blot, and (C) Northern blot.
Figure 4:
Figure 4:
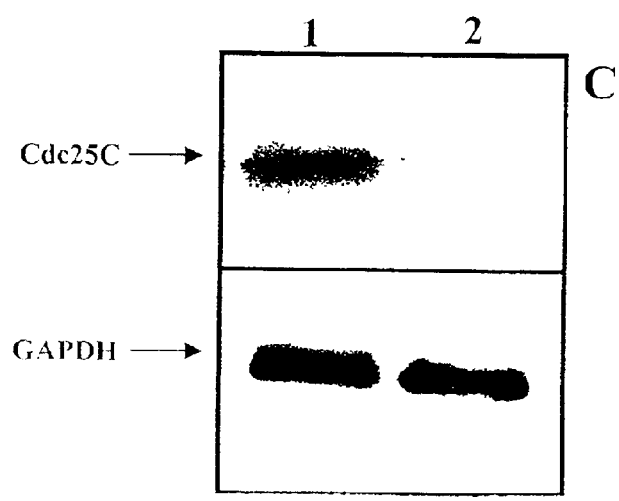

FIG. 4 shows the MPG-mediated delivery of antisense human cdc25C into mammalian fibroblasts. HS68 fibroblasts cultured in DMEM supplemented with 10% FCS were synchronized through serum starvation for 48 h, and grown into late $G_1$ (12–14 h post-refeeding), prior to transfection. Cells were then either mock transfected (with MPG peptide alone), or transfected with MPG/pJ3O plasmid, MPG/pJ30-sense Hucdc25C or MPG/pJ30-antisense Hu-cdc25C, constructs encoding full-length sense or antisense human cdc25C, respectively, under the control of an SV40 promoter. After 1 h transfection in the presence of serum, fresh DMEM supplemented with 10% serum was added and cells were incubated for another 12–14 h, then fixed with methanol and shined with an antibody against tubulin and with Hoechst. The ability of transfected cells to progress into mitosis was assessed as a function of the number of mitotic phenotypes observed (centrosome duplication, spindle formation, metaphase plate, chromosome segregation, midbody). (A) The average number of mitotic counts for each transfection experiment (repeated at least five times) was normalized with respect to the number of mitotic phenotypes counted in a population of non-transfected cells, 24 h post-refeeding. The results for each type of transfection experiment are consequently expressed as the relative percentage of mitotic phenotypes. (B) Fourteen hours after transfection, cells were scraped from their dishes and the protein levels of cdc25C and cdk2 were evaluated by western blotting. Protein samples were separated by 12.5% SDS-PACE, transferred onto a polyvinylidene difluoride membrane and probed with either polyclonal rabbit anti-human cdc25C or polyclonal rabbit anti-human cdk2, followed by horseradish peroxydase-conjugated goat anti-rabbit secondary antibody. Lane 1, control cells; lanes 2 and 3, cells mock-transfected with 1 µg of pJ30vector and 1 µg of pJ30-sens-Hucdc25C; lanes 4 and 5, cells transfected with 0.5 and 1 µg of pJ30O-antisense Hcdc25C respectively. (C) Northern blot analysis of Hu-cdc25C gene expression. Total RNA was prepared from cells transfected with 1 µg of pJ30 (lane 1) or 1 µg of pJ30 antisense Hu-cdc25C (lane 2) and analyzed by northern blot as indicated in the Materials and Methods. The northern blot was subsequently hybridized with a GAPDH probe as control to normalize loading sample.

Example 2

The Synthesis of New, Highly Useful Peptide Vectors

Here we describe the design of amphipathic peptides containing a cationic nuclear localization sequence, such as done previously for MPG. We show that this type of peptide can act as a carrier for drugs and nucleic acids that are either covalently linked or involved in the formation of a non-covalent complex with the peptides.

Our goal was to improve the induced cellular internalization power of our previous vectors, the design of which were based on concepts differing from those previously reported. The present vectors address the following considerations: 1) The peptide should contain a membrane anchoring sequence which can be either amphipathic or hydrophobic. We used the latter since besides the possibility of membrane binding, a hydrophobic sequence offers the possibility to complex hydrophobic molecules that are otherwise poorly soluble in aqueous media. Among the hydrophobic peptide sequences, we selected a signal peptide and a sequence issued from a fusion protein. 2) The vector should contain a hydrophilic sequence that can correspond to an addressing message, e.g., an NLS (nuclear localization signal). We selected an NLS for our amphipathic peptides, which has advantage in its strongly hydrophilic composition and which thus can facilitate solubilization in water of the hydrophobic domain. 3) The vector peptide should optionally bear a functional group which will allow its post-synthesis coupling to other molecules. 4) Finally, the sequences of the vectors should be easy to handle, especially from the synthesis point of view, and also preferably contain a Trp residue acting as an intrinsic fluorescent probe. We addressed each of these considerations through the following:

To address the first consideration, we used the signal peptide of the Ig(v) light chain of caïman crocodylus (M-G-L-G-L-H-L-L-V-L-A-A-A-L-Q-G-A) (SEQ ID NO:22); (Briggs et al. (1986), Adv. Prot. Chem. 38, 109).

To address the second consideration, we employed the NLS sequence of the large T-antigen of SV40 (P-K-K-K-R-K-V) (SEQ ID NO:23) Kalderon et al., 1984, Nature (London), 311, 33; Goldfarb et al., 1986, Nature (London), 322, 641).

Once selected, the sequences were linked either through a W-S-Q-P sequence (SEQ ID NO:24) leading to an A-W-S motif which constitutes a peptidase sensitive motif or by binding them omitting the Pro residue, thus reducing the sensitivity to proteases. The following five peptides were designed based on this concept:

plexation formed through electrostatic interactions (for negatively charged hydrophilic drugs or nucleic acids).

A. Peptide Synthesis

All peptides were synthesized by the continuous flow solid phase Fmoc strategy using a Pepsynthetizer Milligen 9050. The resin was AEDI-Expansin (AEDI= aminoethyldithio 2-isobutyric acid) and the N-protected amino acids were activated by TBTU and HOBT. Some double couplings were performed at crucial steps where, according to our own experience, a single coupling leads to a strong lowering of the yield and thus to a strong increase in difficulty at the purification step.

After acetylation of the side-chain protected peptidyl-resins; the protections were removed with TFA/ethanedithiol/thioanisole/phenol/$H_2O$ (94:4:2:2:2) and then the peptides were released by TCEP HCl (TCEP=tris(2-carboxyethyl)phosphine) leading to the required cysteamide forms of the N-acetylated peptides. They were all purified by semi-preparative HPLC in isocratic conditions and identified by amino acid analysis and mass spectroscopy (Vidal et al., 1996, J. Pept. Sci., 2, 125).

B. Cellular Localization of the Peptides

In a first step we have verified that the peptides thus designed can be internalized by cells and that the final localization is nuclear according to the presence of the NLS. Simultaneously we also checked the ability for these peptides to carry small molecules toward the intracellular domains. This was achieved through the linking, on the C-terminal SH function, of a fluorescent probe namely lucifer yellow (LY) which allows either fluorescence or confocal microscopy detection. The conjugate was synthe-

| | |
|---|---|
| M-G-L-G-L-H-L-L-V-L-A-A-A-L-Q-G-A-W-S-Q-P-K-K-K-R-K-V [1] | (SEQ ID NO:25) |
| M-G-L-G-L-H-L-L-V-L-A-A-A-L-Q-G-A-K-K-K-R-K-V [2] | (SEQ ID NO:26) |
| G-A-L-F-L-G-W-L-G-A-A-G-S-T-M-G-A-W-S-Q-P-K-K-K-R-K-V [3] | (SEQ ID NO:27) |
| G-A-L-F-L-G-W-L-G-A-A-G-S-T-M-G-A-R-K-K-K-R-K-V [4] | (SEQ ID NO:28) |
| G-A-L-F-L-G-F-L-G-A-A-G-S-T-M-G-A-W-S-Q-P-K-S-K-R-K-V [5] | (SEQ ID NO:29) |

Where [5] corresponds to [3] but with two substitutions. All peptides were N-acetylated in order to maintain the hydrophobic domain and improve their chemical stability.

Consideration 3 is observed if all peptides are made to bear at their C-terminal a cysteamide group (—NH—$CH_2$—$CH_2$—SH), which allows further coupling to drugs. In addition, this cysteamide group is compatible with the peptide synthesis using the Fmoc strategy and leads to a C-terminal protected peptide (Méry et al., 1992, Pept. Res., 5, 233; Méry et al. 1993, Int. J. Pept. Protein Res., 42, 44). Other coupling groups also exist that can serve this function, as those of skill in the art are aware.

Consideration 4 is addressed since [3] and [4] contain a Trp residue and no sequence known to present synthesis difficulties (such as Val-Val-Val or high Arg content) are found in these sequences.

Figure 5:
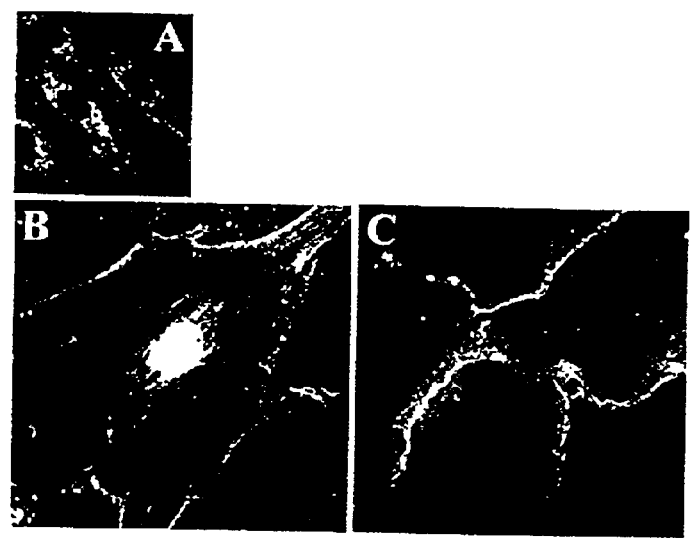
FIG. 5 shows the cellular localizations of: (A) free lucifer yellow (LY); (B) LY linked to [3]; (C) LY linked to [4]; (D) LY linked to [1]; (E) LY linked to [2] (3 min incubation at 10 $\mu$M).
Figure 5:
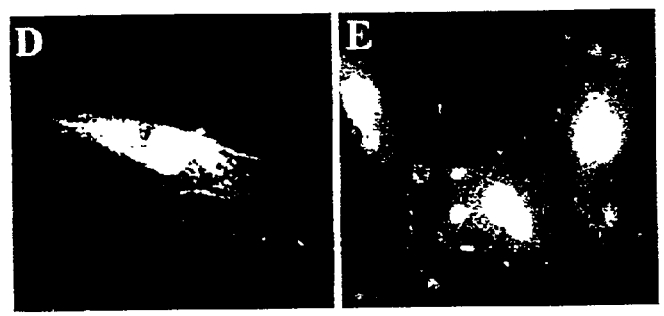

Thus we obtained a series of peptides which were expected to act as carriers through different mechanisms according to the method of binding to the drug, i.e.:

1) covalent binding via the C-terminal SH, and
2) formation of a complex through hydrophobic interactions (for hydrophobic drugs) and non-covalent comsized by reacting the peptide with lucifer yellow iodoacetamide dipotassium salt for 30 min in the dark and purified by HPLC. Using this fluorophore as probe, the final localization of the peptides was observed after only 3 min incubation and a strong sequence dependence was noticed (FIG. 5). While the free fluorophore leads to a perinuclear localization, for peptides [1] and [2] no marked difference could be noticed and both peptides clearly localize in the nuclei of the cells (mammalian fibroblasts, NIH 3T3 fibroblasts or murine L1210 lymphocytes) and this occurs within an incubation time of less than 3 min. (Méry et al., 1992, Pept. Res., 5, 233; Méry et al. 1993, Int. J. Pept. Protein Res., 42, 44). For the two other peptides the situation is different and while [4] remains membrane associated, [3] reveals both localizations, membrane associate and nuclear with, however, a more pronounced uptake of the probe into the nucleus (Chaloin et al. (1998), Biochem. Biophys. Res. Commun., 243, 601; Chaloin et al.(1997), Biochemistry, 36, 11179.

It must be added that the uptake and the final localization do not depend on the temperature (37 or 4° C.) suggesting thus a mechanism avoiding an endocytosis pathway. In addition, some minor modifications of the peptide sequences such as the deletion of a Val residue in the signal peptide, or substitutions such as Phe→Trp in the fusion sequence and Lys→Ser in the NLS domains do not influence the overall final localization of the probe. The termini biotinylated derivatives of [1] and [2] which lead to very similar images as for the lucifer yellow conjugate. The fact that N- and C-terminal probes lead to identical localizations providess a good indication that no cleavage of the peptide occurs during the cellular uptake.

C. Vectorization Properties

On the basis of the design of the peptides, two different vectorization approaches were used: i) covalent binding through the SH, and ii) noncovalent complex formation involving the C-terminal NLS. In the following, the description of the transfer will be restricted to that of nucleic acids (oligonucleotides, RNA or DNA), although it is understood that the same is capable with other types of molecules.

(1) Covalent Binding

The ability for these peptides to act as carriers for biologically active molecules was investigated using two types of oligodoexynucleotides (ODN). The first was an anti-TAT-N while the second was an antisense oligodeoxynucleotide of the phosphorothioate series.

The first ODN has the sequence d(GGTCTTACTCTCCGTCTCT) (SEQ ID NO:30). It was modified in 5' by a hexamethylene-bridged pyridyldisulfide and in 3' by a 2-propanol-3-amino group and labeled with rhodamine. Conjugation was performed by stirring a solution of the oligonucleotide with a three fold excess of peptide for 3 h. The cellular localization of the conjugate, after 5 min incubation with human fibroblasts (HS-68), is well defined and clearly cytoplasmic but not nuclear while no spontaneous cellular internalization could be detected for the free oligonucleotide. The target compartment of the conjugate remains to be identified.

Figure 6:
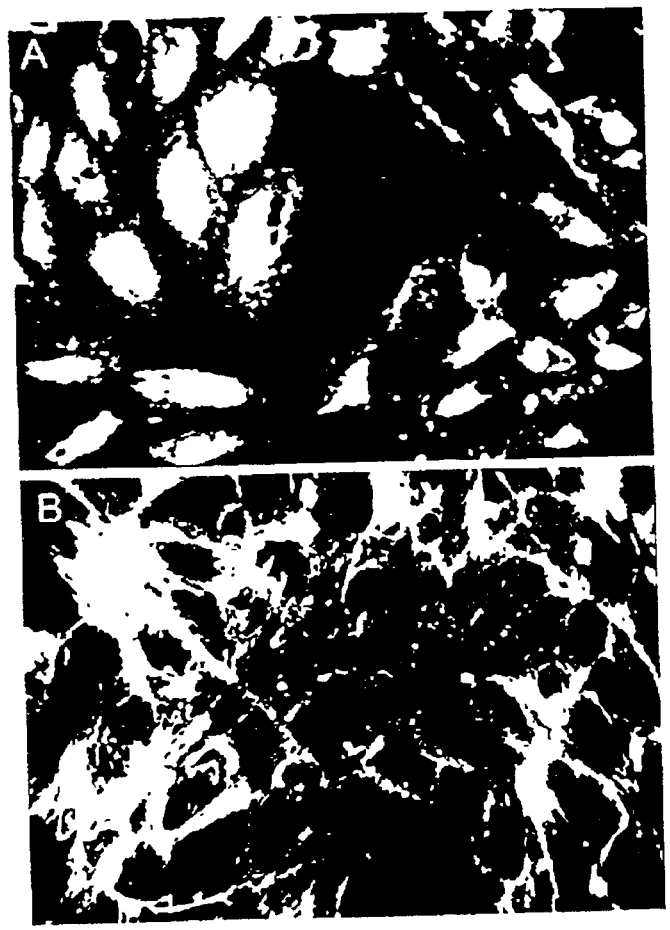
FIG. 6 shows the cellular localization of: (A) ODN-conjugate (5 min incubation at 37° C. and (B) Control with free ODN. (C) gives the $Ba^{++}$ current density of treated H9C2 cells.
Figure 6:
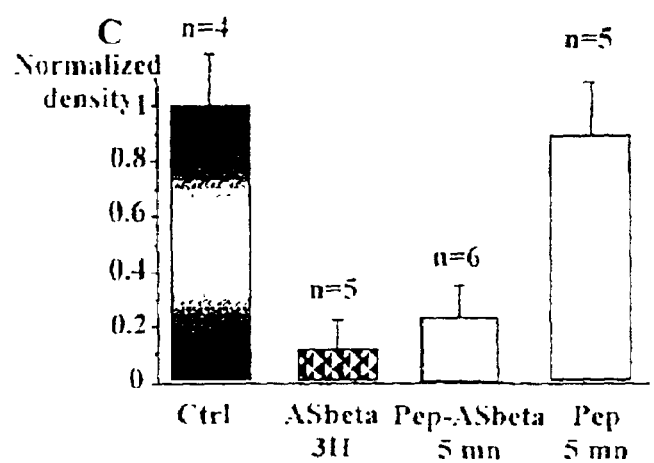

For the second ODN, the situation is clearer. This ODN conjugated 3' with fluorescein and containing an SH group in 5' for localization reasons has the sequence 5'-ACCAGCCTTCCGATCCACCAGTCATT-3' (SEQ ID NO:31) and corresponds to the AS-βCOM antisense sequence complementary to conserved sequence region found in every mRNA encoding β subunit of $Ca^{2+}$ channels. After 5 min incubation at 37° C., more than 90% of the cells (cardiac cell line H9C2) were labeled in the nucleus while only 25% of the cells were labeled after 3 hours incubation when using the free ODN. For all labeled cells whatever the internalization process, as expected, $Ba^{2+}$ current density was strongly reduced (≈7 fold) (FIG. 6). This result proved the peptide to be an efficient carrier and also that the antisense activity was conserved (Chaloin et al., 1998, Biochem. Biophys. Res. Commun., 243, 601).

(2) Binding Through Formation of a Complex

The vector peptides contain charged residues located in the C-terminal NLS sequence forming thus a primary amphipathic peptide and therefore properties similar to those of cationic lipids, especially the ability to form complexes with nucleic acids. Based on the earlier examples and data below this is indeed the case for single and double stranded oligonucleotides, as well as for RNA and DNA.

Figure 7:
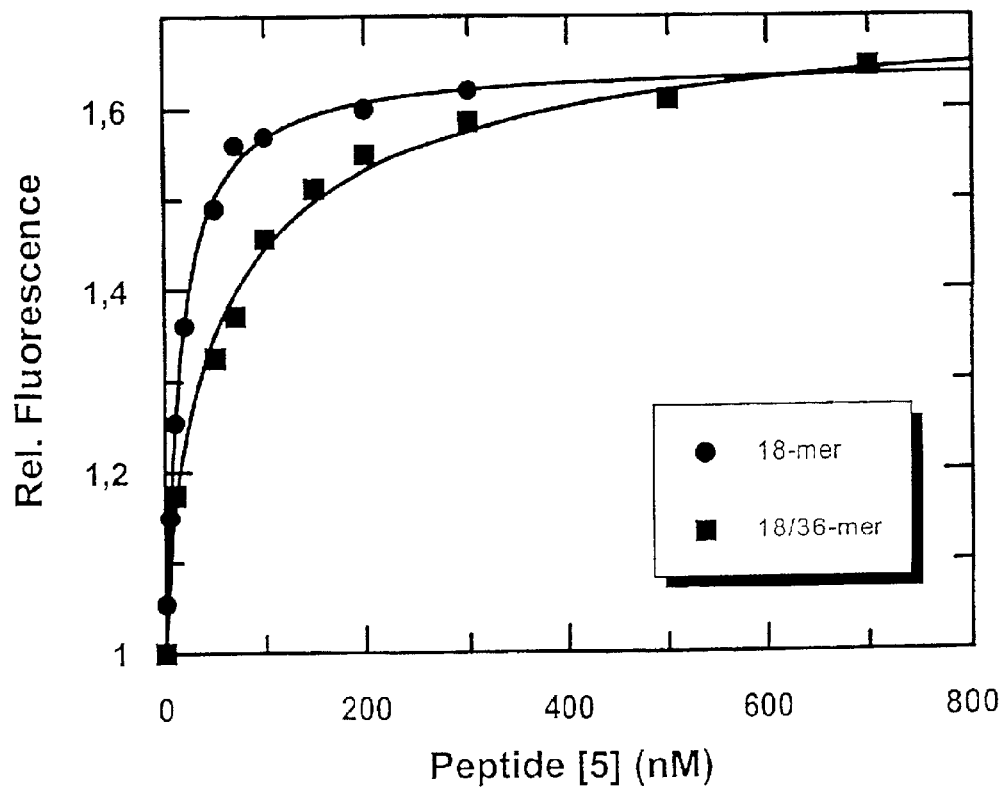
FIG. 7 shows the formation of peptide-oligonucleotide complexes as monitored by the variations of fluorescence.

Complex formation between peptide and oligonucleotide was monitored either by the use of fluorescently labeled oligonucleotides or the fluorescence properties provided by the presence of a single Trp residue as is the case of peptide [5] (FIG. 7).

Figure 8:
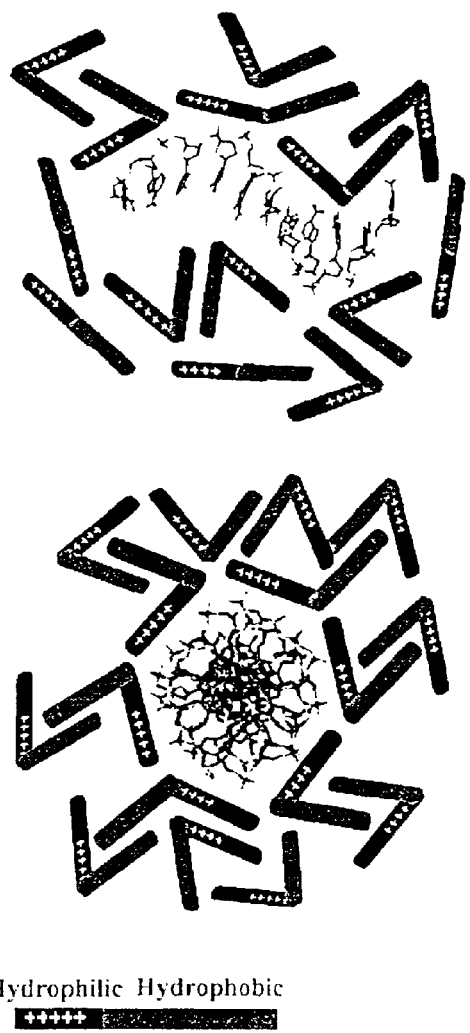
FIG. 8 shows the schematic representation of a possible configuration of the mixed oligonucleotide-peptide particle. Upper: side view. Lower: top view.
Figure 9:
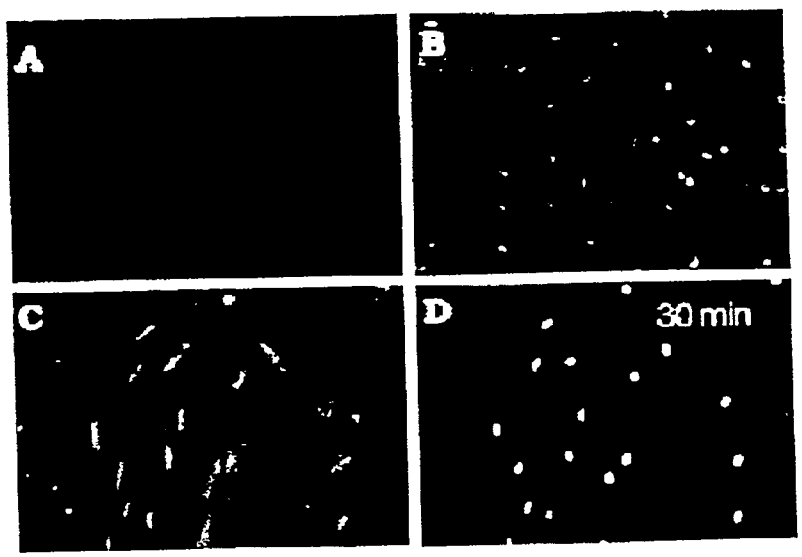
FIG. 9 shows the peptide-mediated delivery of oligonucleotides in human fibroblasts. (A) and (B) are control experiments with fluorescently labeled phosphorothiate oligonucleotide in the absence of MPG. (C), (D), (E), and (F) show the MPG-mediated delivery of single-stranded oligonucleotide. (G) and (H) show the MPG-mediated delivery of double-stranded oligonucleotide. In (B), (D), (E) and (H), the cells are stained with the nuclear stain Hoescht 33258.
Figure 9:
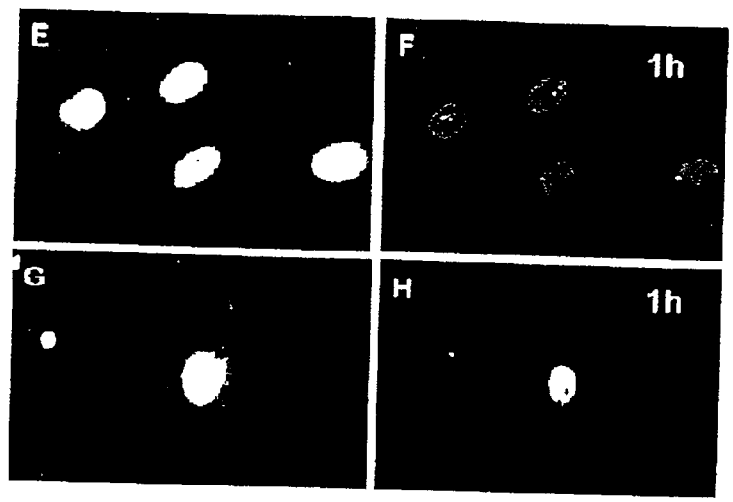

The peptides exhibit relatively high affinity, in the nanomolar range, for single and double stranded oligonucleotides and the interactions occur mainly through electrostatic interactions involving the positively charged residues of the NLS. Formation of the particle (FIG. 8) which acts as vector involves further interaction of the peptide-peptide type with a peptide/nucleotide ratio of about 5. Using HS 68 and NIH-3T3 cells to probe the efficiency of the internalization, 1 h incubation was enough to obtain complete delivery in >90% of cells with a final localization of the oligonucleotides (single or double stranded) which was mainly nuclear (FIG. 9).

The rapid internalization together with the fact that low temperature or modification of the culture medium do not block the cellular uptake suggests that we are not dealing with a mechanism involving the endosomes. In addition, the interactions between the oligonucleotides and the vector peptides increase the stability of the oligonucleotide to nucleases (Chaloin et al. 1998, Biochem. Biophys. Res. Commun., 243, 601.

In the case of larger nucleic acids (RNA or DNA), we first checked the ability of [5] to form complexes with these macromolecules. For a RNA this was achieved using a single stranded RNA, namely the mRNA encoding the p66 subunit of HIV-1 RT, the binding was monitored by the quenching of the intrinsic fluorescence of the peptide. The peptide presents a relatively high affinity for the mRNA with a dissociation constant in the $10^{-7}$ M range.

The saturation of the peptide occurred with a 4000 fold lower concentration of mRNA, which is about 13 fold higher than that expected on the sole basis of electrostatic interactions between the basic residues of the peptide and the acidic phosphate groups of the mRNA. As already described for oligonucleotides, the fluorescence results suggest that the mechanism of peptide/RNA complex formation first involves peptide/RNA interactions which than promote peptide/peptide interactions forming thus a capsid-like complex which protects the mRNA from nucleases and thus prevents serum induced degradation (Vidal et al. (1997), Comptes Rendus Acad. Sci. Paris, 320, 279). For DNAs the same behavior has been observed and again the formation of a capsid-like particle prevents the DNAs from degradation.

The ability of the peptide to transfer a DNA or a single stranded fluorescently labeled mRNA into HS-68 human fibroblasts and compared to the commonly used cationic lipid lipofectamin™. While in the latter case, a maximum 50% transfection yield is obtained after 5 h incubation with a mRNA-containing complex, the peptide-assisted transfer concerns 90% of the cells within 1 h incubation and all the fluorescence is localized in the cytoplasm. Beside the fact that the peptide is a powerful tool for the transfer of mRNA, this result also indicates that the peptide protects the RNA from degradation since no fluorescence arising from cleaved fluorophore can be detected in the cell nuclei. The transferred mRNA is rapidly expressed in the cells (Vidal et al., 1997, Comptes Rendus Acad. Sci. Paris, 320, 279). Similarly, transfections using double stranded DNAs encoding for β-galactosidase or luciferase or an antisense DNA constructed to inhibit the expression of a protein involved in the cell cycle process, were more efficient when using peptide [5] than Lipofectamine with protection of the DNAs.

Figure 10:
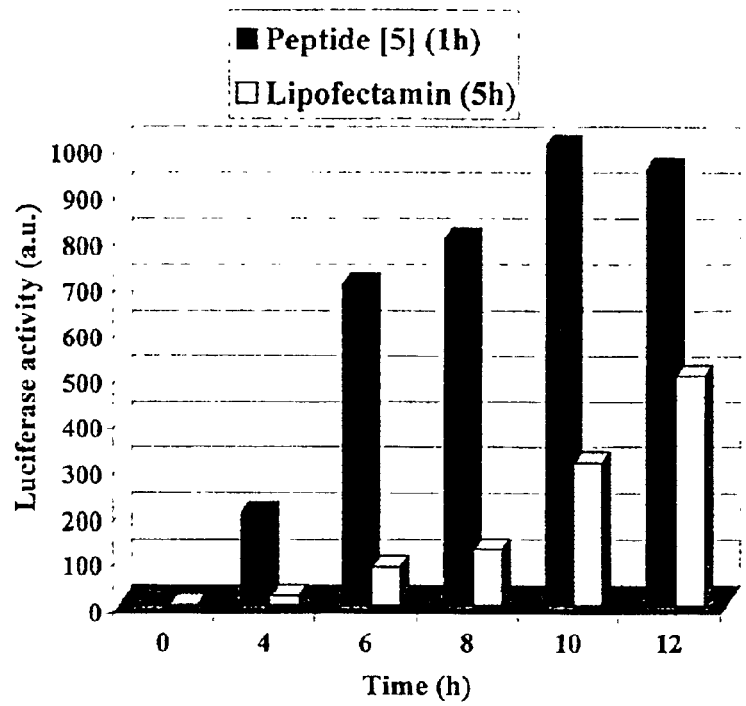
FIG. 10 shows the comparison of the kinetics of expression of a mRNA using two transfection agents: peptide [5] and lipofectamine.

The kinetics of expression was monitored by using a mRNA encoding a reporter protein, the *renilla luciferase* and the maximal expression occurred 6 h after transfection with the peptide while 12 h are required with lipofectamine™ with a much lower yield (FIG. 10).

D. Toxicity of the Vectors

When used at high concentration levels (>10 µM) some of the peptides proved to be toxic. This toxicity was first analyzed on mollicutes which are wall-less bacteria. The bacteriocidal, activity was shown efficient against some strains, notably *Acheloplasma laidlawii*, although less potent than melittin. Also, in contrast to melittin, their activity was independent of the thickness of the plasma membrane. [1] and [2] decrease, though less efficiently than melittin, *Acheloplasma laidlawii* and *Spiroplasma melliferum* membrane potential and transmembrane pH gradient at concentrations much lower than their minimal inhibitory concentrations while the others have no effect in the same conditions (Beven et al. 1997, Biochim. Biophys. Acta, 1329, 357).

Figure 11:
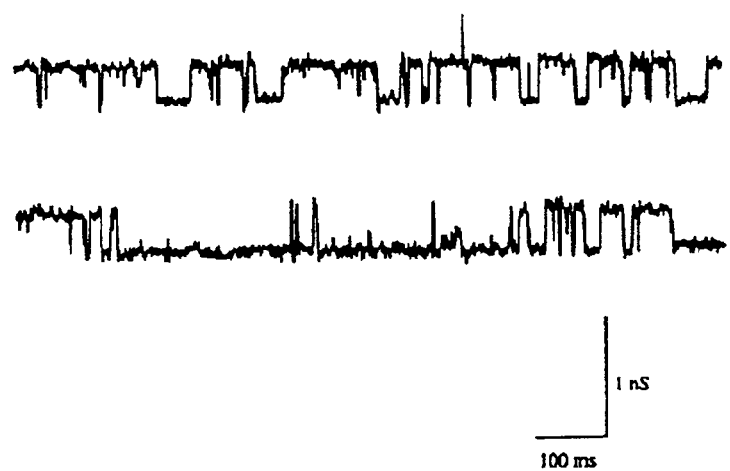
FIG. 11 shows the single channel trace obtained with peptide [2] when incorporated into planar lipid bilayers.

It appears that the molecular mechanism giving rise to the bacteriocidal activity can be related to the ability for these peptides, at least peptide [2], to induce formation of transmembrane ionic channels. They were characterized on *Xenopus laevis* oocyte plasma membranes and confirmed on planar lipid bilayers proving thus that channel formation is a true property of the peptide (FIG. 11). The insertion of the peptide in the membrane is voltage-triggered and the channel thus formed are selective for monovalent cations. The similar single channel conductances observed for the two types of membranes indicates that the mechanism of channel formation is the same in both cases. Since the peptide does not display the typical multi-level behavior observed with alamethicin, namely the barrel-stave model, but a behavior which is reminiscent of that found for magainin we propose that the peptide forms preaggregates on the membrane surface (Chaloin et al. (1998), Biochim. Biophys. Acta, 1375, 52).

For the other peptide the toxicity is lower and almost completely abolished upon formation of a complex with the nucleic acids.

E. Conformational Analysis and Mechanism of Translocation

In order to identify the mechanism which is involved in the membrane translocation process we undertook a conformational study of the various peptides both in solution and in membranes or membrane mimicking environments. Together with these investigations we have studied the interactions with phospholipids using the Trp fluorescence properties and technologies based on the study of mixed peptide-lipid monolayers. We have examined the lipid-induced peptide conformational changes in association with the peptide-induced topological modifications of the monolayers.

(1) Conformations of the Peptides in Solution

Figure 12:
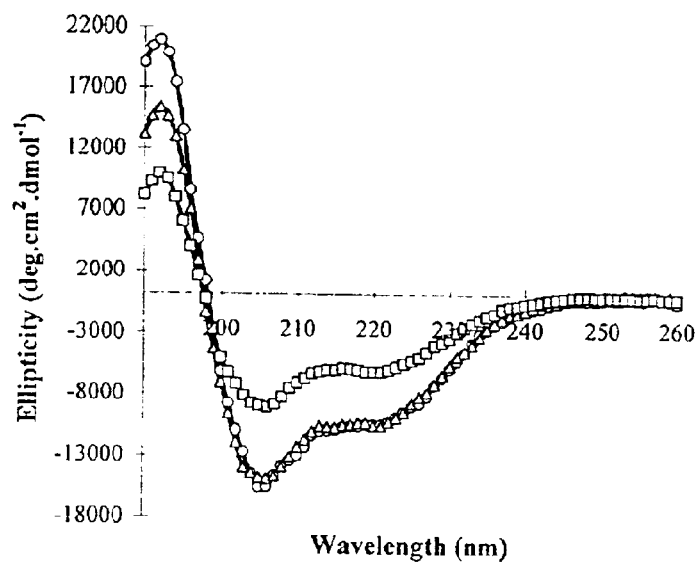
FIG. 12 shows the far UV-CD spectra of peptide [1] in water at various TFE amounts.

When in water all peptides appear to be non-structured. This was assessed on the basis of both CD and proton NMR spectroscopy. Indeed, their far UV CD spectra are characterized by a single minimum at 198 nm and the NMR spectra only reveal strong sequential $d_\alpha N$ NOEs. The ability for these peptides to adopt a structured conformational state was checked as usual by additions of trifluoroethanol (TFE) to the water medium (FIG. 12). As expected TFE induces the formation of an α-helical structure which reaches a maximum at 30% TFE leading to about 50% α-helix as estimated from the ellipticity at 222 nm. The localization of the structured domain within the sequence was achieved by NMR. The various observed dNN(i, i+2), $d_\alpha N$(i, i+3), $d_\alpha N$(i, i+4) and $d_{\alpha\beta}$(i, i+3) confirmed the existence of an α-helical conformation extending from residue 1 to 20 in 70% TFE for peptide [1] while the remainder is non-structured (Chaloin et al. (1997), Biochemistry, 36, 11179; Vidal et al. (1998), J. Membrane Biol., 162, 259; Vidal et al (1997), Lett. Pept. Sci., 4, 227; Chaloin et al., 1997, Lett. Pept. Sci., 4, 231.

(2) Conformation in a Membrane Mimicking Environment

Figure 13:
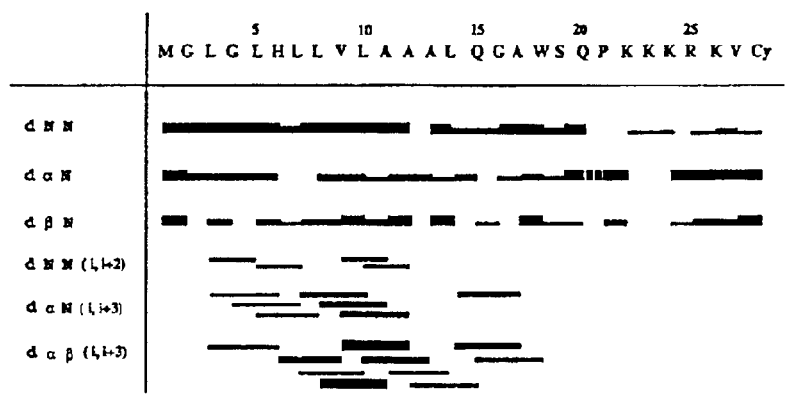
FIG. 13 shows the medium-range NOE contacts of peptide [1] in a water-SDS-$d_{25}$ (molar ratio 100).

The classical approach for studying membrane associated peptides consists in the use of micelles where the peptides can embed. For technical reasons, especially since the perdeuterated derivative is commercially available, sodium dodecylsulfate (SDS) is one of the most used micelle-forming compound. In addition to this advantage, SDS is also appropriate for spectroscopic studies and allows far UV (down to 185 nm) investigations. CD observations in association with NMR indicate that when incorporated in SDS micelles all peptides adopt, at least in part an α-helical structure (FIG. 13). Similarly to the observations made in TFE containing media, the structured domain concerns the hydrophobic ones (signal peptide or fusion sequences) while the hydrophilic sequence (the NLS) remains disordered (Chaloin et al. (1997), Biochemistry, 36, 11179; Vidal et al. (1998), J. Membrane Biol., 162, 259).

Identification of the positioning of the peptide (surface associated or micelle embedded) was achieved using the fluorescence properties of the Trp residues, when present. For peptide [4] which contains a single Trp located in the hydrophobic sequence, upon binding to micelles of SDS the fluorescence emission shifts from 355 to 330 nm and this shift is accompanied by an enhancement of the fluorescence intensity. This indicates that the indole of the Trp moves from a polar environment (the water) to a non-polar one (the hydrophobic micelle core) and thus that the hydrophobic domain of the peptide is embedded in the micelle core.

(3) Conformations in the Presence of Phospholipids

While the situation is simple when the peptides are in the presence of micelles, the presence of phospholipids generates different trends according to the peptide concentration, the nature of the phospholipid headgroups (neutral or positively charged) and the physical state of these phospholipids (gel; i.e; liquid condensed or liquid crystal; i.e., liquid expanded). Before describing the phospholipid induced conformational states let us focus on some major differences occurring between the two series of peptides SP-NLS and FP-NLS and which were detected by penetration experiments of the peptides into lipid mono- and bilayers. For [1] and [2], no major influence of the nature of the polar headgroups (phosphatidylcholine or phosphatidylserine) could be detected, at least when concerning penetration experiments. Indeed, for [1] which contains a single Trp located at the junction of the hydrophobic and hydrophilic sequences both types of lipid, in vesicular form induce the same blue shift (from 352 to 342 nm) of the Trp fluorescence emission. This was confirmed by monolayer penetration experiments. For both lipids the same surface pressure increase was detected and the amplitude of the increase (~15 mN/m) indicates that strong hydrophobic interactions occur within the monolayer (Chaloin et al. (1997), Biochemistry, 36, 11179.

For the other series of peptides, the situation is different since no variation of the Trp fluorescence emission could be detected with DOPC while a 30 nm blue shift occurs with DOPS. Monolayer experiments are in full agreement with this behavior. Indeed, for DOPC only an increase of 6 to 7 mN/m occurs indicating that the peptide-lipid interactions are restricted to electrostatic interactions (probably between the lipid headgroups and the peptide NLS sequence) while for DOPS, again a strong increase (~15 mN/m) of the surface pressure occurs (Vidal et al. (1998), J. Membrane Biol., 162, 259).

The reasons for the difference between the behavior of the two series of peptides is not clear at all since they differ only by their hydrophobic sequences, the NLS remaining the same.

Figure 14:
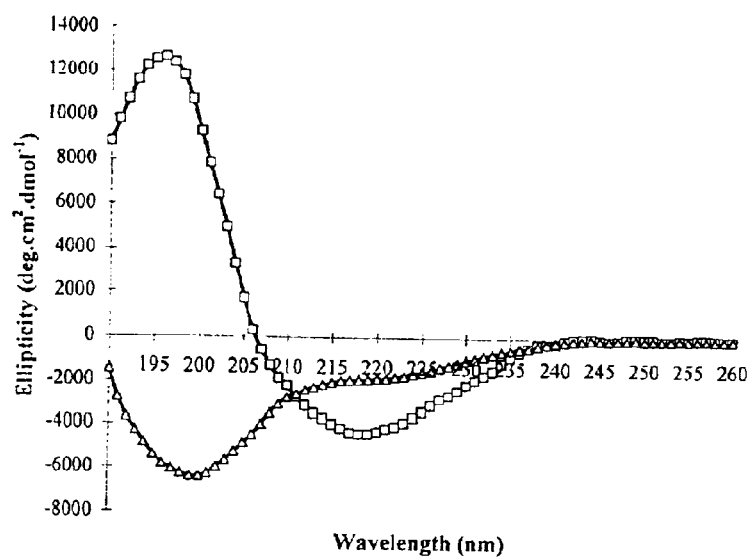
FIG. 14 shows the far UV-CD spectrum of peptide [1] in Δ water and in the presence of DOPG vesicles (molar ratio 50) shows the FTIR spectrum of transferred monolayers of [1] (Amide I band): O pure peptide, Δ with DOPG, with DOPC.
Figure 15:
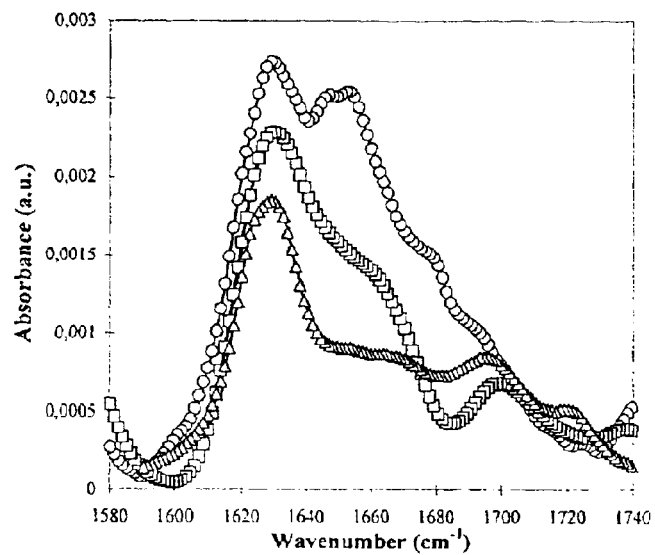
FIG. 15 shows the FTIR spectrum of transferred monolayers of [1]: O pure peptide, Δ with DOPG, with DOPC.
Figure 16:
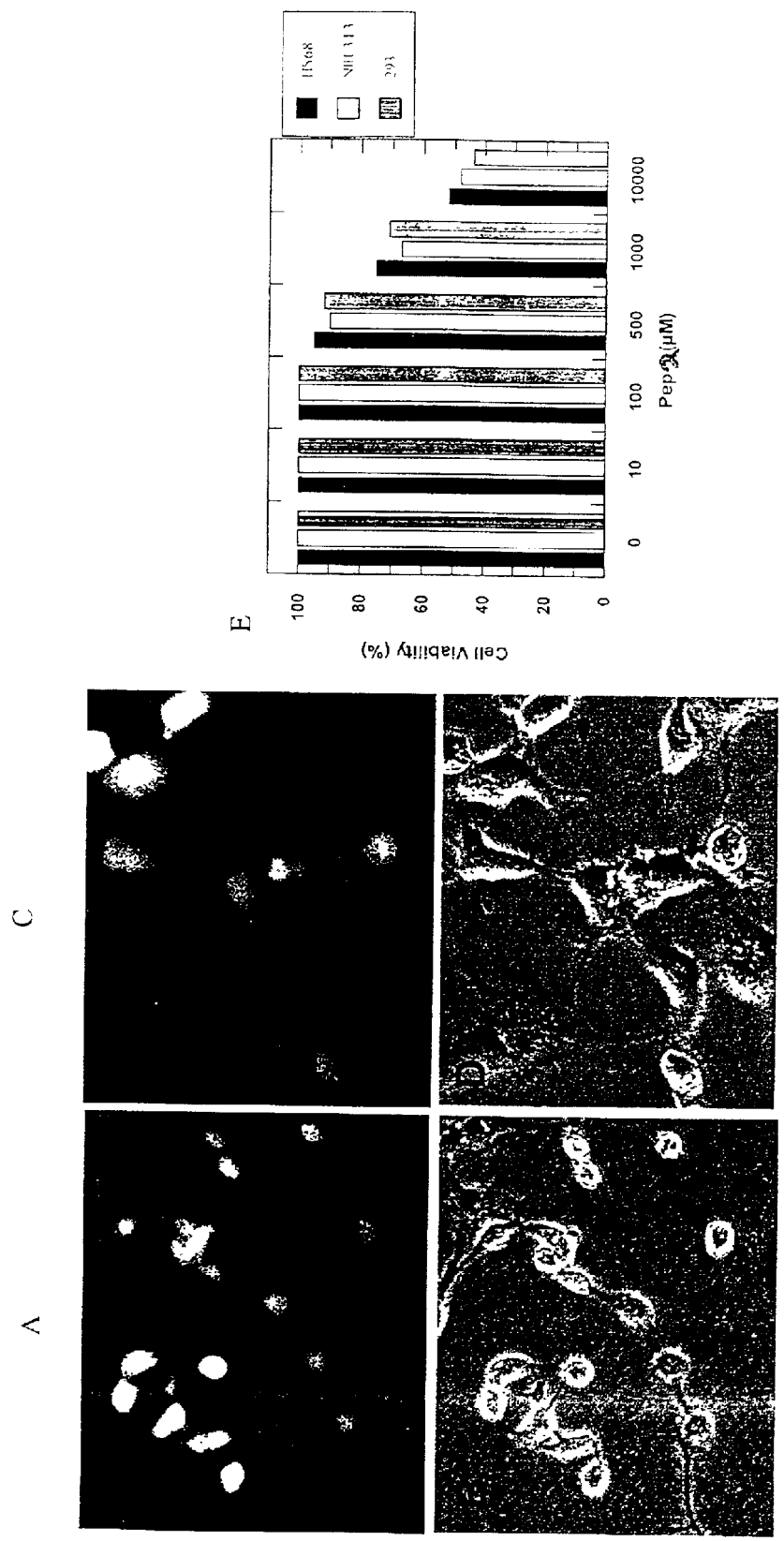
FIG. 16 shows the cellular localiztion and cytotoxicity of Pep-2. HS68 cells were incubated with 1 micromolar Pep-2: (A and B) for 10 min at 37 degrees C. and (C and D) for 30 min at 4 degrees C. (E) Toxicity of Pep-2 in different cell lines (HS-68, NIH 3T3, and 293) quantified by MTT staining after two days of incubation.

As to the conformational state of the peptide when interacting with lipids, it appears from CD and FTIR observations that it is mainly based on a β-type structure at least for high peptide/lipid ratios (FIGS. 14 and 15). In fact, the situation is more puzzling and for clarity reasons the detailed description will be restricted to peptide [1].

For this peptide, on the basis of FTIR observations made on transferred monolayers at a peptide/lipid ratio of 1 in mole per mole, it appeared that the major structure was of β-type whatever the lipid (DOPC, DOPG, DPPC and DPPG). However, an analysis of the compression isotherms of peptide containing lipid monolayers revealed an unusual behavior and in the case of DOPC and DOPG an unexpected strong deviation from additivity of the mean molecular area. This prompted us to analyze in detail, using FTIR spectroscopy, a possible concentration dependence (variation of the peptide/lipid ratio) of the peptide structure. Clearly, with DOPG an α to β transconformation occurs when the peptide/lipid ratio is varied from 0.05 to 0.2. In this ratio range the same transconformation occurs with DOPC but in a lesser extent and no transconformation could be detected with DPPC and DPPG. This is in line with AFM observations made an transferred monolayers and which showed major changes upon varying the peptide/lipid ratio of the nature of the particles embedded in the monolayers. In addition, these changes, especially those of the sizes of the particles, are consistent with an α to β transition (Van Mau et al. (1999), J. Membrane Biol., 167, 241; Vié et al., submitted).

F. Conclusion

Peptides issued from the association of a hydrophobic sequence with a hydrophilic one act as efficient carriers facilitating the cellular internalization of drugs and/or nucleic acids with final nuclear or cytoplasmic localizations and the carried molecules show the expected biological activity. The carried molecules can be either covalently linked (small organic molecules or oligonucleotides) or form complexes (RNA or DNA) with the vector. It appears that the hydrophobic domain of the vector peptides also participate to the lipid recognition process. The mechanism involved in the membrane translocation process is still on question since the peptide are highly versatile. The β-type structure seems to be strongly involved in the translocation process since this conformational state is favored by the presence of lipids. However, on the basis of the conformational behavior observed in some lipids, especially the finding of a concentration dependent α→β transconformation it is tempting to assume that the former conformational state is also involved in this process, at least for the covalent form. In the case of the translocation of a complex the peptide conformation has to be identified since the presence of a peptide-rich complex will modify the local peptide concentrations.

Example 3

Design and Characterization of the Pep-2 Peptide Vector

The rationale in the design of the novel peptide vector, Pep-2, for efficient protein delivery into cells was to satisfy two major requirements: the ability to cross cell membranes and high affinity for protein sequences. To this aim, we elaborated a 21 residue peptide, designated Pep-2 (KETWWETWWTEWSQPKKKRKV-cya; SEQ ID NO:7), consisting of three domains: (1) a hydrophobic Trp-rich motif containing five Trp-residues (KETWWETWWTEW (SEQ ID NO:32)), required for efficient targeting to the cell membrane and for forming hydrophobic interactions with proteins, (2) a hydrophilic Lys-rich domain (KKKRKV (SEQ ID NO:33)) derived from the NLS of SV40 large T antigen, required to improve intracellular delivery and solubility of the peptide vector, and (3) a spacer domain (Ser-Gln-Pro), separating the two domains mentioned above, containing a Pro residue, which improves the flexibility and the integrity of both the hydrophobic and the hydrophilic domains. Peptides were acetylated at their N-terminus and synthesized with a cysteamine group at their C-terminus, so as to enable coupling of fluorescent probes (for example, FITC), useful for cellular localization of the peptide. We first investigated the ability of Pep-2 to penetrate into cells and characterized its subcellular localization. In standard cell culture conditions, Pep-2 localizes rapidly, in less than min, to the nucleus of human HS68, murine NIH 3T3 fibroblasts or cos cells (FIG. 6A). Similar experiments, performed by incubating cells for 30 min at 4° C. or in the presence of okadaic acid (1 $\mu$M) prior to transfection, yielded essentially the same result, indicating that Pep-2 internalization is independent of normal endocytosis (FIG. 6B).

A third, major consideration to be considered in the design of any delivery system is toxicity of the transfection vector. As such we determined the degree of toxicity of Pep-2 on different cell lines (HS68, NIH 3T3 and 293) and found that no toxicity was observed at Pep-2 concentrations up to 100 $\mu$M, whilst cell viability was only decreased by about 10% for a Pep-1 concentration of 1 mM (FIG. 6C).

A. Formation of Peptide Vector/Protein Complexes

Figure 17:
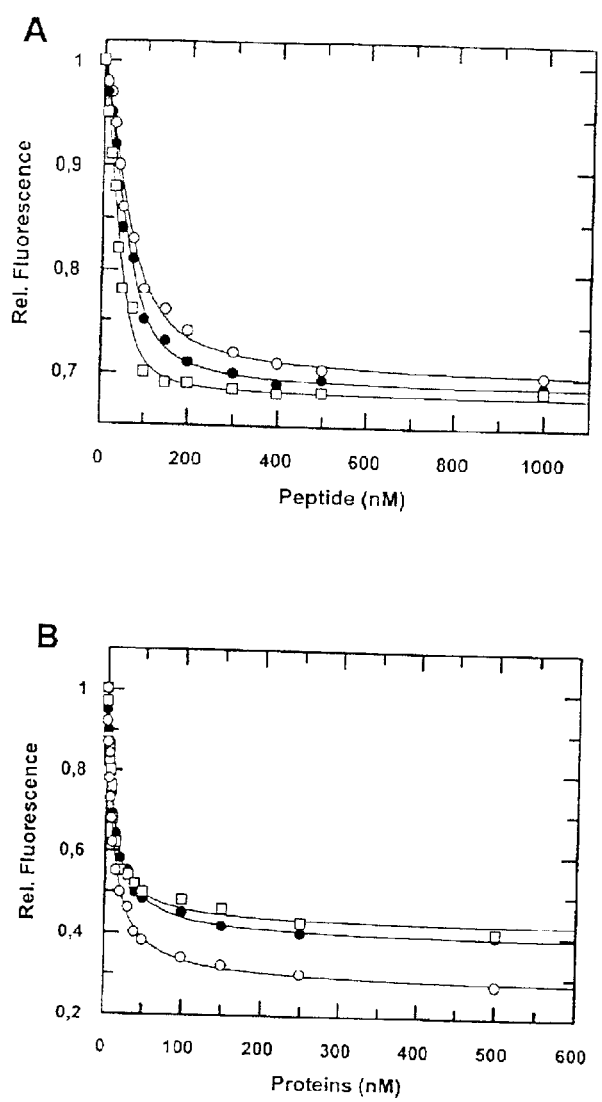
FIG. 17 shows the formation of Pep-2/peptide or Pep-2/protein complexes by monitoring the intrinsic tryptophan fluorescence of Pep-2 at 340 nm. (A) one micromolar Pep-2 titrated with increasing concentration of Pep-A in the presence (O) or absence ( ) of 200 mM NaCl or with increasing concentration of Pep-B (●). (B) one micromolar Pep-2 titrated with increasing concentration of beta-gal (O) or GFP ( ) in the presence (●) or absence ( ) of 200 mM NaCl.

We first examined to what extent Pep-2 could interact with a variety of different peptides and proteins. Interactions were quantified by intrinsic fluorescence spectroscopy, as Pep-2 contains five Trp residues in the hydrophobic domain, which represent sensitive probes for monitoring its interactions with peptides and proteins. For this study, we used two different peptides which are unable to the enter cells alone: a 32-mer peptide (Pep-A) derived from HIV-1 reverse transcriptase (Morris et al., J. Biol. Chem., 1999, 274, 24942–24946) and a 51-mer peptide (Pep-B) derived from human Cdc25C dual-specificity phosphatase (Morris et al., J. Biol. Chem., 2000, 275:28849–28857), as well as two proteins: the 30 kDa green fluorescent protein (GFP) and 119 kDa b-galactosidase (β-gal). The binding of peptides or proteins to Pep-2 induced a marked quenching of intrinsic tryptophan fluorescence, with saturating values of 36% and 65% for peptides and proteins, respectively (FIG. 17). These interactions induced a blue shift of the fluorescence emission maximum of 10 nm, (from 350 nm to 339 nm) suggesting that the Trp residues of Pep-2 interact directly with the peptides and proteins. Saturation took place at a concentration of about 200 nM for both peptides and of 50 nM for both GFP and β-Gal, values which are respectively 5-fold and 20-fold lower than the concentration of the Pep-2 (1 $\mu$M), suggesting that peptides and proteins interact strongly with more than one molecule of this peptide vector. Moreover, Pep-2 formed stable complexes with peptides and proteins in the presence of high salt concentrations (200 mM NaCl), revealing that binding of Pep-2 mainly involves hydrophobic contacts (FIG. 17). In contrast, in the absence of other peptides and proteins, the fluorescence of Pep-2 varied linearly with its concentration up to a millimolar concentration, indicating that Pep-2 does not self-associate in the conditions used for in vitro titration or in cell delivery experiments. When taking into account the number of Pep-2 molecules bound to peptides and proteins, the dissociation constants for these interactions were calculated to be in the range of 120±50 nM for both peptides and proteins. Taken together, these data clearly demonstrate that when Pep-2 is mixed with peptides or proteins in solution they rapidly associate through hydrophobic interactions into non-covalent stable complexes. Pep-2 displays a high affinity for different peptides and proteins, suggesting that these interactions are entirely independent of a specific peptidyl sequence.

B. Pep-2 Promotes Rapid Protein and Peptide Delivery into Different Cell Lines.

Figure 18:
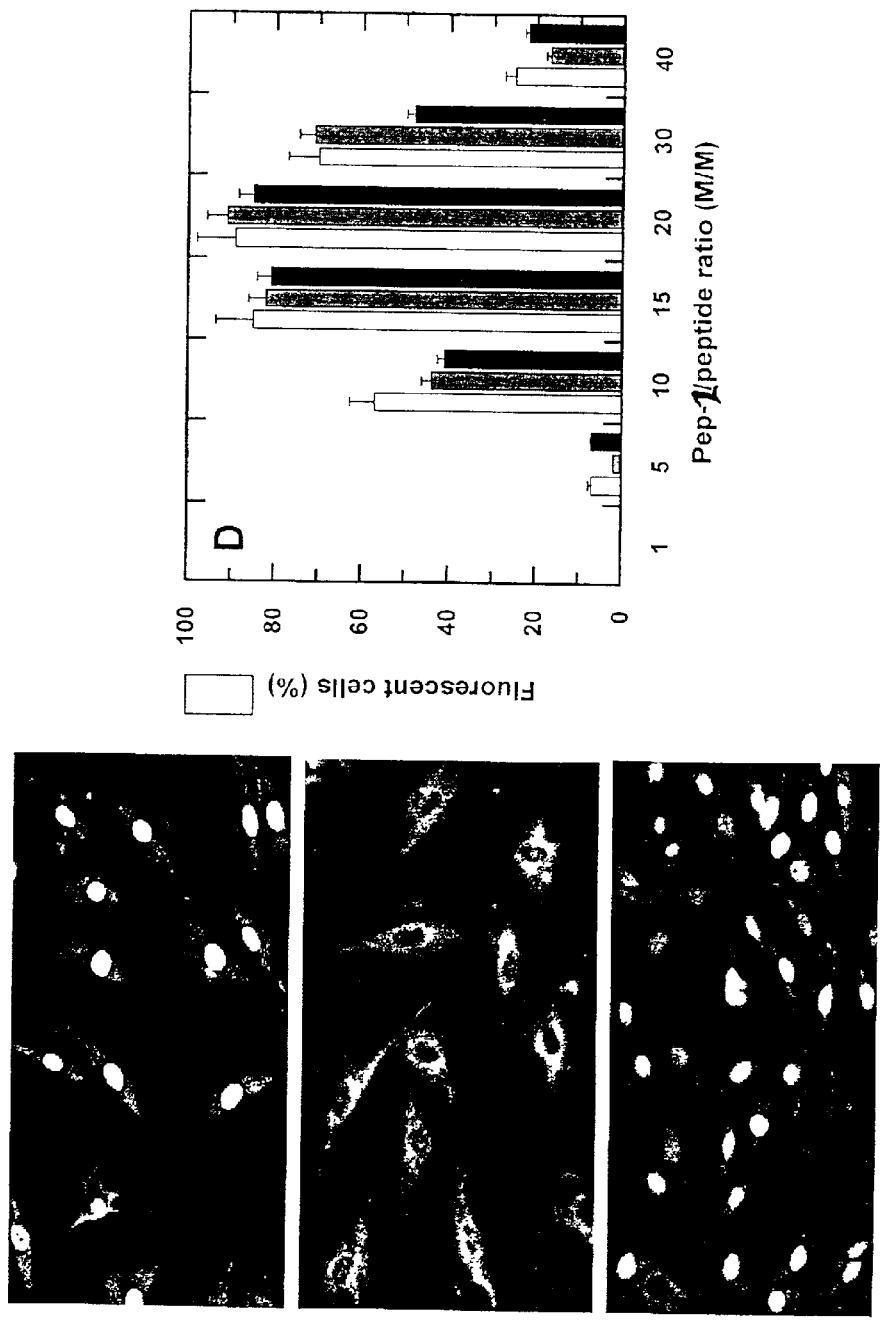
FIG. 18 shows the efficiency of Pep-2-mediated delivery of fluorescently-labeled peptides into human fibroblasts. (A) Pep-2-mediated delivery of Pep-A at 37 degrees C., (B) Pep-2-mediated delivery of Pep-B at 37 degrees C., (C) Pep-2-mediated delivery of Pep-A at 4 degrees C., (D) concentration dependence of Pep-2-mediated delivery of Pep-A. The efficiency of transfection was determined by counting fluorescent cells. Experiments were performed in the presence (dark bars) or absence (open bars) of serum and at 4 degrees C. (dashed bars).

We next evaluated the ability of Pep-2 to deliver peptides and LMW and HMW proteins into a human fibroblastic cell line (HS-68) and Cos-7. FITC-labeled Pep-A (51-mer) and Pep-B (32-mer) at a concentration of $5\ 10^{-8}$ M were incubated with different concentrations of Pep-2 from $5\ 10^{-8}$ M (ratio 1/1) to $2\ 10^{-6}$ M (ratio 40/1), in serum-free cell culture medium for 30 minutes at 37° C. Cultured cells 0.5 to $1\times10^6/35$ mm$^2$ were then overlaid with the preformed Pep-2/peptide complexes for 30 minutes in the presence or absence of FCS. Complexes were formed prior to addition of FCS to avoid interactions between Pep-2 and serum proteins. Following this transfection step, fresh DMEM supplemented with serum was added to the cells for another 30 minutes, after which cells were extensively washed, and examined by fluorescence microscopy. As shown in FIG. 18A, incubation of cells with Pep-2/Pep-A (an NLS-containing peptide) at a molar ratio of 20/1 promoted internalization of fluorescent peptide and its localization to the nucleus in more than 90% of the cells. In contrast, Pep-B, which does not contain an NLS motif, was mainly localized to the cytoplasm (FIG. 18B). These results clearly show that Pep-2 can efficiently deliver long peptides (30–50 mers) into cells without perturbing their proper intracellular localization. Moreover this internalization process does not require covalent coupling or denaturation procedures. Maximal transfection efficiency was obtained for a molecular ratio of 20/1 for both peptides, and no transfection was observed for a ratio lower than 5/1, indicating that the binding of a minimal threshold number of Pep-2 molecules to the target peptide is required for its intracellular delivery (FIG. 18D). Conversely, we observed a large decrease in the efficiency of transfection at a ratio greater than 30/1, which may be explained by either precipitation or aggregation of Pep-2/peptide complexes to the cell membrane. Remarkably, similar results were obtained when transfections were performed at 4° C., suggesting that, as for Pep-2 alone, the internalization process is not dependent on the endosomal pathway (FIG. 18C). From these data we infer that one fraction of Pep-2 molecules forms direct contacts with peptides and is required for their entrapment, whereas another fraction would interact with the cell membrane be involved in the translocation process. Finally, we evaluated the effect of serum in the cell culture medium on the efficiency of peptide transfection. As shown in FIG. 18C, the efficiency of Pep-2-mediated peptide delivery was not affected by the presence of serum (FCS 10%), which renders Pep-2 technology even more attractive for future in vitro and in vivo applications.

To investigate protein delivery we chose to monitor cell delivery of three very different types of proteins: 30 kDa GFP, 119 kDa β-Gal, and specific antibodies. GFP and β-Gal proteins at $5\ 10^{-8}$ M were incubated for 30 minutes at 37° C. with different concentrations of Pep-2 varying from $5\ 10^{-7}$ M to $5\ 10^{-5}$ M, then overlaid onto cultured cells for 1 hour. Cells were then extensively washed prior to observation and the efficiency of protein delivery was determined by counting fluorescent cells or by monitoring enzymatic β-galactosidase activity by X-Gal staining. In both cases, more than 80% efficiency was obtained for a molar ratio of Pep-1/protein of 40:1.

Figure 19:
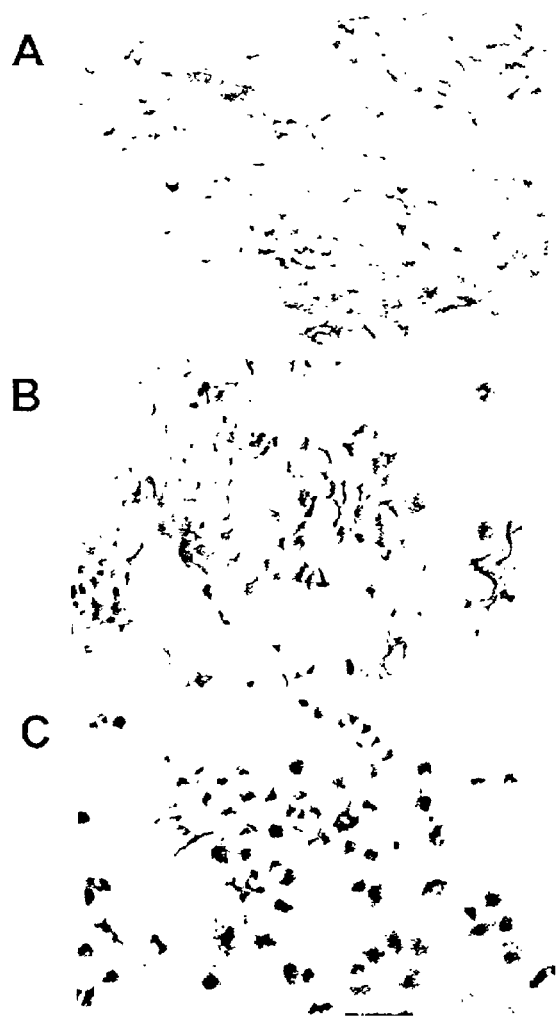
FIG. 19 shows Pep-2-mediated delivery of proteins into mammalian cells. The efficiency of transfection was determined by counting fluorescent cells or blue stained cells. (A) Control of beta gal in the absence of Pep-2, (B) Pep-2 delivery of beta gal at 37 degrees C., (C) Pep-2 delivery of beta gal at 4 degrees C., (D) Pep-2 delivery of GFP at 37 degrees C. (E) concentration dependent Pep-2 delivery of GFP. Experiments were performed in the absence (open bars) or presence (dark bars) of serum.
Figure 19:
Figure 19:
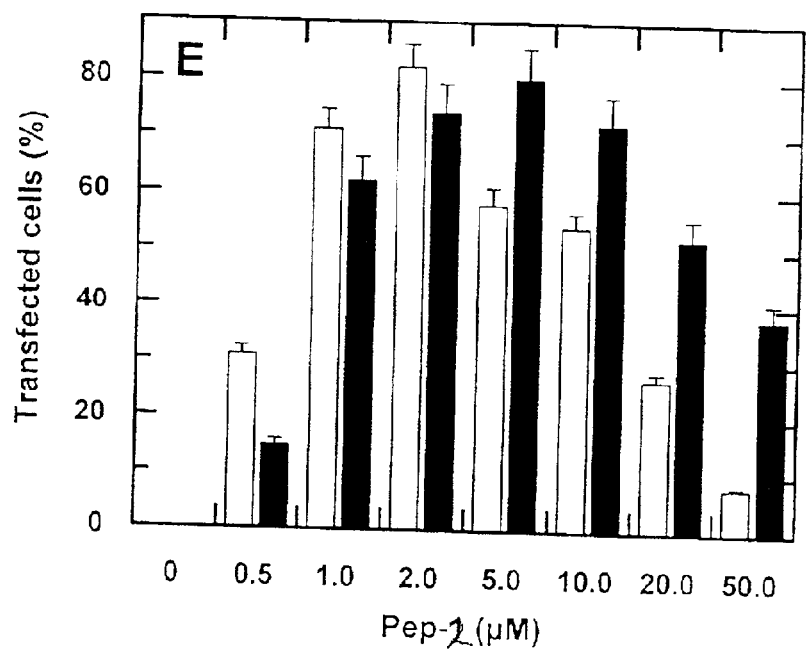

All cells exhibited strong and uniform β-Gal activity (FIG. 19B) and more than 80% of the cells contained fluorescent GFP staining in their cytoplasm (FIG. 19D). Most notably, the presence of Pep-2 did therefore not alter the enzymatic activity of β-Galactosidase upon delivery into cells. Moreover, as for peptides, the efficiency of protein delivery was not affected by the presence of 10% FCS, and no protein delivery was observed for concentrations of Pep-2 lower than $0.5\ 10^{-6}$ M or greater than $50\ 10^{-6}$ M (FIG. 19E). Finally, as shown in FIG. 19C, high transfection of β-Gal was equally observed when transfection was performed at 4° C., again supporting the idea Pep-2-mediated transfection is independent of the endosomal pathway.

Figure 20:
FIG. 20 shows Pep-2-mediated antibody delivery into mammalian cells. Two different FITC-conjugated antibodies, a monoclonal anti-beta-actin (A) and an anti-Lamp-1 (B) were used at a concentration of 0.1 micromolar and incubated with 5 micromolar Pep-2 for 30 min at 37 degrees C., then overlaid onto cultured cells for 1 h. Cells were then extensively washed and observed by fluorescence microscopy.
Figure 20:

As we demonstrated that Pep-2 did not affect the proper cellular localization of peptides, we verified whether this was also true for larger proteins. To this aim, we investigated the subcellular localization of FITC-conjugated antibodies following Pep-2-mediated delivery. Two different FITC-conjugated antibodies, anti-Lamp-1, which recognizes the Lysosome-Associated Membrane Protein 1 (LAMP-1), and monoclonal anti β-Actin. Antibodies were used at a 1/500 dilution and incubated with different concentrations of Pep-2, as described for GFP and β-Gal delivery. As shown in FIG. 20, characteristic labeling of both actin and lysosomes were observed, confirming that Pep-2 is able to deliver antibodies into cells, without modifying their ability to recognize antigens within cells. The best transfection results for both antibodies were obtained with Pep-2 at a concentration of $1.0\ 10^{-5}$ M.

Our observation that Pep-2 is able to promote delivery and proper localization of two different antibodies to their target antigens confirms that although Pep-2 alone localizes to the nucleus, it does not influence the subcellular localization of the proteins it delivers. In agreement with these data, we have tested a wide variety of antibodies, and always observed their proper intracellular localization. Taken together, our data suggest that Pep-2 mediated technology would be of great use to target cellular events, and strongly support the use Pep-2 as a powerful tool to deliver therapeutic antibodies or proteins into cells.

Example 4

Peptide Vector Design and Characterization in the Context of Protein Delivery

Peptide vectors in this embodiment were designed for having the ability to cross cell membranes and high affinity for protein sequences. Preferred peptide embodiments of the invention contain three domains: (1) a hydrophobic domain that includes three to five tryptophan (Trp) residues, to promote efficient crossing of the cell membrane and the formation of hydrophobic interactions with proteins, (2) a hydrophilic cation-rich domain to improve cell delivery and solubility of the peptide vector, and (3) these two domains are separated by a spacer domain containing a proline (Pro) or glutamine (Gln) residue. The sequence of the different peptides are reported in the following table.

| Peptide Sequences | |
|---|---|
| Pep-1-Cya (SEQ ID NO:1) | Tyr Gly Phe Lys Lys Arg Arg Trp Ser Gln Pro Lys Glu Thr Trp Glu Thr Trp Trp Thr Glu |
| Pep-1.1-Cya (SEQ ID NO:2) | Tyr Gly Phe Lys Lys Arg Arg Gln Pro Thr Trp Trp Glu Thr Trp Trp Thr Glu |
| Pep-1.2-Cya (SEQ ID NO:3) | Tyr Gly Phe Lys Lys Arg Arg Gln Thr Trp Trp Glu Thr Trp Trp Thr Glu |
| Pep-1.3-Cya (SEQ ID NO:34) | Tyr Gly Phe Lys Lys Arg Arg Gln Pro Thr |
| Pep-1.4-Cya (SEQ ID NO:35) | Thr Trp Trp Glu Thr Trp Trp Thr Glu |
| Pep-2 (SEQ ID NO:7) | Lys Glu Thr Trp Trp Glu Thr Trp Trp Thr Glu Trp Ser Gln Pro Lys Lys Lys Arg Lys Val |
| Pep-2-Cya (SEQ ID NO:7) | Lys Glu Thr Trp Trp Glu Thr Trp Trp Thr Glu Trp Ser Gln Pro Lys Lys Lys Arg Lys Val |
| Pep-2.1-Cya (SEQ ID NO:8) | Lys Glu Thr Trp Trp Glu Thr Trp Trp Thr Glu Trp Ser Gln Pro Lys Lys Arg Lys Val |
| Pep-2.2-cya (SEQ ID NO:9) | Lys Glu Thr Trp Trp Glu Thr Trp Trp Thr Glu Ala Ser Gln Pro Lys Lys Arg Lys Val |
| Pep-2.3-Cya (SEQ ID NO:10) | Lys Glu Thr Trp Trp Glu Thr Trp Trp Glu Thr Trp Ser Gln Pro Lys Lys Lys Arg Lys Val |
| Pep-2.4-Cya (SEQ ID NO:11) | Lys Glu Thr Trp Trp Glu Thr Trp Thr Trp Ser Gln Pro Lys Lys Lys Arg Lys Val |
| Pep-2.5-cya (SEQ ID NO:12) | Lys Trp Trp Glu Thr Trp Trp Glu Thr Trp Ser Gln Pro Lys Lys Lys Arg Lys Val |
| Pep-2.6-Cya (SEQ ID NO:5) | Lys Lys Lys Arg Lys Val Lys Glu Thr Trp Trp Glu Thr Trp Trp Glu Thr Val |
| Pep-2.7-Cya (SEQ ID NO:6) | Lys Lys Lys Arg Lys Val Lys Pro Glu Thr Trp Trp Glu Thr Trp Trp Glu Thr Val |
| Pep-2.9-Cya (SEQ ID NO:36) | Lys Glu Thr Trp Trp Glu Thr Trp Trp Glu Thr Trp Ser Gln Lys Lys Lys Arg Lys Val |
| Pep-2.10-Cya (SEQ ID NO:37) | Lys Glu Thr Trp Trp Glu Thr Trp Trp Thr Glu |
| Pep-2.11-Cya (SEQ ID NO:38) | Trp Ser Gln Pro Lys Lys Lys Arg Lys Val |
| Pep-2.12-Cya (SEQ ID NO:39) | Pro Lys Lys Lys Arg Lys Val |
| Pep-3-Cya (SEQ ID NO:40) | Tyr Gly Phe Lys Lys Phe Arg Lys Pro Trp Thr Trp Trp Glu Thr Trp Trp Thr Glu |
| Pep-4.1-Cya (SEQ ID NO:41) | Lys Thr Trp Trp Glu Thr Trp Trp Glu Thr Ala Ser Gln Pro Lys Lys Arg Lys Val |
| Pep-4.2-Cya (SEQ ID NO:42) | Lys Thr Trp Trp Glu Thr Trp Trp Glu Thr Trp Ser Gln Pro Lys Lys Arg Lys Val |

A. Drug, Peptide, and Protein Delivery into Different Cell Lines

We evaluated the ability of peptides designed according to principles described herein, as well as variants thereof, to deliver peptides and proteins into HS-68 and NIH 3T3 cell lines. Peptide delivery was performed with a 32 mer peptide (peptide B), and in some cases a 52 mer peptide (peptide A). The peptides were fluorescently labeled. Peptides ($5.0 \times 10^{-8}$M or $5.0 \times 10^{-7}$M) were incubated with one micromolar vector peptide in cell culture medium in the absence of serum for 30 min. Cultured cells (0.5 to $1.0 \times 10^6$) were then overlaid with the preformed peptide/vector peptide complexes in 500 µL DMEM for one hour in the presence or absence of FCS. Complexes were formed prior to addition of FCS to avoid interactions between ep-vector and serum proteins. Following this transfection step, fresh DMEM supplemented with serum was added for another hour. Then cells were extensively washed, fixed and analyzed by by fluorescence microscopy.

To investigate protein delivery we tested the delivery into cells of the fluorescent protein GFP. The protein was incubated with peptide at a molar ratio of 1:20, followed by overlay of the complex onto cultured cells. This was followed by incubation for 1 h. Then cells were extensively washed and fixed with formalin before observation.

For investigation of drug delivery, we used the naphthalene derivatives ANS and Bis-ANS, which have intrinsic fluorescence. The drugs was incubated with peptide at a molar ratio of 1:20, followed by overlay of the complex onto cultured cells. This was followed by incubation for 1 h. Then cells were extensively washed and observed by microscopy.

B. Results: Comparison of Vector Properties of Peptides

The results of the experiments testing the transfection properties of the peptides are presented as a table in which the sequences are aligned for optimal comparison:

| Peptide | Sequence | Drug | Pro | Pep |
|---|---|---|---|---|
| Pep-1-cya | Tyr Gly Phe Lys Lys Arg Arg Trp Ser Gln Pro Lys Glu Thr Trp Glu Thr Trp Trp Thr Glu (SEQ ID NO:1) | 5% | 80% | 80% |
| Pep-1.1-cya | Tyr Gly Phe Lys Lys Arg Arg Gln Pro Thr Trp Trp Glu Thr Trp Trp Thr Glu (SEQ ID NO:2) | 5% | 60% | 80% |
| Pep-1.2-cya | Tyr Gly Phe Lys Lys Arg Arg Gln Thr Trp Trp Glu Thr Trp Trp Thr Glu (SEQ ID NO:3) | 5% | 80–90% | 80% |
| Pep-3-cya | Tyr Gly Phe Lys Lys Phe Arg Lys Pro Trp Thr Trp Trp Glu Thr Trp Trp Thr Glu (SEQ ID NO:40) | 50–70% | 5% | 50% |
| Pep-1.3-cya | Tyr Gly Phe Lys Lys Arg Arg Gln Pro Thr (SEQ ID NO:34) | — | — | — |
| Pep-2.11-cya | Trp Ser Gln Pro Lys Lys Lys Arg Lys Val (SEQ ID NO:38) | — | — | — |
| Pep-2.12-cya | Pro Lys Lys Lys Arg Lys Val (SEQ ID NO:39) | — | — | — |
| Pep-2.6-cya | Lys Lys Lys Arg Lys Val Lys Glu Thr Trp Trp Glu Thr Trp Trp Glu Thr Val (SEQ ID NO:5) | — | 20% | 30% |
| Pep-2.7-cya | Lys Lys Lys Arg Lys Val Lys Pro Glu Thr Trp Trp Glu Thr Trp Trp Glu Thr Val (SEQ ID NO:6) | — | 10–20% | 20–30% |
| Pep-1.4-cya | Thr Trp Trp Glu Thr Trp Trp Thr Glu (SEQ ID NO:35) | — | — | — |
| Pep-2.10-cya | Lys Glu Thr Trp Trp Glu Thr Trp Trp Thr Glu (SEQ ID NO:37) | — | — | — |
| Pep-2-cya | Lys Glu Thr Trp Trp Glu Thr Trp Trp Thr Glu Trp Ser Gln Pro Lys Lys Lys Arg Lys Val (SEQ ID NO:7) | 20% | 90–100% | 90–100% |
| Pep-2 | Lys Glu Thr Trp Trp Glu Thr Trp Trp Thr Glu Trp Ser Gln Pro Lys Lys Lys Arg Lys Val (SEQ ID NO:7) | 5% | 5% | 5% |
| Pep-2.1-cya | Lys Glu Thr Trp Trp Glu Thr Trp Trp Thr Glu Trp Ser Gln Pro Lys Lys Arg Lys Val (SEQ ID NO:8) | 20% | 70% | 80% |
| Pep-2.2-cya | Lys Glu Thr Trp Trp Glu Thr Trp Trp Thr Glu Ala Ser Gln Pro Lys Lys Arg Lys Val (SEQ ID NO:9) | 5% | 30% | |
| Pep-2.3-cya | Lys Glu Thr Trp Trp Glu Thr Trp Trp Glu Thr Trp Ser Gln Pro Lys Lys Lys Arg Lys Val (SEQ ID NO:10) | 30% | 50–70% | 60–70% |
| Pep-2.9-cya | Lys Glu Thr Trp Trp Glu Thr Trp Trp Glu Thr Trp Ser Gln Lys Lys Lys Arg Lys Val (SEQ ID NO:36) | — | — | 5% |
| Pep-2.4-cya | Lys Glu Thr Trp Trp Glu Thr Trp Thr Trp Ser Gln Pro Lys Lys Lys Arg Lys Val (SEQ ID NO:11) | 5% | 20–30% | 60% |
| Pep-2.5-cya | Lys Trp Trp Glu Thr Trp Trp Glu Thr Trp Ser Gln Pro Lys Lys Lys Arg Lys Val (SEQ ID NO:12) | 5% | 5% | 50–60% |
| Pep-4.1-cya | Lys Thr Trp Trp Glu Thr Trp Trp Glu Thr Ala Ser Gln Pro Lys Lys Arg Lys Val (SEQ ID NO:41) | Aggr. | Aggr. | Aggr. |
| Pep-4.2-cya | Lys Thr Trp Trp Glu Thr Trp Trp Glu Thr Trp Ser Gln Pro Lys Lys Arg Lys Val (SEQ ID NO:42) | Aggr. | Aggr. | Aggr. |

1. Peptide and Protein Transfection

The comparison of the peptides as transfection agents for small compounds (drugs), proteins, and peptides, demonstrates principals on which peptide transfection agents of the present invention can be designed. With regard to the hydrophobic domain, it is clear from the results of transfection experiments using Peps-1.4 and -2.10, the hydrophobic domain alone is not sufficient to transfect drugs, proteins, or peptides. It is not a requirement that all hydrophobic, in this instance tryptophan, residues, occur in pairs, as can be seen from the high transfection of peptides and proteins by Pep-1, which comprises only a single Trp pair. It does appear to be important however, to preserve the spacing between hydrophobic loci, as can be seen from the poor transfection efficiencies of Pep-2.4 (which can be directly compared with Pep-2.3). Also, the sequence Thr-Glu (amino to carboxy direction) is preferred over Glu-Thr, as can be seen from the difference in transfection efficiencies between Peps-2 and -2.3. While excellent transfection efficiencies are obtained for peptides and proteins using peptides having charged and polar residues preceding the hydrophobic domain, e.g., the "Lys-Glu-Thr" sequence of Pep-2, the loss of some of these charged and polar residues, in particular "Lys-Glu" can result in somewhat less effective vectors, at least for protein transfection (comparing Pep-1.1 to Pep 1). It is also notable that peptide vectors having the hydrophobic domain at the N-terminus can be rendered ineffective by the loss of N-terminal charged and polar residues due at least in part to aggregation and poor solubility of the peptides (Peps-4.1 and 4.2).

For the hydrophilic domain, lysine (Lys) is a preferred amino acid, however, the substitution of arginine (Arg) in at least some of the positions appears not to affect transfection efficiencies (the highly effective protein and peptide vectors Peps-1, -1.1, and 1.2 have, for example, two Lys and two Arg residues). Having four rather than five positively charged residues does not appear to reduce transfection effieciency of proteins (the highly effective protein and peptide vectors Peps-1, -1.1, and 1.2 have, for example, four rather than five positively charged residues). For peptides in which the hydrophilic domain is N-terminal to the hydrophobic domain, it can be advantageous to have non-charged N-terminal amino acids (for example Tyr-Gly-Phe) that precede the hydrophilic domain (see, for example, Peps-1, 1.1, and 1.2, versus Peps-2.6 and -2.7). The hydrophilic domain alone or in combination with a spacer, is ineffective in transfecting drugs, proteins, or peptides (see Peps-2.11, -2.12, and 1.3).

The spacer domain, comprising amino acids that disrupt alpha helices such as Gly, Gln, Ser, and Pro, contributes to the efficiency of transfection of peptides and proteins. Glutamine (Gln) is at least as effective as proline (Pro) in optimizing the function of the peptides (comparing Peps-1.1 and 1.2).

The addition of a cysteamine group is very important for high transfection efficiencies, as can be observed by the dramatic difference in transfection efficiency between Peps-2 and 2.8 that differ only by this group. Because the assay tested for transfection of nonconjugated peptides and proteins, the free sulfhydryl of this group may be relevant to the formation of complexes that include the peptide transfection agent and the peptide or protein to be transfected. In this regard, it can be possible to substitute other moieties comprising sulfhydryl groups, including but not limited to the amino acid cysteine in peptide transfection agents of the present invention.

2. Drug Transfection

Pep-3 is the most efficient peptide transfection agent for transfecting small compounds such as drugs. This compound share most features with other peptide transfecting agents, with the exception of a hydrophobic amino acid (Phe) that occurs between charged residues in the hydrophilic domain.

C. Materials

Dulbecco's modified Eagle's Medium (DMEM) and Phosphate Buffered Saline (PBS) were from BioWhittaker. L-Glutamine, Penicillin, Streptomycin, and Trypsin were from Imperial Laboratories. Fetal Calf Serum was from GIBCO BRL. GFP was a gift but is commercially available from numerous sources.

D. Peptide Synthesis and Analysis

Peptides were synthesized by solid phase peptide synthesis (Vidal et al. (1996), J. Peptide Sci., 2, 125–133; Méry et al. (1993), Int. J. Peptide Prot. Res., 42, 44–52. ) using AED1-expensin resin with a 9050 Pepsynthetizer (Millipore UK) according to the Fmoc/Buc method, as already described (Mery et al (1993). Peptides were purified by semi-preparative HPLC and identified by electrospray mass spectrometry and amino acid analysis (Mery et al. (1993); Morris et al. (1997), Nucleic Acids Res., 25, 2730–2736).

Example 5

Transduction of p27(kip1) into Cell Lines Induces Cell Cycle Arrest in G1

The protein inhibitor p27$^{Kip1}$ binds to and inhibits Cdk/cyclin complexes involved in the G1/S transition, such as Cdk2/cyclin E and Cdk2/cyclin A complexes. We have used a peptide transfection agent to deliver p27$^{kip1}$ protein into cells and to investigate its in vivo biochemical mechanism. We demonstrated that Pep-2 is able to deliver the full-length active form of p27$^{kip1}$, which induced a substantial arrest of the cell cycle progression in G1.

A. Procedure p27(kip1) was expressed in E coli, and purified as a his-tagged protein. Pep-2/p27kip1 complexes were formed in PBS (500 μl of DMEM containing 50 nM of protein and 0.1 μM of Pep-2) and incubated for 30 min at 37° C. Jurkat T and WI 38 cells grown to 75% confluency were then overlaid with these preformed complexes. After 1 hr incubation at 37° C., fresh DMEM supplemented with 10% foetal calf serum was added to the cells, without removing the overlay of Pep-2/p27$^{Kip1}$, and cells were returned to the incubator for another 30 h. Experiments were performed on both non-synchronized and synchronized cells. The number of cells arrested in G1 was determined both by FACS analysis and BrDu incorporation.

B. Results

Figure 21:
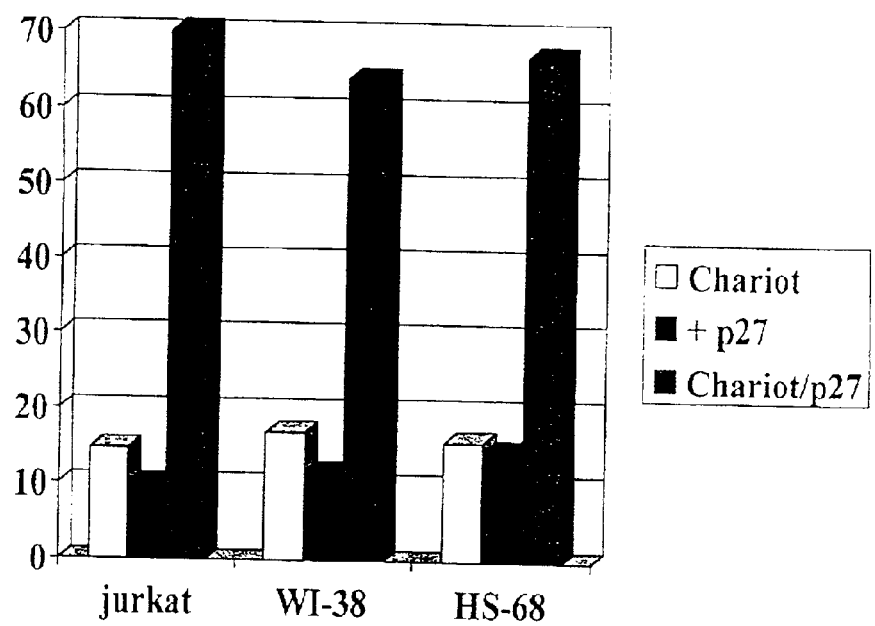
FIG. 21 shows the effect on the cell cycle of Pep-2 delivery of p27 (kip1) protein into Jurkat and WI38 cells. The number of cells in the G1 phase was determined by BrDU incorporation.
Figure 22:
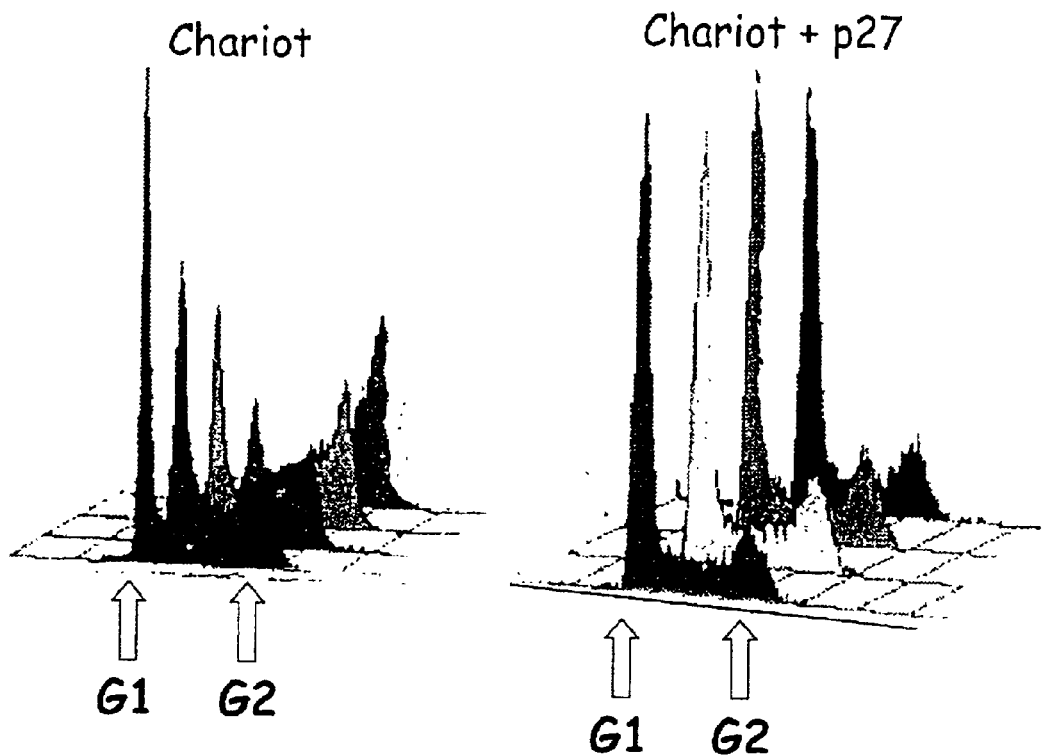
FIG. 22 shows the effect on the cell cycle of Pep-2 delivery of p27 (kip1) protein into Jurkat and WI38 cells. The number of cells in the G1 phase was determined by FACs analysis.

We demonstrated that Pep-2 efficiently delivers p27$^{kip1}$ protein into 80 to 100% of cells. For both cell lines, we observed a cell cycle arrest in G1 following p27$^{kip1}$ delivery using Pep-2 (FIGS. 21 and 22). In the case of non-synchronized cells, more than 80% of the cells are arrested in G1 after 24 h. In the case of synchronized cells, the cell are immediately blocked in G1, after release from serum deprivation. Similar experiments performed with Pep-2 alone reveals that this vector has no effect on cell cycle progression.

Example 6

CHARIOT™: A Commercial Kit Embodiment

A. Components of the Kit

This embodiment of Chariot™ is based on the peptide known herein as "Pep-2" having SEQ ID NO:7 (see Example 3). This peptide works best with peptides, proteins, and antibodies, and as such is primarily to be marketed for this. Other peptide transfection agents of the present invention can be provided as an alternative to, or in addition to, that having SEQ ID NO:7.

The peptide vectors of the kit may further be provided conjugated with one or more other moieties, e.g., an acyl and/or cya coupling group. The kit may further be designed and promoted for use with a wide variety of adherent and nonadherent cell types, including 293, COS-7, HS-68, NIH 3T3, C2C12, Hela, CEM-SS, and HEPG2, with which it has been successfully tested. Speed is also promoted, with successful transfection determined in cultured mammalian cells within as little as 1 hour. As such, the kit is further promoted for use in bypassing gene transfection and expression, as this typically takes 12–80 hours to effect and detect. Low toxicity and stability are also promoted, as is the endosomal-independent nature of this transfection system, which allows successful transfections at 4° C. The peptide's action is further serum-independent, and fixation is optional making it ideal for in vivo studies.

While intended for non-covalent complexations and delivery of molecules, a peptide transfection agent having an optional cya coupling group offers the alternative or added utility of covalent coupling with another or additional functional groups. In this way, not only can the peptide transport non-covalently complexed compounds, but it can also transmit an intrinsic or covalently bound signal or effect as well. Thus, the peptide agent can be multifunctional.

The kits are marketed preferably in 25 or 100 reaction sizes amounts, and with useful guidelines for the size of the plates or dishes and the relative amount of reagent that should be used. For example, the following table is illustrative of what will accompany the kit:

| Plate | Chariot (ul) | # of Transfections per Kit (25 rxn kit) | # of Transfections per Kit (100 rxn kit) |
|---|---|---|---|
| 24-well | 2 | 75 | 300 |
| 12-well | 3.5 | 42 | 171 |
| 6-well | 6 | 25 | 100 |
| 60 mm | 20 | 7 | 30 |
| 100 mm | 50 | 3 | 12 |

| Component | Quantity 25 reactions | Quantity 100 reactions | Composition | Storage |
|---|---|---|---|---|
| Chariot Transfection Reagent | 150 μl | 600 μl | Chariot in H$_2$O and 0.5 mM TCEP | −20° C. for up to 6 months |
| PBS | 1 ml | 1 ml | 1.5 mM KH$_2$PO$_4$ 150 mM NaCl$_2$ 5 mM Na$_2$HPO$_4$ | −20° C. |
| β-galactosidase (Positive Control) 0.25 μg/μl | 5 μg | 5 μg | β-galactosidase in H$_2$O | −20° C. for up to 6 months |

B. Quality Control

The Chariot Transfection Reagent is tested functionally by protein and antibody delivery into three different cell lines (HS-68, NIH 3T3, and HeLa). Chariot Transfection Reagent is tested for the absence of bacterial and fungal contamination in cell culture media containing DMEM supplemented with 10% FBS. Chariot Transfection Reagent is determined to be non-cytotoxic at the recommended concentrations.

The kit is preferably supplied with Chariot Transfection Reagent in aqueous solution or in lyophilized form, a buffer, e.g. PBS, for resuspension, and an indicator protein such as purified β-galactosidase that is used as a positive control.

Instructions will note, as is standard in the art, the possibility for variation with cell lines and optimum transfection times. Recommendations for optimization will be made. Although the procedures have been optimized for adherent cells, the invention is also likely to be useful for suspension cells as well, especially if first transferred and adhered to a plate. The kit will also note the preferred seeding densities for the cells as per a chart or guide such as:

| Plate | surface area (mm$^2$) | seeding density | growth medium (ml) |
|---|---|---|---|
| 24-well | 200 | 0.05 × 10$^6$ | 0.5–1.0 |
| 12-well | 401 | 0.1 × 10$^6$ | 1–2 |
| 6-well | 962 | 0.3 × 10$^6$ | 3–5 |
| 60 mm | 2827 | 0.8 × 10$^6$ | 5 |
| 100 mm | 7854 | 2.2 × 10$^6$ | 10 |

C. Sample Protocols

1. Transfection protocol for 6-well or 35 mm plates.

These conditions are recommended as guidelines only. Efficient transfection may require optimization of reagent concentration, cell number and exposure time of cells to the Chariot-macromolecule complex. Conditions should also be optimized for each cell line and kept consistent to obtain reproducible results. This procedure has been optimized for the transfection of adherent cells.

| Plate | Surface Area (mm$^2$) | Seeding Density | Growth Medium (ml) |
|---|---|---|---|
| 24-well | 200 | 0.05 × 10$^6$ | 0.5–1.0 |
| 12-well | 401 | 0.1 × 10$^6$ | 1–2 |
| 6-well | 962 | 0.3 × 10$^6$ | 3–5 |

| Plate | Surface Area (mm²) | Seeding Density | Growth Medium (ml) |
|---|---|---|---|
| 60 mm | 2827 | $0.8 \times 10^6$ | 5 |
| 100 mm | 7854 | $2.2 \times 10^6$ | 10 |

1. In a six-well or 35-mm tissue culture plate, seed $0.3 \times 10^6$ cells per well in 3 ml of complete growth medium.

Note: Adjust the number of cells and volumes accordingly if using culture plates of different sizes. (See Table 1)

2. Incubate the cells at 37° C. in a humidified atmosphere containing 5% $CO_2$ until the cells are 40–50% confluent.

Note: Transfection efficiency may be sensitive to culture confluency, so it may be necessary to optimize cell density for each cell line.

3. Chariot is ready to use for protein and antibody transfections. For peptide or low molecular weight protein (<10 kDa) transfections this solution must be diluted 1:10 in $H_2O$.

4. For a reaction in a 6-well or 35 mm culture plate dilute the protein, peptide or antibody to be transfected into 100 µl of PBS. Make calculations for the dilutions according to the final transfection volume. (See Tables)

| Plate | PBS (µl) for macromolecule dilution |
|---|---|
| 24-well | 50 |
| 12-well | 100 |
| 6-well | 100 |
| 60 mm | 200 |
| 100 mm | 200 |

Protein: Use 0.25–1 µg of protein per transfection reaction.

Peptide: Use 100–500 ng of peptide or low molecular weight protein per transfection reaction.

Antibody: Use a 1/500, 1/1000, 1/2500 dilution of antibody. Make calculations for the dilutions according to the final transfection volume.

| Plate | Final Transfection Volume (µl) |
|---|---|
| 24-well | 200 |
| 12-well | 350 |
| 6-well | 600 |
| 60 mm | 2000 |
| 100 mm | 5000 |

It is necessary to make the Chariot-macromolecule complex in a concentrated solution. The solution will then be diluted to the final transfection volume after addition to the cells.

5. In a separate tube dilute the appropriate volume of Chariot into 100 µl sterile water. (See Table). At this stage sonication of the Chariot dilution is recommended, but not essential.

| Plate | Sterile $H_2O$ for Chariot dilution (µl) | Protein/Antibody* Volume of Chariot (µl) | Peptide/LMW Proteins** Volume of a 1/10 dilution of Chariot (µl) |
|---|---|---|---|
| 24-well | 50 | 2 | 2 |
| 12-well | 100 | 3.5 | 3.5 |
| 6-well | 100 | 6 | 6 |
| 60 mm | 200 | 20 | 20 |
| 100 mm | 200 | 50 | 50 |

*Depending on the sensitivity required for antibody detection, it may be necessary to increase the amount of Chariot used. This may result in aggregate formation.

**Chariot interacts, at least in part, via hydrophobic interactions. Each peptide or protein will have a different hydrophobicity. This is more apparent with small, lower molecular weight molecules, therefore the amount of Chariot may need to be increased.

6. Add the 100 µl macromolecule dilution to the 100 µl Chariot dilution. It is necessary to make the Chariot-macromolecule complex in a concentrated solution. The solution will then be diluted to the final transfection volume after addition to the cells.

7. Incubate at room temperature for 30 minutes to allow the Chariot-macromolecule complex to form.

8. Aspirate the medium from the cells to be transfected.

9. Wash the cells with PBS. (Optional)

10. Overlay the cells with the Chariot-macromolecule complex. Add 400 µl serum-free medium to the overlay to achieve the final transfection volume of 600 µl for a 6-well or 35 mm plate. Incubate at 37° C. in a humidified atmosphere containing 5% $CO_2$ for one hour. (See Table):

| Plate | Volume of Chariot-Macromolecule Complex (µl) | Serum-free Medium (µl) | Final Transfection Volume (µl) |
|---|---|---|---|
| 24-well | 100 | 100 | 200 |
| 12-well | 200 | 150 | 350 |
| 6-well | 200 | 400 | 600 |
| 60 mm | 400 | 1600 | 2000 |
| 100 mm | 400 | 4600 | 5000 |

11. Add 1 ml of complete growth medium to the cells. Do not remove the Chariot-macromolecule complex. Continue to incubate at 37° C. in a humidified atmosphere containing 5% $CO_2$ for 30 minutes to 2 hours.

| Peptide: | 0.5–1 hour |
|---|---|
| Proteins: | 1–2 hours |
| Antibodies: | 2 hours |

12. Process cells for observation or detection assays. Cells may be fixed or observed directly.

2. Transfection Protocol for Suspension Cells

These conditions are recommended as guidelines only. Efficient transfection may require optimization of reagent concentration, cell number and exposure time of cells to the Chariot-macromolecule complex. Conditions should also be optimized for each cell line and kept consistent to obtain reproducible results.

1. Use Table 1 as a guideline for the number of cells needed per transfection. The seeding density for adherent cells is also recommended for the suspension protocol.

2. The Chariot-macromolecule complex is assembled in the same manner as described for adherent cells. See Steps 3–7.

3. Collect the suspension cells by centrifugation at 200–400×g for 5 minutes. Remove the supernatant.
4. Wash the cells twice with 1×PBS.
5. Centrifuge at 200–400×g for 5 minutes to pellet the cells. Remove the supernatant.
6. Resuspend the cell pellet in the Chariot-macromolecule complex. Add serum-free medium to achieve the final transfection volume.
7. Incubate at 37° C. in a humidified atmosphere containing 5% $CO_2$ for one hour.
8. Add complete growth medium to the cells. Do not remove the Chariot-macromolecule complex. Continue to incubate at 37° C. in a humidified atmosphere containing 5% $CO_2$ for 30 minutes to 2 hours.
9. Process cells for observation or detection assays.

3. Transfection Protocol for 8-well Chamber Slide

These conditions are recommended as guidelines only. Efficient transfection may require optimization of reagent concentration, cell number and exposure time of cells to the Chariot-macromolecule complex. Conditions should also be optimized for each cell line and kept consistent to obtain reproducible results.

1. In an 8-well Chamber Slide seed $1\times10^4$ cells per well in 200 μl of complete growth medium.
2. Incubate the cells at 37° C. in a humidified atmosphere containing 5% $CO_2$ until the cells are 40–50% confluent. Note: Transfection efficiency may be sensitive to culture confluency, so it may be necessary to optimize cell density for each cell line.
2. Chariot is ready to use for protein and antibody transfection. For peptide or low molecular weight protein (<10 kDa) transfections this solution must be diluted 1:10 in $H_2O$.
3. Dilute the protein, peptide or antibody to be transfected into 10 μl of PBS. Make calculations for the dilutions according to the final transfection volume of 100 μl. Protein: Use 0.25–1 μg of protein per transfection reaction. Antibody: Use a 1/500, 1/1000, 1/2500 dilution of antibody. Peptide: Use 100–500 ng of peptide or low molecular weight protein per transfection reaction.
4. In a separate tube dilute 1 μl of Chariot (or 1 μl of a 1:10 dilution of Chariot for peptide/LMW protein transfections) into 10 μl of sterile water. At this stage sonication of the Chariot dilution is recommended, but is not essential.

\* Depending on the sensitivity for antibody detection, it may be necessary to increase the amount of chariot used. This may result in aggregate formation.

\*\* Chariot interacts, at least in part, via hydrophobic interactions. Each peptide or protein will have a different hydrophobicity. This is more apparent with small, lower molecular weight molecules, therefore the ammount of Chariot may need to be increased.

5. Add the 10 μl macromolecule dilution to the 10 μl Chariot dilution. It is necessary to make the Chariot-macromolecule complex in a concentrated solution. The solution will then be diluted to the final transfection volume after addition to the cells.
6. Incubate at room temperature for 30 minutes to allow the Chariot-macromolecule complex to form.
7. Aspirate the medium from the cells to be transfected.
8. Wash the cells with PBS. (Optional)
9. Overlay the cells with the 20 ∥l Chariot-macromolecule complex. Add 80 μl serum-free medium to the overlay to achieve the final transfection volume of 100 μl for each well of the 8-well Chamber slide.
10. Incubate at 37° C. in a humidified atmosphere containing 5% $CO_2$ for one hour.
11. Add 100–200 μl of complete growth medium to the cells. Do not remove the Chariot-macromolecule complex. Continue to incubate at at 37° C. in a humidified atmosphere containing 5% $CO_2$ for 30 minutes to 2 hours:

| Peptide: | 0.5–1 hour |
|---|---|
| Proteins: | 1–2 hours |
| Antibodies: | 2 hours |

12. Process cells for observation or detection assays. Cells may be fixed or observed directly.

C. β-Galactosidase Positive Control

β-Galactosidase is provided as a positive control protein for the Chariot transfection reagent. β-Galactosidase is an enzyme that hydrolyses β-galactosides, such as lactose and the artificial chromogen X-gal. When β-galactosidase hydrolyses X-gal it produces a blue color that can be visualized under a bright field microscope. A 119 kDa β-galactosidase protein is provided with the kit (25 reaction kit: 5 μg of protein at 0.25 μg/μl concentration, 100 reaction kit: 5 μg of protein at 0.25 μg/μl concentration).

This protein can be transfected into cultured mammalian cells following the protein transfection procedure. After transfection the cells may be stained to assay for the efficiency of the transfection.

β-Galactosidase Staining of 6 well or 35 mm plates:
1. Remove the growth medium from the transfected cells.
2. Rinse the cells with 3 times with 1 ml of 1×PBS.
3. Fix the cells with 1 ml of 1×Fixing solution for 5–10 minutes.
4. Prepare the stain solution.
5. Rinse the cells twice with 1 ml of 1×PBS.
6. Add 1 ml stain solution to the cells.
7. Incubate the cells at 37° C. for 30 min to 2 hours.
8. Check the cells under a microscope.
9. Calculate the percent of cells transfected with μ-galactosidase:

$$\frac{\text{Total \# of blue cells}}{\text{Total \# of cells}} \times 100 = \% \text{ transfection}$$

| 10X Fixing Solution | Stain Solution |
|---|---|
| 20% formaldehyde<br>2% glutaraldehyde<br>in 10X PBS | 4 mM potassium ferricyanide<br>4 mM potassium ferrocyanide<br>2 mM magnesium chloride<br>1 mg/ml X-gal (5-bromo-4-chloro-3-indolyl-<br>β-D-galactopyranoside) made up in 1X PBS |

All publications mentioned in the specification are indicative of the levels of skill of those skilled in the art to which the invention pertains. All references cited in this disclosure are incorporated by reference to the same extent as if each reference had been incorporated by reference in its entirety individually. One skilled in the art would readily appreciate that the present invention is well adapted to carry out the objects and obtain the ends and advantages mentioned, as well as those inherent. The methods and systsems described herein are exemplary and not intended as limitations on the scope of the invention. It will be readily apparent to one skilled in the art that varying substitutions and modifications may be made to the invention disclosed herein without departing from the scope and spirit of the invention.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other groups.

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

BIBLIOGRAPHY

U.S. Pat. No. 5,270,163 to Gold et al., issued Dec. 14, 1993.
U.S. Pat. No. 5,747,253 to Ecker et al., issued May 5, 1998.
PCT application US99/22436 (WO 00/18778) to Lohse et al., published Apr. 6, 2000.
Arar et al. (1995), Bioconjug. Chem., 6, 573.
Ausubel et al. (1988) Current Protocols in Molecular Biology, John Wiley & Sons, New York.
Behr et al. (1989) Proc. Nat Acad. Sci. USA, 86, 6982–6986.
Beven et al. (1997) Biochim. Biophys. Acta, 1329, 357–369.
Boletta et al., (1997), Hum. Gene Ther., 8, 1243.
Bongartz et al. (1994), Nucleic Acids Res., 22, 4681.
Boussif et al. (1996), Gene Ther., 3, 1074.
Briggs et al. (1986), Adv. Prot. Chem. 38, 109).
Brugidou et al. (1995), Biochem. Biophys. Res. Commun., 214, 685.
Chaloin et al. (1998), Biochem. Biophys. Res. Commun., 243, 601.
Chaloin et al. (1997) Biochemistry, 36, 11179–11187.
Chaloin et al., 1997, Lett. Pept. Sci., 4, 231.
Chaloin et al. (1998), Biochim. Biophys. Acta, 1375, 52.
Chen et al. (1999) Proc. Natl. Acad. Sci. USA, 96:4325–4329.
Degols et al. (1989) Nucleic Acids Res., 19, 945.
Degols et al. (1994), Bioconjug. Chem., 5, 8.
Demeneix et al. (1991) Int. J. Dev. Biol., 35, 481.
Derossi et al., (1996), J. Biol. Chem., 271, 18188.
Dingwall, C. and Laskey, R. (1992) Science, 258, 942–94.
Felgner et al., (1987) Proc. Natl. Acad. Sci. USA, 84, 7413–7417.
Felgner et al. (1994) J. Biol. Chem., 269, 2550–2561.
Fingl, et al., 1975, in "The Pharmacological Basis of Therapeutics", Ch. 1.
Freed et al. (1990) Proc. Natl Acad. Sci. USA, 87, 4650–4654.
Galaktionov et al. (1995) Science, 269, 1575–1577.
Gallaher, W. R. (1987) Cell, 50, 327–328.
Gauthier-Rouvière et al. (1996) Mol. Biol. Cell, 7, 719–729.
Goldfarb et al., 1986, Nature (London), 322, 641.
Gottschalk et al. (1996) Gene Ther., 3, 448–457.
Haensler et al. (1993), Bioconjugate Chem., 4, 372.
Harris, J. D. and Lemoine, N. R. (1996) Trends Genet., 12, 400–405.
Kalderon et al., 1984, Nature (London), 311, 33.
Kyte and Doolittle (1982) J. Mol. Biol. 157: 105–132.
Labat-Moleur et al. (1996), Gene Ther., 3, 1010.
Lemaitre et al. (1987), Proc. Natl. Acad. Sci. USA, 84, 648.
Leonetti et al. (1988) Gene, 72, 323.
Leserman et al. (1980) Nature (London) 288, 602.
Levine (1997) Cell, 88:323–331.
Lewis et al. (1996) Proc. Natl Acad. Sci. USA, 93, 3176–3181.
Machy and Leserman, (1983), Biochim. Biophys. Acta, 730, 313.
Méry et al. (1993) Int. J. Peptide Prot. Res., 42, 44–52.
Millar et al. (1991) Proc. Natl Acad. Sci. USA, 88, 10500–10504.
Morris, M. C. (1997) Ph.D. Thesis, Montpellier University, Montpellier, France.
Morris et al. (1997) Nucleic Acids Res., 25, 2730.
Morris et al. (1999) Nucleic Acids Res., 27, 3510–3517.
Morris et al. (1999) J. Biol. Chem., 274, 24942–24946.
Morris et al. (2000) J. Biol. Chem., 275:28849–28857.
Mosmann, T. (1983) J. Immunol. Methods, 65, 55–63.
Nagata et al. (1991) New Biologist, 3, 959–968.
Niidome et al., H., 1997, J. Biol. Cham., 272, 15307–15312.
Pasqualini and Ruoslahti, Nature 380:364–366 (1999).
Phelan et al. (1998) Nat. Biotechnol., 16:440–443.
Prabhakaran, Biochem. J. (1990) 269:691–696.
Pichon et al. (1997), Mol. Pharmacol., 51, 431.
Plank et al. (1994) J. Biol. Chem., 269, 12918–12924.
Radler et al (1997), Science, 275, 810.
"Remington's Pharmaceutical Sciences," Mack Publishing Co., Easton, Pa., latest edition.
Russel et al. (1986) Cell, 45, 145–153).
Sheldon et al. (1995), Proc. Natl., Acad. Sci. USA, 92, 2056.
Sherf et al. (1996) Promega Notes, 57, 2–9.
Van Mau et al. (1999), J. Membrane Biol., 167, 241.
Vidal et al. (1997) Comptes Rendus Acad. Sci. Paris, 320, 279–287.
Vidal et al. (1996) J. Peptide Sci., 2, 125–133.
Vidal et al. (1997) Lett. Peptide Sci., 4, 227–230.
Vidal et al. (1998), J. Membrane Biol., 162, 259.
Vives et al. (1997), J. Biol. Chem., 272, 16010.
Wagner et al.(1992) Proc. Natl. Acad. Sci. USA, 89, 7934–7938.
Wyman et al. (1997) Biochemistry, 36, 3008–3017.
Zhou et al. (1994), Biochim. Biophys. Acta, 1189, 195.

We claim:

1. A transfection agent comprising a peptide of between about 16 to 30 amino a acid residues, said peptide comprising:
   a) a hydrophobic domain comprising at least four amino acid residues, wherein the hydrophobic domain comprises a plurality of aromatic amino acid residues and a first hydrophobic locus spaced by at least one amino acid residue from a second hydrohpobic locus, wherein each of the first and second hydrophobic loci comprise one or more hydrophobic amino acid residues independently selected from the group consisting of Phe, Tyr, Trp, Thr, Met, Leu, Val, Ile, Ala, and His, and wherein at least two of said plurality of aromatic amino acid residues occur in a pair in the first hydrophobic locus or the second hydrophobic locus;
   b) a hydrophilic domain comprising up to about twelve amino acid residues, wherein the hydrophilic domain comprises a plurality of basic amino acid residues;
   c) optionally a spacer sequence between said hydrophobic and said hydrophilic domain, wherein said spacer comprises from between one to about ten amino acid residues; and
   d) further optionally a functional group conjugated to one or more termini of said peptide.

2. A transfection agent according to claim 1 wherein said hydrophilic domain is a cation-rich sequence comprised of at least two lysine residues within a span of seven residues.

3. A transfection agent according to claim 1 wherein at least two of said plurality of aromatic amino acid residues occur in a pair in the first hydrophobic locus or the second hydrophobic locus.

4. A transfection agent according to claim 2 wherein two or more of said at least two lysine residues are adjacent to one another.

5. A transfection agent according to claim 1 wherein said plurality of aromatic amino acid residues is between three and five aromatic amino acid residues inclusive.

6. A transfection agent according to claim 1 wherein said plurality of aromatic amino acid residues comprises at least two tryptophan residues.

7. A transfection agent according to claim 1 comprising two pairs of aromatic amino acid residues, the first pair being disposed in the first hydrophobic locus and the second pair being disposed in the second hydrophobic locus, and wherein said first and second hydrophobic loci are separated by two amino acids.

8. A transfection agent according to claim 7 wherein said two amino acids separating the first and second hydrophobic loci consist of hydrophilic amino acids.

9. A transfection agent according to claim 8 wherein said hydrophilic amino acids separating the first and second hydrophobic loci are Glu and Thr.

10. A transfection agent according to claim 1 wherein said peptide is a synthetic peptide.

11. A transfection agent according to claim 1 wherein said optional spacer sequence comprises one or more amino acid residues selected from the group consisting of proline, glycine, tyrosine, serine, glutamine, and non-charged amino acids.

12. A transfection agent according to claim 1 wherein said hydrophobic domain comprises a motif (Trp/Tyr)-(Trp/Tyr)-Xaa-Xaa-(Trp/Tyr), wherein the first and second hydrophobic loci are spaced by two amino acids, Xaa-Xaa, wherein each Xaa is a hydrophilic amino acid.

13. A transfection agent according to claim 1 wherein said agent is covalently affixed to a compound selected from the group consisting of a nucleic acid, a peptide, a protein, an antibody, and a derivatives or analog of any of the foregoing.

14. A transfection agent according to claim 1 wherein said agent is non-covalently complexed with a compound selected from the group consisting of a nucleic acid, a peptide, a protein, an antibody, and a derivative or analog of any of the foregoing.

15. A transfection agent according to claim 1 that further comprises a functional group covalently attached to a terminus of said peptide, wherein the functional group is selected from the group consisting of a cystearnine group, a methyl group, and an alkyl group, and, with respect to the amino terminus of said peptide, an acyl group.

16. A transfection agent according to claim 1 wherein said hydrophilic domain comprises the sequence Lys-Arg-Lys, and wherein said agent further comprises a spacer sequence that comprises at least three amino acid residues of which at least one is a proline or glutamine residue.

17. A transfection agent according to claim 1 that further comprises a functional group to which is covalently conjugated a molecule selected from the group consisting of a stabilizer, a coupler, a dye, a ligand, and an enzymatic substrate.

18. A commercial transfection kit comprising at least one transfection agent according to claim 1 in either aqueous or lyophilized form, said kit further comprising one or more components selected from the group consisting of buffers, positive controls, cells to be transfected, phospholipids, and instructions for use.

19. A pharmaceutical composition comprising a transfection agent according to claim 1.

20. A pharmaceutical composition according to claim 19 wherein said transfection agent is non-covalently complexed with a compound to be delivered to a cell.

21. A pharmaceutical composition according to claim 20 wherein said compound comprises a member selected from the group consisting of a diagnostic compound and a therapeutic compound.

22. A pharmaceutical composition according to claim 20 wherein said compound is a therapeutic compound that is effective to treat one or more afflictions selected from the group consisting of cancer and infectious diseases.

23. A pharmaceutical composition according to claim 20 wherein said compound targets a cell selected from the group consisting of a cancerous cell and a pathogen-infected cell.

24. A pharmaceutical composition according to claim 20 that is effective to transfect cells of interest using molar ratios of agent:compound of between 5:1 and 30:1.

25. A pharmaceutical composition according to claim 20 in aqueous form in which the compound is present at a concentration of between about 0.1 uM and about 100 uM.

26. A pharmaceutical composition according to claim 20 in aqueous form in which the compound is present at a molar concentration of between about 1 uM and about 20 uM.

27. A transfection agent comprising a peptide of between about 16 to 30 amino acid residues, said peptide comprising:
   a) a hydrophobic domain comprising at least four amino acid residues, wherein the hydrophobic domain comprises three to five aromatic amino acid residues and a first hydrophobic locus spaced by at least one amino acid residue from a second hydrohpobic locus, wherein each of the first and second hydrophobic loci comprise one or more hydrophobic amino acid residues independently selected from the group consisting of Phe, Tyr, Trp, Thr, Met, Leu, Val, Ile, Ala, and His;
   b) a hydrophilic domain comprising up to about twelve amino acid residues, wherein the hydrophilic domain comprises a plurality of basic amino acid residues;
   c) optionally a spacer sequence between said hydrophobic and said hydrophilic domain, wherein said spacer comprises from between one to about ten amino acid residues; and
   d) further optionally a functional group conjugated to one or more termini of said peptide.

28. A transfection agent according to claim 27 wherein said hydrophilic domain is a cation-rich sequence comprised of at least two lysine residues within a span of seven residues.

29. The transfection agent of claim 27 wherein at least two of said plurality of aromatic amino acid residues occur in a pair in the first hydrophobic locus or the second hydrophobic locus.

30. The transfection agent of claim 28 wherein two or more of said at least two lysine residues are adjacent to one another.

31. The transfection agent of claim 27 wherein said plurality of aromatic amino acid residues is between three and five aromatic amino acid residues inclusive.

32. The transfection agent of claim 27 wherein said plurality of aromatic amino acid residues comprises at least two tryptophan residues.

33. The transfection agent of claim 27 comprising two pairs of aromatic amino acid residues, the first pair being disposed in the first hydrophobic locus and the second pair being disposed in the second hydrophobic locus, and wherein said first and second hydrophobic loci are separated by two amino acids.

34. The transfection agent of claim 33 wherein said two amino acids separating the first and second hydrophobic loci consist of hydrophilic amino acids.

35. The transfection agent of claim 34 wherein said hydrophilic amino acids separating the first and second hydrophobic loci are Glu and Thr.

36. A transfection agent according to claim 27 wherein said peptide is a synthetic peptide.

37. A transfection agent according to claim 27 wherein said optional spacer sequence comprises one or more amino acid residues selected from the group consisting of proline, glycine, tyrosine, serine, glutamine, and non-charged amino acids.

38. A transfection agent according to claim 27 wherein said hydrophobic domain comprises a motif (Trp/Tyr)-(Trp/Tyr)-Xaa-Xaa-(Trp/Tyr), wherein the first and second hydrophobic loci are spaced by two amino acids, Xaa-Xaa, wherein each Xaa is a hydrophilic amino acid.

39. A transfection agent according to claim 27 wherein said agent is covalently affixed to a compound selected from the group consisting of a nucleic acid, a peptide, a protein, an antibody, and a derivative or analog of any of the foregoing.

40. A transfection agent according to claim 27 wherein said agent is non-covalently complexed with a compound selected from the group consisting of a nucleic acid, a peptide, a protein, an antibody, and a derivative or analog of any of the foregoing.

41. A transfection agent according to claim 27 that further comprises a functional group covalently attached to a terminus of said peptide, wherein the functional group is selected from the group consisting of a cysteamine group, a methyl group, and an alkyl group, and, with respect to the amino terminus of said peptide, an acyl group.

42. A transfection agent according to claim 27 wherein said hydrophilic domain comprises the sequence Lys-Arg-Lys, and wherein said agent further comprises a spacer sequence that comprises at least three amino acid residues of which at least one is a proline or glutamine residue.

43. A transfection agent according to claim 27 that further comprises a functional group to which is covalently conjugated a molecule selected from the group consisting of a stabilizer, a coupler, a dye, a ligand, and an enzymatic substrate.

44. A commercial transfection kit comprising at least one transfection agent according to claim 27 in either aqueous or lyophilized form, said kit further comprising one or more components selected from the group consisting of buffers, positive controls, cells to be transfected, phospholipids, and instructions for use.

45. A pharmaceutical composition comprising a transfection agent according to claim 27.

46. A pharmaceutical composition according to claim 45 wherein said transfection agent is non-covalently complexed with a compound to be delivered to a cell.

47. A pharmaceutical composition according to claim 46 wherein said compound comprises a member selected from the group consisting of a diagnostic compound and a therapeutic compound.

48. A pharmaceutical composition according to claim 46 wherein said compound is a therapeutic compound that is effective to treat one or more afflictions selected from the group consisting of cancer and infectious diseases.

49. A pharmaceutical composition according to claim 46 wherein said compound targets a cell selected from the group consisting of a cancerous cell and a pathogen-infected cell.

50. A pharmaceutical composition according to claim 46 that is effective to transfect cells of interest using molar ratios of agent:compound of between 5:1 and 30:1.

51. A pharmaceutical composition according to claim 46 in aqueous form in which the compound is present at a concentration of between about 0.1 uM and about 100 uM.

52. A pharmaceutical composition according to claim 46 in aqueous form in which the compound is present at a molar concentration of between about 1 uM and about 20 uM.

53. A transfection agent comprising a peptide of between about 16 to 30 amino acid residues, said peptide comprising:
 a) a hydrophobic domain comprising at least four amino acid residues, wherein the hydrophobic domain comprises a plurality of aromatic amino acid residues and a first hydrophobic locus spaced by at least one amino acid residue from a second hydrohpobic locus, wherein each of the first and second hydrophobic loci comprise one or more hydrophobic amino acid residues independently selected from the group consisting of Phe, Tyr, Trp, Thr, Met, Leu, Val, Ile, Ala, and His;
 b) a hydrophilic domain comprising up to about 12 amino acid residues, wherein the hydrophilic domain comprises a plurality of basic amino acid residues;
 c) optionally a spacer sequence between said hydrophobic and said hydrophilic domains, wherein said spacer comprises from between one to about ten amino acid residues; and
 d) further optionally a functional group conjugated to one or more termini of said peptide.

54. A transfection agent according to claim 53 wherein said hydrophilic domain is a cation-rich sequence comprised of at least two lysine residues within a span of seven residues.

55. The transfection agent of claim 53 wherein at least two of said plurality of aromatic amino acid residues occur in a pair in the first hydrophobic locus or the second hydrophobic locus.

56. The transfection agent of claim 54 wherein two or more of said at least two lysine residues are adjacent to one another.

57. The transfection agent of claim 53 wherein said plurality of aromatic amino acid residues is between three and five aromatic amino acid residues inclusive.

58. The transfection agent of claim 53 wherein said plurality of aromatic amino acid residues comprises at least two tryptophan residues.

59. The transfection agent of claim 53 comprising two pairs of aromatic amino acid residues, the first pair being disposed in the first hydrophobic locus and the second pair being disposed in the second hydrophobic kcus, and wherein said first and second hydrophobic loci are separated by two amino acids.

60. The transfection agent of claim 59 wherein said two amino acids separating the first and second hydrophobic loci consist of hydrophilic amino acids.

61. The transfection agent of claim 60 wherein said hydrophilic amino acids separating the first and second hydrophobic loci are Glu and Thr.

62. A transfection agent according to claim 53 wherein said peptide is a synthetic peptide.

63. A transfection agent according to claim 53 wherein said optional spacer sequence comprises one or more amino acid residues selected from the group consisting of proline, glycine, tyrosine, serine, glutamine, and non-charged amino acids.

64. A transfection agent according to claim 53 wherein said hydrophobic domain comprises a motif (Trp/Tyr)-(Trp/Tyr)-Xaa-Xaa-(Trp/Tyr), wherein the first and second hydrophobic loci are spaced by two amino acids, Xaa-Xaa, wherein each Xaa is a hydrophilic amino acid.

65. A transfection agent according to claim 53 wherein said agent is covalently affixed to a compound selected from the group consisting of a nucleic acid, a peptide, a protein, an antibody, and a derivative/or analog of any of the foregoing.

66. A transfection agent according to claim 53 wherein said agent is non-covalently complexed with a compound selected from the group consisting of a nucleic acid, a peptide, a protein, an antibody, and a derivatives or analog of any of the foregoing.

67. A transfection agent according to claim 53 that further comprises a functional group covalently attached to a terminus of said peptide, wherein the functional group is selected from the group consisting of a cysteanline group, a methyl group, and an alkyl group, and, with respect to the amino terminus of said peptide, an acyl group.

68. A transfection agent according to claim 53 wherein said hydrophilic domain comprises the sequence Lys-Arg-Lys, and wherein said agent further comprises a spacer sequence that comprises at least three amino acid residues of which at least one is a proline or glutamine residue.

69. A transfection agent according to claim 53 that further comprises a functional group to which is covalently conjugated a molecule selected from the group consisting of a stabilizer, a coupler, a dye, a ligand, and an enzymatic substrate.

70. A commercial transfection kit comprising at least one transfection agent according to claim 53 in either aqueous or lyophilized form, said kit further comprising one or more components selected from the group consisting of buffers, positive controls, cells to be transfected, phospholipids, and instructions for use.

71. A pharmaceutical composition comprising a transfection agent according to claim 53.

72. A pharmaceutical composition according to claim 71 wherein said transfection agent is non-covalently complexed with a compound to be delivered to a cell.

73. A pharmaceutical composition according to claim 72 wherein said compound comprises a member selected from the group consisting of a diagnostic compound and a therapeutic compound.

74. A pharmaceutical composition according to claim 72 wherein said compound is a therapeutic compound that is effective to treat one or more afflictions selected from the group consisting of cancer and infectious diseases.

75. A pharmaceutical composition according to claim 72 wherein said compound targets a cell selected from the group consisting of a cancerous cell and a pathogen-infected cell.

76. A pharmaceutical composition according to claim 72 that is effective to transfect cells of interest using molar ratios of agent:compound of between 5:1 and 30:1.

77. A pharmaceutical composition according to claim 72 in aqueous form in which the compound is present at a concentration of between about 0.1 uM and about 100 uM.

78. A pharmaceutical composition according to claim 72 in aqueous form in which the compound is present at a molar concentration of between about 1 uM and about 20 uM.

79. A transfection agent comprising a peptide of between about 16 to 30 amino acid residues in length, said peptide comprising:
 a) a hydrophobic domain comprising at least four amino acid residues, wherein the hydrophobic domain comprises a first hydrophobic locus spaced by at least one amino acid residue from a second hydrohpobic locus, wherein each of the first and second hydrophobic loci comprise one or more hydrophobic amino acid residues independently selected from the group consisting of Phe, Tyr, Trp, Thr, Met, Leu, Val, Ile, Ala, and His;

b) a hydrophilic domain comprising up to about 12 amino acid residues, wherein the hydrophilic domain comprises a plurality of basic amino acid residues;

c) optionally a spacer sequence between said hydrophobic and said hydrophilic domains, wherein said spacer comprises from between one to about ten amino acid residues; and d) further optionally a functional group conjugated to one or more termini of said peptide, wherein the peptide comprises an amino acid sequence selected from the group consisting of SEQ ID NO. 1 through 12.

80. A transfection agent according to claim 79 wherein said peptide is a synthetic peptide.

81. A transfection agent according to claim 79 wherein said agent is covalently affixed to a compound selected from the group consisting of a nucleic acid, a peptide, a protein, an antibody, and a derivative or analog of any of the foregoing.

82. A transfection agent according to claim 79 wherein said agent is non-covalently complexed with a compound selected from the group consisting of a nucleic acid, a peptide, a protein, an antibody, and a derivatives or analog of any of the foregoing.

83. A transfection agent according to claim 79 that further comprises a functional group covalently attached to a terminus of said peptide, wherein the functional group is selected from the group consisting of a cysteamine group, a methyl group, and an alkyl group, and, with respect to the amino terminus of said peptide, an acyl group.

84. A transfection agent according to claim 79 wherein said hydrophilic domain comprises the sequence Lys-Arg-Lys, and wherein said agent further comprises a spacer sequence that comprises at least three amino acid residues of which at least one is a proline or glutamine residue.

85. A transfection agent according to claim 79 that further comprises a functional group to which is covelently conjugated a molecule selected from the group consisting of a stabilizer, a coupler, a dye, a ligand, and an enzymatic substrate.

86. A commercial transfection kit comprising at least one transfection agent according to claim 79 in either aqueous or lyophilized form, said kit further comprising one or more components selected from the group consisting of buffers, positive controls, cells to be transfected, phospholipids, and instructions for use.

87. A pharmaceutical composition comprising a transfection agent according to claim 79.

88. A pharmaceutical composition according to claim 87 wherein said transfection agent is non-covalently complexed with a compound to be delivered to a cell.

89. A pharmaceutical composition according to claim 88 wherein said compound comprises a member selected from the group consisting of a diagnostic compound and a therapeutic compound.

90. A pharmaceutical composition according to claim 88 wherein said compound is a therapeutic compound that is effective to treat one or more afflictions selected from the group consisting of cancer and infectious diseases.

91. A pharmaceutical composition according to claim 88 wherein said compound targets a cell selected from the group consisting of a cancerous cell and a pathogen-infected cell.

92. A pharmaceutical composition according to claim 88 that is effective to transfect cells of interest using molar ratios of agent:compound of between 5:1 and 30:1.

93. A pharmaceutical composition according to claim 88 in aqueous form in which the compound is present at a concentration of between about 0.1 uM and about 100 uM.

94. A pharmaceutical composition according to claim 88 in aqueous form in which the compound is present at a molar concentration of between about 1 uM and about 20 uM.

95. A commercial transfection kit comprising at least one transfection agent comprising a peptide of between about 16 to 30 amino acid residues, said peptide comprising:

a) a hydrophobic domain comprising at least four amino acid residues, wherein the hydrophobic domain comprises a first hydrophobic locus spaced by at least one amino acid residue from a second hydrohpobic locus, wherein each of the first and second hydrophobic loci comprise one or more hydrophobic amino acid residues independently selected from the group consisting of Phe, Tyr, Trp, Thr, Met, Leu, Val, Ile, Ala, and His;

b) a hydrophilic domain comprising up to about 12 amino acid residues, wherein the hydrophilic domain comprises a plurality of basic amino acid residues;

c) optionally a spacer sequence between said hydrophobic and said hydrophilic domains, wherein said spacer comprises from between one to about ten amino acid residues; and d) further optionally a functional group conjugated to one or more termini of said peptide, wherein the transfection agent is in either aqueous or lyophilized form, and wherein said kit further comprises one or more components selected from the group consisting of buffers, positive controls, cells to be transfected, phospholipids, and instructions for use.

96. A kit according to claim 95 wherein said hydrophilic domain is a cation-rich sequence comprised of at least two lysine residues within a span of seven residues.

97. A kit according to claim 95 wherein at least two of said plurality of aromatic amino acid residues occur in a pair in the first hydrophobic locus or the second hydrophobic locus.

98. A kit according to claim 96 wherein two or more of said at least two lysine residues are adjacent to one another.

99. A kit according to claim 95 wherein said plurality of aromatic amino acid residues is between three and five aromatic amino acid residues inclusive.

100. A kit according to claim 95 wherein said plurality of aromatic amino acid residues comprises at least two tryptophan residues.

101. A kit according to claim 95 comprising two pairs of aromatic amino acid residues, the first pair being disposed in the first hydrophobic locus and the second pair being disposed in the second hydrophobic locus, and wherein said first and second hydrophobic loci are separated by two amino acids.

102. A kit according to claim 101 wherein said two amino acids separating the first and second hydrophobic loci consist of hydrophilic amino acids.

103. A kit according to claim 102 wherein said hydrophilic amino acids separating the first and second hydrophobic loci are Glu and Thr.

104. A kit according to claim 95 wherein said peptide is a synthetic peptide.

105. A kit according to claim 95 wherein said optional spacer sequence comprises one or more amino acid residues selected from the group consisting of proline, glycine, tyrosine, serine, glutamine, and non-charged amino acids.

106. A kit according to claim 95 wherein said hydrophobic domain comprises a motif (Trp/Tyr)-(Trp/Tyr)-Xaa-Xaa-(Trp/Tyr), wherein the first and second hydrophobic loci are spaced by two amino acids, Xaa-Xaa, wherein each Xaa is a hydrophilic amino acid.

107. A kit according to claim 95 wherein said agent is covalently affixed to a compound selected from the group consisting of a nucleic acid, a peptide, a protein, an antibody, and a derivatives or analog of any of the foregoing.

108. A kit according to claim 95 wherein said agent is non-covalently complexed with a compound selected from the group consisting of a nucleic acid, a peptide, a protein, an antibody, and a derivatives or analog of any of the foregoing.

109. A kit according to claim 95 that further comprises a functional group covalently attached to a terminus of said peptide, wherein the functional group is selected from the group consisting of a cysteamine group, a methyl group, and an alkyl group, and, with respect to the amino terminus of said peptide, an acyl group.

110. A kit according to claim 95 wherein said hydrophilic domain comprises the sequence Lys-Arg-Lys, and wherein said agent further comprises a spacer sequence that comprises at least three amino acid residues of which at least one is a proline or glutamine residue.

111. A kit according to claim 95 that further comprises a functional group to which is covelently conjugated a molecule selected from the group consisting of a stabilizer, a coupler, a dye, a ligand, and an enzymatic substrate.

112. A kit according to claim 95 wherein the transfection agent is formulated as a pharmaceutical composition.

113. A kit according to claim 112 wherein said transfection agent is non-covalently complexed with a compound to be delivered to a cell.

114. A kit according to claim 113 wherein said compound comprises a member selected from the group consisting of a diagnostic compound and a therapeutic compound.

115. A kit according to claim 113 wherein said compound is a therapeutic compound that is effective to treat one or more afflictions selected from the group consisting of cancer and infectious diseases.

116. A kit according to claim 113 wherein said compound targets a cell selected from the group consisting of a cancerous cell and a pathogen-infected cell.

117. A kit according to claim 113 wherein said compound is effective to transfect cells of interest using molar ratios of agent:compound of between 5:1 and 30:1.

118. A kit according to claim 113 wherein said composition is in aqueous form and the compound is present at a concentration of between about 0.1 uM and about 100 uM.

119. A kit according to claim 113 wherein said composition is in aqueous form and the compound is present at a molar concentration of between about 1 uM and about 20 uM.

* * * * *